(12) United States Patent
Bou Hamdan et al.

(10) Patent No.: US 12,043,600 B2
(45) Date of Patent: Jul. 23, 2024

(54) MICROBIOCIDAL COMPOUNDS

(71) Applicant: SYNGENTA CROP PROTECTION AG, Basel (CH)

(72) Inventors: Farhan Bou Hamdan, Stein (CH); Matthias Weiss, Stein (CH); Atul Mahajan, Goa (IN); Jagadeesh Prathap Kilaru, Goa (IN); Ramya Rajan, Goa (IN); Laura Quaranta, Basel (CH); Stefano Rendine, Stein (CH); Mathias Blum, Stein (CH); Martin Pouliot, Stein (CH); Simon Williams, Stein (CH); Thomas James Hoffman, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 458 days.

(21) Appl. No.: 17/285,155

(22) PCT Filed: Oct. 17, 2019

(86) PCT No.: PCT/EP2019/078143
§ 371 (c)(1),
(2) Date: Apr. 14, 2021

(87) PCT Pub. No.: WO2020/079111
PCT Pub. Date: Apr. 23, 2020

(65) Prior Publication Data
US 2021/0363107 A1 Nov. 25, 2021

(30) Foreign Application Priority Data
Oct. 18, 2018 (IN) .............. 201811039536

(51) Int. Cl.
C07D 231/16 (2006.01)
A01N 43/56 (2006.01)
A01N 43/647 (2006.01)
C07D 231/12 (2006.01)
C07D 231/22 (2006.01)
C07D 249/06 (2006.01)

(52) U.S. Cl.
CPC .......... C07D 231/16 (2013.01); A01N 43/56 (2013.01); A01N 43/647 (2013.01); C07D 231/12 (2013.01); C07D 231/22 (2013.01); C07D 249/06 (2013.01)

(58) Field of Classification Search
CPC .......................... C07D 231/22; C07D 249/06
See application file for complete search history.

(56) References Cited

U.S. PATENT DOCUMENTS 5,008,275 A 4/1991 Klausener et al.
2021/0307328 A1 10/2021 Matsuzaki et al.

FOREIGN PATENT DOCUMENTS

| CN | 112512321 A | 3/2021 |
| EP | 0212859 A2 | 3/1987 |
| EP | 0383117 A2 | 8/1990 |

OTHER PUBLICATIONS

Written Opinion of the International Searching Authority and International Search Report for International Patent Application No. PCT/EP2019/078143 dated Dec. 16, 2019.

Primary Examiner — Johann R Richter
Assistant Examiner — Danielle Johnson
(74) Attorney, Agent, or Firm — BakerHostetler; Toni-Junell Herbert

(57) ABSTRACT

Compounds of the formula (I), wherein the substituents are as defined in claim 1, useful as a pesticides, especially as fungicides.

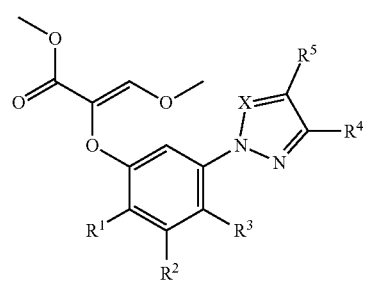

8 Claims, No Drawings

MICROBIOCIDAL COMPOUNDS

CROSS-REFERENCE TO RELATED APPLICATIONS

This application is a 371 National Stage application of International Application No. PCT/EP2019/078143 filed Oct. 17, 2019, which claims priority to IN 201811039536, filed Oct. 18, 2018, the entire contents of these applications are hereby incorporated by reference.

The present invention relates to microbiocidal methoxyacrylate derivatives, e.g., as active ingredients, which have microbiocidal activity, in particular, fungicidal activity. The invention also relates to agrochemical compositions which comprise at least one of the methoxyacrylate derivatives, to processes of preparation of these compounds and to uses of the methoxyacrylate derivatives or compositions in agriculture or horticulture for controlling or preventing infestation of plants, harvested food crops, seeds or non-living materials by phytopathogenic microorganisms, preferably fungi.

EP 0 212 859 and WO 01/00562 describe the use of methoxyacrylate derivatives for combating phytopathogenic fungi.

According to the present invention, there is provided a compound of formula (I):

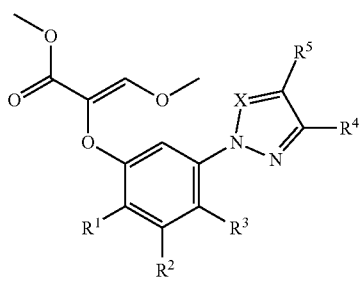

wherein
X is CH or N;
$R^1$ is selected from the group consisting of hydrogen, halogen, $C_1$-$C_3$alkyl and cyclopropyl;
$R^2$ is selected from the group consisting of hydrogen, halogen, methyl and methoxy;
$R^3$ is selected from the group consisting of hydrogen, halogen, methyl and methoxy;
$R^4$ is selected from the group consisting of hydrogen, halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_2$-$C_3$haloalkynyl, cyano$C_1$-$C_6$alkyl-, cyproyl$C_1$-$C_6$alkyl-, methoxy$C_3$-$C_6$alkenyl-, cyclopropyl$C_2$-$C_6$alkenyl-, methoxy$C_3$-$C_4$alkynyl-, cyclopropyl$C_2$-$C_3$alkynyl-, $C_1$-$C_6$alkoxy, $C_1$-$C_6$haloalkoxy, cyclopropyl$C_1$-$C_6$alkoxy-, $C_1$-$C_3$alkoxy$C_1$-$C_3$alkoxy-, $C_1$-$C_3$alkoxy$C_1$-$C_3$alkyl-, $C_1$-$C_6$alkylsulfanyl, $C_1$-$C_6$haloalkylsulfanyl, methoxy$C_1$-$C_6$alkylsulfanyl-, cyclopropyl$C_1$-$C_6$alkylsulfanyl-, $C_1$-$C_3$alkylsulfanyl$C_1$-$C_2$alkyl-, $C_3$-$C_6$cycloalkyl, $C_3$-$C_6$halocycloalkyl, methoxy$C_3$-$C_6$cycloalkyl-, cyclopropyl$C_3$-$C_6$cycloalkyl-, $C_1$-$C_2$alkyl$C_3$-$C_6$cycloalkyl-, —C($R^6$)=NO$R^6$ and —CH$_2$C($R^6$)=NO$R^6$;
$R^5$ is selected from the group consisting of hydrogen, halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_2$-$C_3$haloalkynyl, cyproyl$C_1$-$C_6$alkyl-, methoxy$C_3$-$C_6$alkenyl-, cyclopropyl$C_2$-$C_6$alkenyl-, methoxy$C_3$-$C_4$alkynyl-, cyclopropyl$C_2$-$C_3$alkynyl-, $C_1$-$C_6$alkoxy, $C_{-1}$-$C_6$haloalkoxy, cyclopropyl$C_1$-$C_6$alkoxy-, $C_1$-$C_3$alkoxy$C_1$-$C_3$alkoxy-, $C_1$-$C_3$alkoxy$C_1$-$C_3$alkyl-, $C_1$-$C_6$alkylsulfanyl, $C_1$-$C_6$haloalkylsulfanyl, methoxy$C_1$-$C_6$alkylsulfanyl-, cyclopropyl$C_1$-$C_6$alkylsulfanyl-, $C_1$-$C_3$alkylsulfanyl$C_1$-$C_2$alkyl-, $C_3$-$C_6$cycloalkyl, $C_3$-$C_6$halocycloalkyl, methoxy$C_3$-$C_6$cycloalkyl-, cyclopropyl$C_3$-$C_6$cycloalkyl-, $C_1$-$C_2$alkyl$C_3$-$C_6$cycloalkyl-, —C($R^6$)=NO$R^6$ and —CH$_2$C($R^6$)=NO$R^6$;
and wherein $R^4$ and $R^5$ are not both hydrogen;
each $R^6$ is independently hydrogen or $C_1$-$C_3$alkyl;
or an agronomically acceptable salt thereof;
or an N-oxide thereof.

It has been found that the novel compounds of formula (I) have, a very advantageous level of biological activity for protecting plants against diseases that are caused by fungi.

According to a second aspect of the invention, there is provided an agrochemical composition comprising a fungicidally effective amount of a compound of formula (I) and an agrochemically-acceptable diluent or carrier. Such an agricultural composition may further comprise at least one additional active ingredient.

According to a third aspect of the invention, there is provided a method of controlling or preventing infestation of useful plants by phytopathogenic microorganisms, wherein a fungicidally effective amount of a compound of formula (I), or a composition comprising this compound as active ingredient, is applied to the plants, to parts thereof or the locus thereof.

According to a fourth aspect of the invention, there is provided the use of a compound of formula (I) as a fungicide. According to this particular aspect of the invention, the use may exclude methods for the treatment of the human or animal body by surgery or therapy.

As used herein, the term "halogen" or "halo" refers to fluorine (fluoro), chlorine (chloro), bromine (bromo) or iodine (iodo), preferably fluorine, chlorine or bromine.

As used herein, cyano means a —CN group.

As used herein, hydroxy means a —OH group.

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. $C_1$-$C_4$alkyl and $C_1$-$C_2$alkyl are to be construed accordingly. Examples of $C_1$-$C_6$alkyl include, but are not limited to, methyl, ethyl, n-propyl, 1-methylethyl (iso-propyl), n-butyl, and 1-dimethylethyl (t-butyl).

As used herein, the term "cyano$C_1$-$C_6$alkyl-" refers to a $C_1$-$C_6$alkyl radical as generally defined above substituted by one or more cyano groups.

As used herein, the term "cyclopropyl$C_1$-$C_6$alkyl-" refers to a $C_1$-$C_6$alkyl radical as generally defined above substituted by one or more cyclopropyl groups.

As used herein, the term "$C_1$-$C_6$alkoxy" refers to a radical of the formula —OR$_a$ where R$_a$ is a $C_1$-$C_6$alkyl radical as generally defined above. Examples of $C_1$-$C_6$alkoxy include, but are not limited to, methoxy, ethoxy, propoxy, iso-propoxy and t-butoxy.

As used herein, the term "$C_1$-$C_6$haloalkyl" refers to a $C_1$-$C_6$alkyl radical, as generally defined above, substituted by one or more of the same or different halogen atoms. $C_1$-$C_4$haloalkyl is to be construed accordingly.

Examples of $C_1$-$C_6$haloalkyl include, but are not limited to chloromethyl, fluoromethyl, fluoroethyl, difluoromethyl, trifluoromethyl and 2,2,2-trifluoroethyl.

As used herein, the term "$C_1$-$C_6$haloalkoxy" refers to a $C_1$-$C_6$alkoxy group, as defined above, substituted by one or more of the same or different halogen atoms. $C_1$-$C_4$haloalkoxy is to be construed accordingly. Examples of $C_1$-$C_6$haloalkoxy include, but are not limited to, fluoromethoxy, difluoromethoxy, fluoroethoxy, trifluoromethoxy and trifluoroethoxy.

As used herein, the term "cyclopropyl$C_1$-$C_6$alkoxy-" refers to a $C_1$-$C_6$alkoxy radical as generally defined above substituted by one or more cyclopropyl groups.

As used herein, the term "$C_2$-$C_6$alkenyl" refers to a straight or branched hydrocarbon chain radical consisting solely of carbon and hydrogen atoms, containing at least one double bond that can be of either the (E)- or (Z)-configuration, having from two to six carbon atoms, which is attached to the rest of the molecule by a single bond. $C_3$-$C_6$alkenyl is to be construed accordingly. Examples of $C_2$-$C_6$alkenyl include, but are not limited to, prop-1-enyl, allyl (prop-2-enyl) and but-1-enyl.

As used herein, the term "$C_2$-$C_6$haloalkenyl" refers to a $C_2$-$C_6$alkenyl radical, as generally defined above, substituted by one or more of the same or different halogen atoms.

As used herein, the term "methoxy$C_3$-$C_6$alkenyl-" refers to a $C_3$-$C_6$alkenyl radical as generally defined above substituted by one or more methoxy groups.

As used herein, the term "cyclopropyl$C_2$-$C_6$alkenyl-" refers to a $C_2$-$C_6$alkenyl radical as generally defined above substituted by one or more cyclopropyl groups.

As used herein, the term "$C_2$-$C_3$alkynyl" refers to a straight or branched hydrocarbon chain radical group consisting solely of carbon and hydrogen atoms, containing at least one triple bond, having from two to three carbon atoms, and which is attached to the rest of the molecule by a single bond. Examples of $C_2$-$C_3$alkynyl include, but are not limited to, prop-1-ynyl and propargyl (prop-2-ynyl).

As used herein, the term "methoxy$C_3$-$C_4$alkynyl-" refers to a $C_3$-$C_4$alkynyl radical as generally defined above substituted by one or more methoxy groups.

As used herein, the term "cyclopropyl$C_2$-$C_3$alkynyl-" refers to a $C_2$-$C_3$alkynyl radical as generally defined above substituted by one or more cyclopropyl groups.

As used herein, the term "$C_2$-$C_3$haloalkynyl" refers to a $C_2$-$C_3$alkynyl radical, as generally defined above, substituted by one or more of the same or different halogen atoms.

As used herein, the term "$C_1$-$C_3$alkoxy$C_1$-$C_3$alkyl-" refers to radical of the formula $R_a$—O—$R_b$— where $R_a$ is a $C_1$-$C_3$alkyl radical as generally defined above, and $R_b$ is a $C_1$-$C_3$alkylene radical as generally defined above.

As used herein, the term "$C_1$-$C_3$alkoxy$C_1$-$C_3$alkoxy-" refers to radical of the formula $R_a$—O—$R_b$—O— where $R_a$ is a $C_1$-$C_3$alkyl radical as generally defined above, and $R_b$ is a $C_1$-$C_3$alkyl radical as generally defined above.

As used herein, the term "$C_1$-$C_6$alkylsulfanyl" refers to a radical of the formula —S$R_a$ where $R_a$ is a $C_1$-$C_6$alkyl radical as generally defined above.

As used herein, the term "$C_1$-$C_6$haloalkylsulfanyl" refers to a $C_1$-$C_6$alkylsulfanyl group as defined above substituted by one or more of the same or different halogen atoms.

As used herein, the term "methoxy$C_1$-$C_6$alkylsulfanyl" refers to a $C_1$-$C_6$alkylsulfanyl group as defined above substituted by one or more methoxy groups.

As used herein, the term "cyclopropyl$C_1$-$C_6$alkylsulfanyl" refers to a $C_1$-$C_6$alkylsulfanyl group as defined above substituted by one or more cyclopropyl groups.

As used herein, the term "$C_1$-$C_3$alkylsulfanyl$C_1$-$C_2$alkyl-" refers to radical of the formula $R_a$—S—$R_b$— where $R_a$ is a $C_1$-$C_3$alkyl radical as generally defined above, and $R_b$ is a $C_1$-$C_2$alkylene radical as generally defined above.

As used herein, the term "$C_3$-$C_6$cycloalkyl" refers to a stable, monocyclic ring radical which is saturated or partially unsaturated and contains 3 to 6 carbon atoms. $C_3$-$C_4$cycloalkyl is to be construed accordingly. Examples of $C_3$-$C_6$cycloalkyl include, but are not limited to, cyclopropyl, cyclobutyl, cyclopentyl and cyclohexyl.

As used herein, the term "$C_3$-$C_6$halocycloalkyl" refers to a $C_3$-$C_6$cycloalkyl radical, as generally defined above, substituted by one or more of the same or different halogen atoms. $C_3$-$C_4$halocycloalkyl is to be construed accordingly.

As used herein, the term "methoxy$C_3$-$C_6$cycloalkyl" refers to to a $C_3$-$C_6$cycloalkyl group as defined above substituted by one or more methoxy groups.

As used herein, the term "cyclopropyl$C_3$-$C_6$cycloalkyl" refers to to a $C_3$-$C_6$cycloalkyl group as defined above substituted by one or more cyclopropyl groups.

As used herein, the term "$C_1$-$C_2$alkyl$C_3$-$C_6$cycloalkyl-" refers to to a $C_3$-$C_6$cycloalkyl group as defined above substituted by a $C_1$-$C_2$alkyl radical as defined above.

The presence of one or more possible asymmetric carbon atoms in a compound of formula (I) means that the compounds may occur in chiral isomeric forms, i.e., enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers (including lactam-lactim tautomerism and keto-enol tautomerism) where present. The present invention includes all possible tautomeric forms for a compound of formula (I).

In each case, the compounds of formula (I) according to the invention are in free form, in covalently hydrated form, or in salt form, e.g., an agronomically usable or agrochemically acceptable salt form.

The following list provides definitions, including preferred definitions, for substituents X, $R^1$, $R^2$, $R^3$, $R^4$, $R^5$ and $R^6$ with reference to the compounds of formula (I) according to the invention. For any one of these substituents, any of the definitions given below may be combined with any definition of any other substituent given below or elsewhere in this document.

X is CH or N. Preferably, X is CH.

In another embodiment X is N.

$R^1$ is selected from the group consisting of hydrogen, halogen, $C_1$-$C_3$alkyl and cyclopropyl. Preferably, $R^1$ is selected from the group consisting of hydrogen, chloro, bromo, methyl, ethyl and cyclopropyl. More preferably, $R^1$ is selected from the group consisting of chloro, bromo, methyl, ethyl and cyclopropyl. Even more preferably, $R^1$ is selected from the group consisting of chloro, bromo and methyl. Most preferably, $R^1$ is methyl.

$R^2$ is selected from the group consisting of hydrogen, halogen, methyl and methoxy. Preferably, $R^2$ is selected from the group consisting of hydrogen, fluoro, methyl and methoxy. More preferably, $R^2$ is selected from the group consisting of hydrogen, fluoro and methyl. Even more preferably, $R^2$ is hydrogen or methyl. Most preferably, $R^2$ is hydrogen.

$R^3$ is selected from the group consisting of hydrogen, halogen, methyl and methoxy. Preferably, $R^3$ is selected from the group consisting of hydrogen, fluoro, chloro, methyl and methoxy. More preferably, $R^3$ is selected from the group consisting of hydrogen, fluoro and methyl. Even more preferably, $R^3$ is hydrogen or methyl. Most preferably, $R^3$ is hydrogen.

$R^4$ is selected from the group consisting of hydrogen, halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_2$-$C_3$haloalkynyl, cyano$C_1$-$C_6$alkyl-, cyproyl$C_1$-$C_6$alkyl-, methoxy$C_3$-$C_6$alkenyl-, cyclopropyl$C_2$-$C_6$alkenyl-, methoxy$C_3$-$C_4$alkynyl-, cyclopropyl$C_2$-$C_3$alkynyl-, $C_1$-$C_6$alkoxy, $C_1$-$C_6$haloalkoxy, cyclopropyl$C_1$-$C_6$alkoxy-, $C_1$-$C_3$alkoxy$C_1$-$C_3$alkoxy-, $C_1$-$C_3$alkoxy$C_1$-$C_3$alkyl-, $C_1$-$C_6$alkylsulfanyl, $C_1$-$C_6$haloalkylsulfanyl, methoxy$C_1$-$C_6$alkylsulfanyl-, cyclopropyl$C_1$-$C_6$alkylsulfanyl-, $C_1$-$C_3$alkylsulfanyl$C_1$-$C_2$alkyl-, $C_3$-$C_6$cycloalkyl, $C_3$-$C_6$halocycloalkyl, methoxy$C_3$-$C_6$cycloalkyl-, cyclopropyl$C_3$-$C_6$cycloalkyl-, $C_1$-$C_2$alkyl$C_3$-$C_6$cycloalkyl-, —C($R^6$)=NO$R^6$ and —CH$_2$C($R^6$)=NO$R^6$.

Preferably, $R^4$ is selected from the group consisting of hydrogen, halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_2$-$C_3$haloalkynyl, cyano$C_1$-$C_6$alkyl-, cyproyl$C_1$-$C_6$alkyl-, methoxy$C_3$-$C_6$alkenyl-, cyclopropyl$C_2$-$C_6$alkenyl-, methoxy$C_3$-$C_4$alkynyl-, cyclopropyl$C_2$-$C_3$alkynyl-, $C_1$-$C_6$alkoxy, $C_1$-$C_6$haloalkoxy, $C_1$-$C_3$alkoxy$C_1$-$C_3$alkyl-, $C_1$-$C_6$alkylsulfanyl, $C_1$-$C_6$haloalkylsulfanyl, $C_1$-$C_3$alkylsulfanyl$C_1$-$C_2$alkyl-, $C_3$-$C_6$cycloalkyl, $C_3$-$C_6$halocycloalkyl, $C_1$-$C_2$alkyl$C_3$-$C_6$cycloalkyl- and —C($R^6$)=NO$R^6$.

More preferably, $R^4$ is selected from the group consisting of hydrogen, halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_2$-$C_3$haloalkynyl, cyproyl$C_1$-$C_6$alkyl-, cyclopropyl$C_2$-$C_3$alkynyl-, $C_1$-$C_6$alkoxy, $C_1$-$C_6$haloalkoxy, $C_1$-$C_3$alkoxy$C_1$-$C_3$alkyl-, $C_1$-$C_6$alkylsulfanyl, $C_1$-$C_6$haloalkylsulfanyl, $C_3$-$C_6$cycloalkyl, $C_3$-$C_6$halocycloalkyl and —C($R^6$)=NO$R^6$.

Even more preferably, $R^4$ is selected from the group consisting of hydrogen, halogen, $C_1$-$C_6$alkyl, $C_2$-$C_6$alkenyl, $C_1$-$C_6$haloalkyl, $C_2$-$C_6$haloalkenyl, $C_1$-$C_6$alkoxy, $C_1$-$C_6$haloalkoxy, $C_3$-$C_6$cycloalkyl and $C_3$-$C_6$halocycloalkyl.

Even more preferably still, $R^4$ is selected from the group consisting of halogen, $C_1$-$C_6$alkyl, $C_2$-$C_6$alkenyl, $C_1$-$C_6$haloalkyl, $C_2$-$C_6$haloalkenyl, $C_1$-$C_6$alkoxy, $C_1$-$C_6$haloalkoxy, $C_3$-$C_6$cycloalkyl and $C_3$-$C_6$halocycloalkyl.

Yet even more preferably still, $R^4$ is selected from the group consisting of chloro, bromo, iodo, methyl, ethyl, n-propyl, iso-propyl, n-butyl, iso-butyl, sec-butyl, trifluoromethyl, trifluoroethyl, iso-propyloxy, n-propyloxy, cyclopropyl and cyclobutyl.

In one embodiment $R^4$ is selected from the group consisting of chloro, bromo, iodo, cyano, methyl, ethyl, n-propyl, iso-propyl, ethylpropyl, n-butyl, iso-butyl, sec-butyl, tert-butyl, cyclopropylethynyl, vinyl, prop-1-enyl, 1-methylprop-1-enyl, prop-1-ynyl, difluoromethyl, trifluoromethyl, 1,1-difluoroethyl, 1,1,2,2,2-pentafluoroethyl, trifluoro-1-methyl-ethyl, trifluoromethylvinyl, methylcyclopropyl, methoxy, ethoxy, iso-propyloxy, n-propyloxy, difluoromethoxy, methoxymethyl, trifluromethylsulfanyl, methylsulfanylmethyl, cyclopropyl, cyclobutyl, cyclopentyl, cyclohexyl, cyclohexen-1-yl, fluorocyclopropyl, 2,2-difluorocyclopropyl, —C(CH$_3$)=NOCH$_3$, —C(CH$_3$)=NOCH$_2$CH$_3$ and —C(CH$_3$)=NOH $R^5$ is selected from the group consisting of hydrogen, halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_2$-$C_3$haloalkynyl, cyproyl$C_1$-$C_6$alkyl-, methoxy$C_3$-$C_6$alkenyl-, cyclopropyl$C_2$-$C_6$alkenyl-, methoxy$C_3$-$C_4$alkynyl-, cyclopropyl$C_2$-$C_3$alkynyl-, $C_1$-$C_6$alkoxy, $C_{-1}$-$C_6$haloalkoxy, cyclopropyl$C_1$-$C_6$alkoxy-, $C_1$-$C_3$alkoxy$C_1$-$C_3$alkoxy-, $C_1$-$C_3$alkoxy$C_1$-$C_3$alkyl-, $C_1$-$C_6$alkylsulfanyl, $C_1$-$C_6$haloalkylsulfanyl, methoxy$C_1$-$C_6$alkylsulfanyl-, cyclopropyl$C_1$-$C_6$alkylsulfanyl-, $C_1$-$C_3$alkylsulfanyl$C_1$-$C_2$alkyl-, $C_3$-$C_6$cycloalkyl, $C_3$-$C_6$halocycloalkyl, methoxy$C_3$-$C_6$cycloalkyl-, cyclopropyl$C_3$-$C_6$cycloalkyl-, $C_1$-$C_2$alkyl$C_3$-$C_6$cycloalkyl-, —C($R^6$)=NO$R^6$ and —CH$_2$C($R^6$)=NO$R^6$.

Preferably, $R^5$ is selected from the group consisting of hydrogen, halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_1$-$C_6$alkoxy, $C_1$-$C_6$haloalkoxy, $C_1$-$C_3$alkoxy$C_1$-$C_3$alkyl-, $C_1$-$C_6$alkylsulfanyl, $C_3$-$C_6$cycloalkyl and $C_3$-$C_6$halocycloalkyl.

More preferably, $R^5$ is selected from the group consisting of hydrogen, halogen, $C_1$-$C_6$alkyl, $C_2$-$C_6$alkenyl, $C_1$-$C_6$haloalkyl, $C_2$-$C_6$haloalkenyl, $C_1$-$C_6$alkoxy, $C_1$-$C_6$haloalkoxy, $C_3$-$C_6$cycloalkyl and $C_3$-$C_6$halocycloalkyl.

Even more preferably, $R^5$ is selected from the group consisting of hydrogen, halogen, methyl, ethyl, iso-propyl, tert-butyl, ethoxy, cyclopropyl, cyclopentyl and trifluoromethyl.

Even more preferably still, $R^5$ is selected from the group consisting of hydrogen, halogen, methyl and trifluoromethyl. Most preferably, $R^5$ is hydrogen.

In one embodiment $R^5$ is selected from the group consisting of hydrogen, chloro, bromo, iodo, cyano, methyl, ethyl, n-propyl, iso-propyl, n-butyl, tert-butyl, iso-propenyl, ethynyl, trifluoromethyl, methoxymethyl, iso-propylsulfanyl, cyclopropyl, cyclobutyl, cyclopentyl, cyclohexyl, —C(CH$_3$)=NOCH$_2$CH$_3$ and —C(CH$_3$)=NOH.

Provided that Wand Ware not both hydrogen.

Each $R^6$ is independently hydrogen or $C_1$-$C_3$alkyl. Preferably, each $R^6$ is $C_1$-$C_3$alkyl, most preferably, each $R^6$ is methyl.

Preferably, in a compound according to formula (I) of the invention;

X is CH or N;

$R^1$ is methyl;

$R^2$ is hydrogen;

$R^3$ is hydrogen;

$R^4$ is selected from the group consisting of halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_2$-$C_3$haloalkynyl, cyproyl$C_1$-$C_6$alkyl-, cyclopropyl$C_2$-$C_3$alkynyl-, $C_1$-$C_6$alkoxy, $C_1$-$C_6$haloalkoxy, $C_1$-$C_3$alkoxy$C_1$-

$C_3$alkyl-, $C_1$-$C_6$alkylsulfanyl, $C_1$-$C_6$haloalkylsulfanyl, $C_3$-$C_6$cycloalkyl, $C_3$-$C_6$halocycloalkyl and —C($R^6$)=NOR$^6$;

$R^5$ is selected from the group consisting of hydrogen, halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_1$-$C_6$alkoxy, $C_1$-$C_6$haloalkoxy, $C_1$-$C_3$alkoxy$C_1$-$C_3$alkyl-, $C_1$-$C_6$alkylsulfanyl, $C_3$-$C_6$cycloalkyl and $C_3$-$C_6$halocycloalkyl;

Each $R^6$ is independently hydrogen or $C_1$-$C_3$alkyl.

More preferably, in a compound according to formula (I) of the invention;

X is CH;
$R^1$ is methyl;
$R^2$ is hydrogen;
$R^3$ is hydrogen;
$R^4$ is selected from the group consisting of halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_2$-$C_3$haloalkynyl, cyproylC$_1$-$C_6$alkyl-, cyclopropylC$_2$-$C_3$alkynyl-, $C_1$-$C_6$alkoxy, $C_1$-$C_6$haloalkoxy, $C_1$-$C_3$alkoxy$C_1$-$C_3$alkyl-, $C_1$-$C_6$alkylsulfanyl, $C_1$-$C_6$haloalkylsulfanyl, $C_3$-$C_6$cycloalkyl, $C_3$-$C_6$halocycloalkyl and —C($R^6$)=NOR$^6$;

$R^5$ is selected from the group consisting of hydrogen, halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_1$-$C_6$alkoxy, $C_1$-$C_6$haloalkoxy, $C_1$-$C_3$alkoxy$C_1$-$C_3$alkyl-, $C_1$-$C_6$alkylsulfanyl, $C_3$-$C_6$cycloalkyl and $C_3$-$C_6$halocycloalkyl;

Each $R^6$ is independently hydrogen or $C_1$-$C_3$alkyl.

Even more preferably, in a compound according to formula (I) of the invention;

X is CH;
$R^1$ is methyl;
$R^2$ is hydrogen;
$R^3$ is hydrogen;
$R^4$ is selected from the group consisting of halogen, $C_1$-$C_6$alkyl, $C_2$-$C_6$alkenyl, $C_1$-$C_6$haloalkyl, $C_2$-$C_6$haloalkenyl, $C_1$-$C_6$alkoxy, $C_1$-$C_6$haloalkoxy, $C_3$-$C_6$cycloalkyl and $C_3$-$C_6$halocycloalkyl;

$R^5$ is selected from the group consisting of hydrogen, halogen, $C_1$-$C_6$alkyl, $C_2$-$C_6$alkenyl, $C_1$-$C_6$haloalkyl, $C_2$-$C_6$haloalkenyl, $C_1$-$C_6$alkoxy, $C_1$-$C_6$haloalkoxy, $C_3$-$C_6$cycloalkyl and $C_3$-$C_6$halocycloalkyl.

Even more preferably still, in a compound according to formula (I) of the invention;

X is CH;
$R^1$ is methyl;
$R^2$ is hydrogen;
$R^3$ is hydrogen;
$R^4$ is selected from the group consisting of chloro, bromo, iodo, methyl, ethyl, n-propyl, iso-propyl, n-butyl, iso-butyl, sec-butyl, trifluoromethyl, trifluoroethyl, iso-propyloxy, n-propyloxy, cyclopropyl and cyclobutyl;
$R^5$ is hydrogen.

In an alternative preferred embodiment in a compound according to formula (I) of the invention;

X is CH;
$R^1$ is methyl;
$R^2$ is hydrogen;
$R^3$ is hydrogen;
$R^4$ is selected from the group consisting of hydrogen, halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_2$-$C_3$haloalkynyl, cyproylC$_1$-$C_6$alkyl-, cyclopylC$_2$-$C_3$alkynyl-, $C_1$-$C_6$alkoxy, $C_1$-$C_6$haloalkoxy, $C_1$-$C_3$alkoxy$C_1$-$C_3$alkyl-, $C_1$-$C_6$alkylsulfanyl, $C_1$-$C_6$haloalkylsulfanyl, $C_3$-$C_6$cycloalkyl, $C_3$-$C_6$halocycloalkyl and —C($R^6$)=NOR$^6$;

$R^5$ is selected from the group consisting of halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_1$-$C_6$alkoxy, $C_1$-$C_6$haloalkoxy, $C_1$-$C_3$alkoxy$C_1$-$C_3$alkyl-, $C_1$-$C_6$alkylsulfanyl, $C_3$-$C_6$cycloalkyl and $C_3$-$C_6$halocycloalkyl;

Each $R^6$ is independently hydrogen or $C_1$-$C_3$alkyl.

In an alternative more preferred embodiment in a compound according to formula (I) of the invention;

X is CH;
$R^1$ is methyl;
$R^2$ is hydrogen;
$R^3$ is hydrogen;
$R^4$ is selected from the group consisting of hydrogen, halogen, $C_1$-$C_6$alkyl, $C_2$-$C_6$alkenyl, $C_1$-$C_6$haloalkyl, $C_2$-$C_6$haloalkenyl, $C_1$-$C_6$alkoxy, $C_1$-$C_6$haloalkoxy, $C_3$-$C_6$cycloalkyl and $C_3$-$C_6$halocycloalkyl;

$R^5$ is selected from the group consisting of halogen, $C_1$-$C_6$alkyl, $C_2$-$C_6$alkenyl, $C_1$-$C_6$haloalkyl, $C_2$-$C_6$haloalkenyl, $C_1$-$C_6$alkoxy, $C_1$-$C_6$haloalkoxy, $C_3$-$C_6$cycloalkyl and $C_3$-$C_6$halocycloalkyl.

In an alternative preferred embodiment in a compound according to formula (I) of the invention;

X is N;
$R^1$ is methyl;
$R^2$ is hydrogen;
$R^3$ is hydrogen;
$R^4$ is selected from the group consisting of halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_2$-$C_3$haloalkynyl, cyproylC$_1$-$C_6$alkyl-, cyclopropylC$_2$-$C_3$alkynyl-, $C_1$-$C_6$alkoxy, $C_1$-$C_6$haloalkoxy, $C_1$-$C_3$alkoxy$C_1$-$C_3$alkyl-, $C_1$-$C_6$alkylsulfanyl, $C_1$-$C_6$haloalkylsulfanyl, $C_3$-$C_6$cycloalkyl, $C_3$-$C_6$halocycloalkyl and —C($R^6$)=NOR$^6$;

$R^5$ is selected from the group consisting of hydrogen, halogen, cyano, $C_1$-$C_6$alkyl, $C_2$-$C_6$alkenyl, $C_2$-$C_3$alkynyl, $C_1$-$C_6$haloalkyl, $C_2$-$C_6$haloalkenyl, $C_1$-$C_6$alkoxy, $C_1$-$C_6$haloalkoxy, $C_1$-$C_3$alkoxy$C_1$-$C_3$alkyl-, $C_1$-$C_6$alkylsulfanyl, $C_3$-$C_6$cycloalkyl and $C_3$-$C_6$halocycloalkyl;

Each $R^6$ is independently hydrogen or $C_1$-$C_3$alkyl.

In an alternative more preferred embodiment in a compound according to formula (I) of the invention;

X is N;
$R^1$ is methyl;
$R^2$ is hydrogen;
$R^3$ is hydrogen;
$R^4$ is selected from the group consisting of halogen, $C_1$-$C_6$alkyl, $C_2$-$C_6$alkenyl, $C_1$-$C_6$haloalkyl, $C_2$-$C_6$haloalkenyl, $C_1$-$C_6$alkoxy, $C_1$-$C_6$haloalkoxy, $C_3$-$C_6$cycloalkyl and $C_3$-$C_6$halocycloalkyl;

$R^5$ is selected from the group consisting of hydrogen, halogen, $C_1$-$C_6$alkyl, $C_2$-$C_6$alkenyl, $C_1$-$C_6$haloalkyl, $C_2$-$C_6$haloalkenyl, $C_1$-$C_6$alkoxy, $C_1$-$C_6$haloalkoxy, $C_3$-$C_6$cycloalkyl and $C_3$-$C_6$halocycloalkyl.

In an even more preferred embodiment the compound according to formula (I) is selected from the group consisting of compounds E-1 to E-118 and F-1 to F-13 listed in tables E and F below.

In one embodiment, the compounds of formula (I) according to the invention may be useful for combating phytopathogenic fungi (e.g *Alternaria alternate*, *Phakopsora pachyrhizi*, *Plasmopara viticola*, *Sclerotinia sclerotiorum* or

*Septoria tritici* also known as *Mycosphaerella graminicola*) containing a mutation in the mitochondrial cytochrome b conferring resistance to Qo inhibitors (e.g strobilurins such as azoxystrobin, pyraclostrobin and trifloxystrobin or fenamidone or famoxadone).

In a further embodiment, the compounds of formula (I) according to the invention may be useful for combating phytopathogenic fungi (e.g *Alternaria alternate, Plasmopara viticola, Sclerotinia sclerotiorum* or *Septoria tritici* also known as *Mycosphaerella graminicola*) containing a mutation in the mitochondrial cytochrome b conferring resistance to Qo inhibitors (e.g strobilurins such as azoxystrobin, pyraclostrobin and trifloxystrobin or fenamidone or famoxadone), wherein the mutation is G143A.

In a further embodiment, the compounds of formula (I) according to the invention may be useful for combating phytopathogenic fungi (e.g *Phakopsora pachyrhizi*) containing a mutation in the mitochondrial cytochrome b conferring resistance to Qo inhibitors (e.g strobilurins such as azoxystrobin, pyraclostrobin and trifloxystrobin or fenamidone or famoxadone), wherein the mutation is F129L.

In another embodiment, the invention also relates to a method of controlling or preventing infestation by phytopathogenic fungi in a plant (e.g *Alternaria alternate, Phakopsora pachyrhizi Plasmopara viticola, Sclerotinia sclerotiorum* or *Septoria tritici* also known as *Mycosphaerella graminicola*, preferably *Phakopsora pachyrhizi*), wherein said phytopathogenic fungi contains a mutation in the mitochondrial cytochrome b conferring resistance to Qo inhibitors (e.g strobliurins such as azoxystrobin, pyraclostrobin and trifloxystrobin or fenamidone or famoxadone), said method comprising applying to the plant, to parts thereof or the locus thereof, a fungicidally effective amount of a compound of formula (I).

The level of resistance and therefore the impact on the performance of the fungicide can be measured by the use of a 'Resistance Factor' (RF). The resistance factor can be calculated by dividing the concentration of a fungicide that provides a set level of disease control (i.e. 50 percent) for the 'resistant' fungal strain with the concentration of the same fungicide that provides the same level of disease control for the 'susceptible' strain of the same fungal species (RF=EC50 value of the resistant strain/EC50 value of the sensitive strain). Although there are no set rules, three categories can be defined: 1) RF≥50=resistant strain, 2) 5≤RF<50=less sensitive strain (shift in sensitivity), and 3) RF<5=sensitive strain.

In order to obtain resistant fungal strains, a researcher is to locate a host crop and geographical region where the relevant resistance had been reported in literature. Leaf samples infected by the target disease are then collected from the locations/host crops and sent to a laboratory, where pure cultures would be isolated. The resistant phenotype of the fungal cultures is determined either by conducting a full dose response bioassay and comparing the bioassay results to similar bioassay results for a known susceptible strain of the same species. Alternatively the resistance genotype of the fungal strain can be determined by molecular techniques (e.g. qPCR) if the resistance mechanism for the relevant species is known.

The compounds of formula (I) according to the invention, wherein X, $R^1$, $R^2$, $R^3$, $R^4$, $R^5$ and $R^6$ are as defined for formula (I), can be made as shown in the following schemes.

The compounds of formula (I) according to the invention, wherein X, $R^1$, $R^2$, $R^3$, $R^4$ and $R^5$ are as defined for formula (I), can be obtained by transformation of a compound of formula (II), wherein $R^1$, $R^2$ and $R^3$ are as defined for compounds of formula (I) and $R^{11}$ is halogen (preferably chloro, bromo or iodo) or pseudohalogen (e.g $-OSO_2CH_3$, $-OSO_2CF_3$ or $-OSO_2(CF_2)_3CF_3$) and compounds of formula (III) wherein X, $R^4$ and $R^5$ are as defined for compounds of formula (I), in the presence of a base such as $K_2CO_3$, a palladium compound such as tris(dibenzylideneacetone)dipalladium(0) and a supporting phosphine ligand such as 2-Di-tert-butylphosphino-3,4,5,6-tetramethyl-2',4',6'-triisopropyl-1,1'-biphenyl in an organic solvent such as toluene at temperatures between 20° C.-110° C. Such transformations are described in Angew. Chem. Int. Ed. 2011, p. 8944 and are shown in scheme 1.

Scheme 1

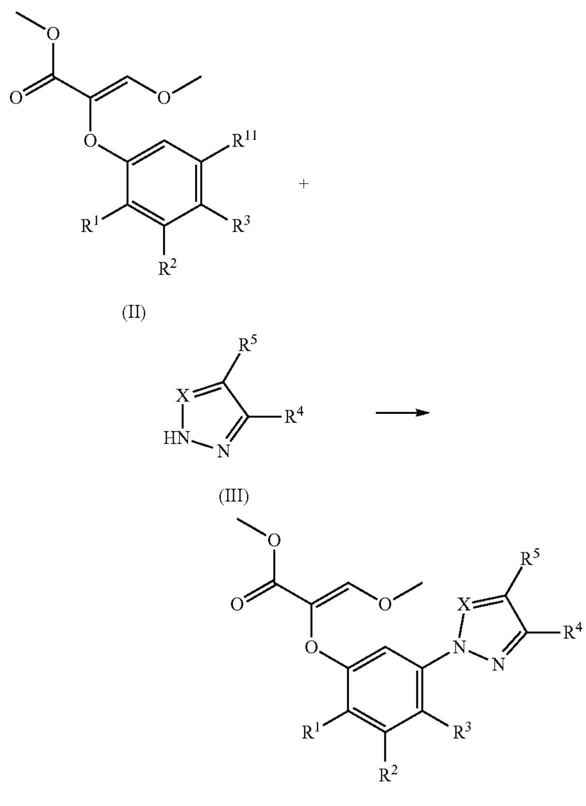

(II)

(III)

(I)

Alternatively, compounds of formula (I) can be obtained from compounds of formula (IV) wherein $R^1$, $R^2$ and $R^3$ are as defined for compounds of formula (I) and $R^{12}$ is as defined in scheme 2, and compounds of formula (III) wherein X, $R^4$ and $R^5$ are as defined for compounds of formula (I), in the presence of a base such as pyridine and a copper salt such as $Cu(OAc)_2$ in an inert organic solvent such as dichloromethane. This is shown in scheme 2.

Scheme 2

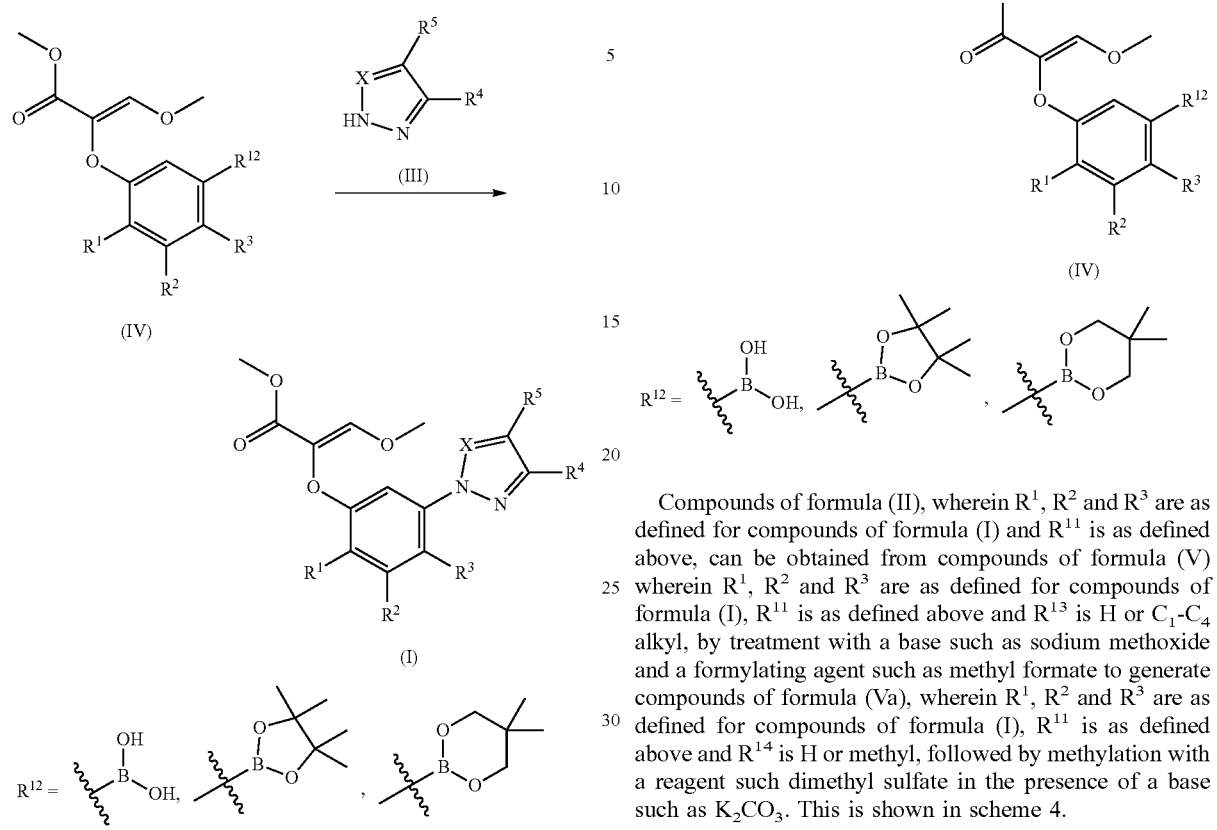

Compounds of formula (IV), wherein $R^1$, $R^2$ and $R^3$ are as defined for compounds of formula (I) and $R^{12}$ is as defined in scheme 2, can be obtained from compounds of formula (II), wherein $R^1$, $R^2$, $R^3$ and $R^{11}$ are as defined above, by treatment with a base such as potassium acetate, a diborane species $R^{12}$—$R^{12}$ wherein $R^{12}$ is as defined in scheme 3, a palladium compound such as tris(dibenzylideneacetone)dipalladium(0) and a supporting phosphine ligand such as 2-Di-cyclohexylphosphino-2',4',6'-triisopropyl-1,1'-biphenyl in an organic solvent such as tetrahydrofuran or ethanol, optionally followed by borane group hydrolysis or transesterification. This is shown in scheme 3.

Compounds of formula (II), wherein $R^1$, $R^2$ and $R^3$ are as defined for compounds of formula (I) and $R^{11}$ is as defined above, can be obtained from compounds of formula (V) wherein $R^1$, $R^2$ and $R^3$ are as defined for compounds of formula (I), $R^{11}$ is as defined above and $R^{13}$ is H or $C_1$-$C_4$ alkyl, by treatment with a base such as sodium methoxide and a formylating agent such as methyl formate to generate compounds of formula (Va), wherein $R^1$, $R^2$ and $R^3$ are as defined for compounds of formula (I), $R^{11}$ is as defined above and $R^{14}$ is H or methyl, followed by methylation with a reagent such dimethyl sulfate in the presence of a base such as $K_2CO_3$. This is shown in scheme 4.

Scheme 4

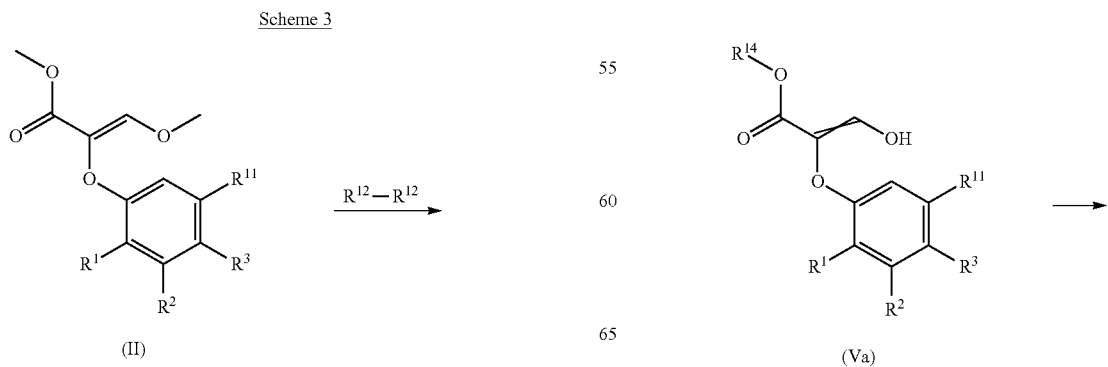

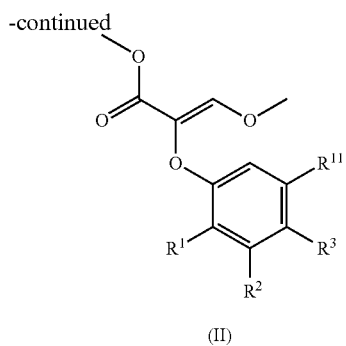

(II)

Compounds of formula (V), wherein $R^1$, $R^2$ and $R^3$ are as defined for compounds of formula (I), $R^{11}$ is as defined above and $R^{13}$ is H or $C_1$-$C_4$ alkyl, can be obtained from compounds of formula (VI) wherein $R^1$, $R^2$ and $R^3$ are as defined for compounds of formula (I) and $R^{11}$ is as defined above, by treatment with a base such as $K_2CO_3$ and an alkylation agent of formula (VII) in an organic solvent such as N-methyl pyrrolidone. This is shown in scheme 5.

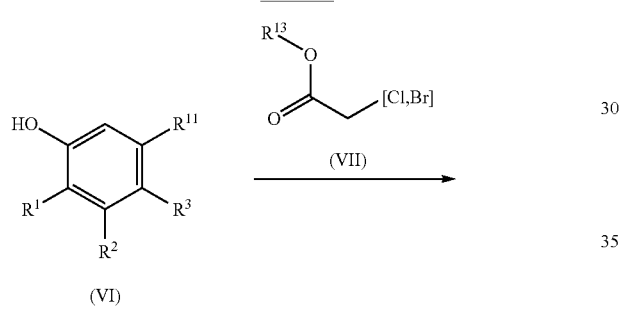

Compounds of formula (VI) wherein $R^1$, $R^2$ and $R^3$ are as defined for compounds of formula (I) and $R^{11}$ is as defined above are commercially available or readily prepared from commercially available compounds by standard functional group transformations well known to a person skilled in the art and described in *March's Advanced Organic Chemistry*, Smith and March, 6$^{th}$ edition, Wiley, 2007.

Alternatively, compounds of formula (I), wherein X, $R^1$, $R^2$, $R^3$, $R^4$ and $R^5$ are as defined for compounds of formula (I), can be obtained from compounds of formula (VIII) wherein X, $R^1$, $R^2$, $R^3$, $R^4$ and $R^5$ are as defined for compounds of formula (I) and $R^{13}$ is H or $C_1$-$C_4$ alkyl, by treatment with a base such as sodium methoxide and a formylating agent such as methyl formate to generate compounds of formula (IX), wherein X, $R^1$, $R^2$, $R^3$, $R^4$ and $R^5$ are as defined for compounds of formula (I) and $R^{14}$ is H or methyl, followed by methylation with a reagent such dimethyl sulfate in the presence of a base such as $K_2CO_3$. This is shown in scheme 6.

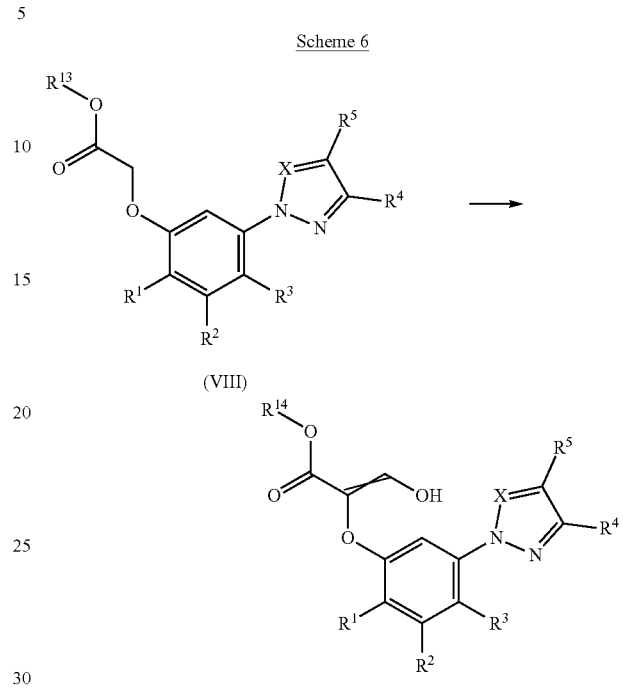

Compounds of formula (VIII), wherein X, $R^1$, $R^2$, $R^3$, $R^4$ and $R^5$ are as defined for compounds of formula (I) and $R^{13}$ is H or $C_1$-$C_4$ alkyl, can be obtained from compounds of formula (V) wherein $R^1$, $R^2$ and $R^3$ are as defined for compounds of formula (I), $R^{13}$ is H or $C_1$-$C_4$ alkyl and $R^{11}$ is halogen (preferably, chloro, bromo, iodo) or pseudohalogen (e.g —$OSO_2CH_3$, —$OSO_2CF_3$ or —$OSO_2(CF_2)_3CF_3$) and compounds of formula (III) wherein X, $R^4$ and $R^5$ are as defined for compounds of formula (I), in the presence of a base such as $K_2CO_3$, a palladium compound such as tris (dibenzylideneacetone)dipalladium(0) and a supporting phosphine ligand such as 2-Di-tert-butylphosphino-3,4,5,6-tetramethyl-2',4',6'-triisopropyl-1,1'-biphenyl in an organic solvent such as toluene at temperatures between 20° C.-110° C. This is shown in scheme 7.

Scheme 7

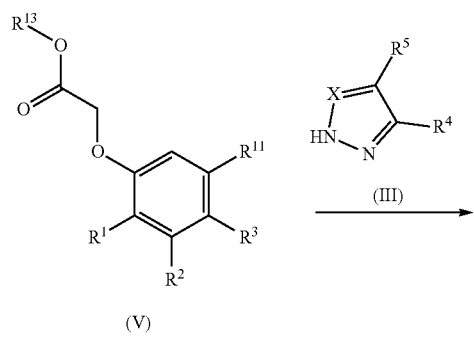

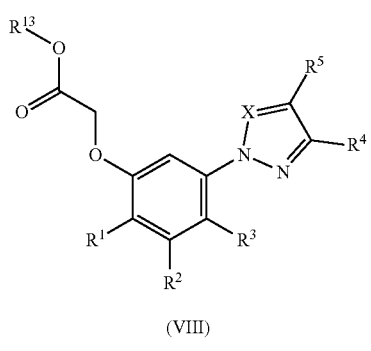

The preparation of compounds of formula (III) wherein X, R⁴ and R⁵ are as defined for compounds of formula (I) is well known to a person skilled in the art and has ample precedence in the scientific literature.

Alternatively, certain compounds of formula (I) can be prepared from compounds of formula (I-a), wherein X, $R^1$, $R^2$, $R^3$ and $R^5$ are as defined for compounds of formula (I) and $R^{14}$ is halogen (preferably chloro, bromo or iodo) or pseudohalogen (e.g —OSO$_2$CH$_3$, —OSO$_2$CF$_3$ or —OSO$_2$(CF$_2$)$_3$CF$_3$), in the presence of a coupling reagent and a transition metal-based catalyst. There are no particular limitations on the coupling agent, catalyst and solvent provided it is used in ordinary coupling reactions, such as those described in "Cross-Coupling Reactions: A Practical Guide (Topics in Current Chemistry)", edited by Norio Miyaura and S. L. Buchwald (editions Springer), or "Metal-Catalyzed Cross-Coupling Reactions", edited by Armin de Meijere and François Diederich (editions WILEY-VCH). This is shown in Scheme 8.

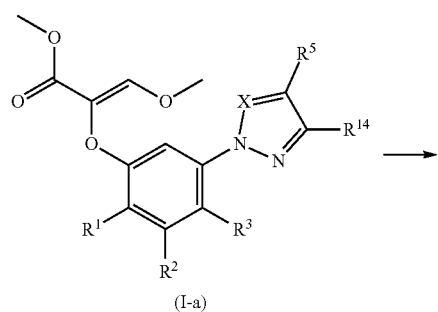

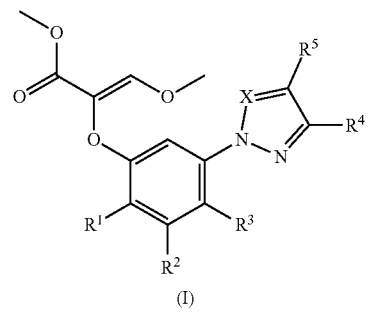

Furthermore, compounds of formula (I), wherein $R^1$, $R^2$, $R^3$, $R^4$ and $R^5$ are as defined above and X is CH, can be prepared from a compound of formula (IIa), wherein $R^1$, $R^2$ and $R^3$ are as defined for compounds of formula (I), via one-pot reaction sequence comprising a diazotization and reduction to the resultant hydrazine salt of formula (X) wherein $R^1$, $R^2$ and $R^3$ are as defined for compounds of formula (I), followed by cyclization with a compound of formula (XI), wherein $R^z$ is hydrogen or $C_1$-$C_4$alkyl and $R^4$ and W are as defined for compounds of formula (I). For related examples, see WO2018/104214. This is shown in Scheme 9.

Scheme 9

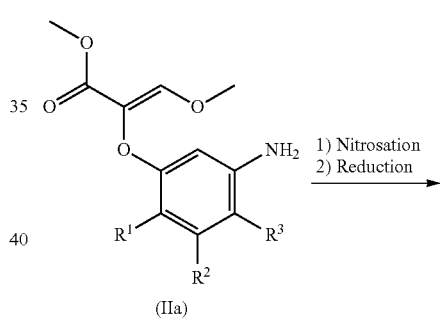

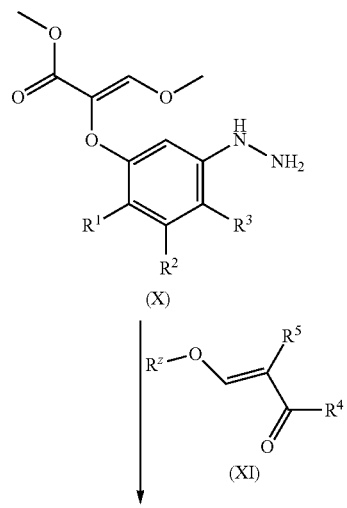

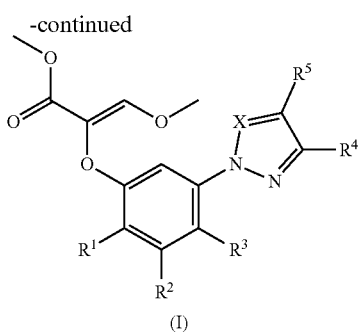

(I)

Alternatively, compounds of formula (XII) can be prepared from compounds of formula (XIII), via nitro group reduction reaction using a metal (e.g. Pd/C, iron, or Raney Nickel) in a suitable solvent (e.g. MeOH or ethanol) in the presence of a reducing agent (e.g. hydrogen gas, ammonium chloride, formic acid, or hydrazine) at a temperature between 25° C. and 65° C. In some cases, an improved reaction performance is gained when an increase in pressure is applied. For related examples, see: Yoshii, Y. et al *Chem. Commun.* (2015), 51, 1070; Takeshiba, H. et al Eur. Pat. Appl., (1997) 807631. The nitro group reduction reaction can be followed by via radical-nucleophilic aromatic substitution reaction (Sandmeyer) in the presence of a nitrite source (eg, $NaNO_2$ or iso-amylnitrite), and a copper source (eg, CuCN) in an acceptable solvent system, such as aqueous acetonitrile, at suitable temperatures (e.g. 0° C. to 100° C.). This reaction is shown in Scheme 10.

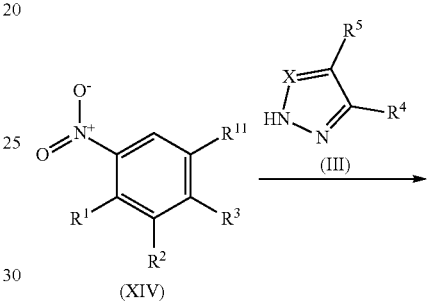

The compounds of formula (XIII) according to the invention, wherein X, $R^1$, $R^2$, $R^3$, $R^4$ and $R^5$ are as defined for formula (I), can be obtained by transformation of a compound of formula (XIV), wherein $R^1$, $R^2$ and $R^3$ are as defined for compounds of formula (I) and $R^{11}$ is halogen (preferably chloro, bromo or iodo), or psuedohalogen (e.g., $—OSO_2CH_3$, $—OSO_2CF_3$ or $—OSO_2(CF_2)_3CF_3$) and compounds of formula (III) wherein X, $R^4$ and $R^5$ are as defined for compounds of formula (I), in the presence of a base such as $K_2CO_3$, a metal compound such as tris(dibenzylideneacetone)dipalladium(0) and optionally with a supporting phosphine ligand such as 2-di-tert-butylphosphino-3,4,5,6-tetramethyl-2',4',6'-triisopropyl-1,1'-biphenyl in an organic solvent such as toluene at temperatures between 20° C.-110° C. Such transformations are described in *Angew. Chem. Int. Ed.* (2011), 8944 and are shown in scheme 11.

Furthermore, compounds of formula (XIII) can be obtained from compounds of formula (XIV) wherein $R^1$, $R^2$ and $R^3$ are as defined for compounds of formula (I) and $R^{11}$ is halogen, and compounds of formula (III) wherein $R^4$ and $R^5$ are as defined for compounds of formula (I), optionally in the presence of a base such as pyridine or $K_2CO_3$ and optionally in the presence copper salt such as $Cu(OAc)_2$ in a suitable inert organic solvent such as dichloromethane. This is shown in scheme 11.

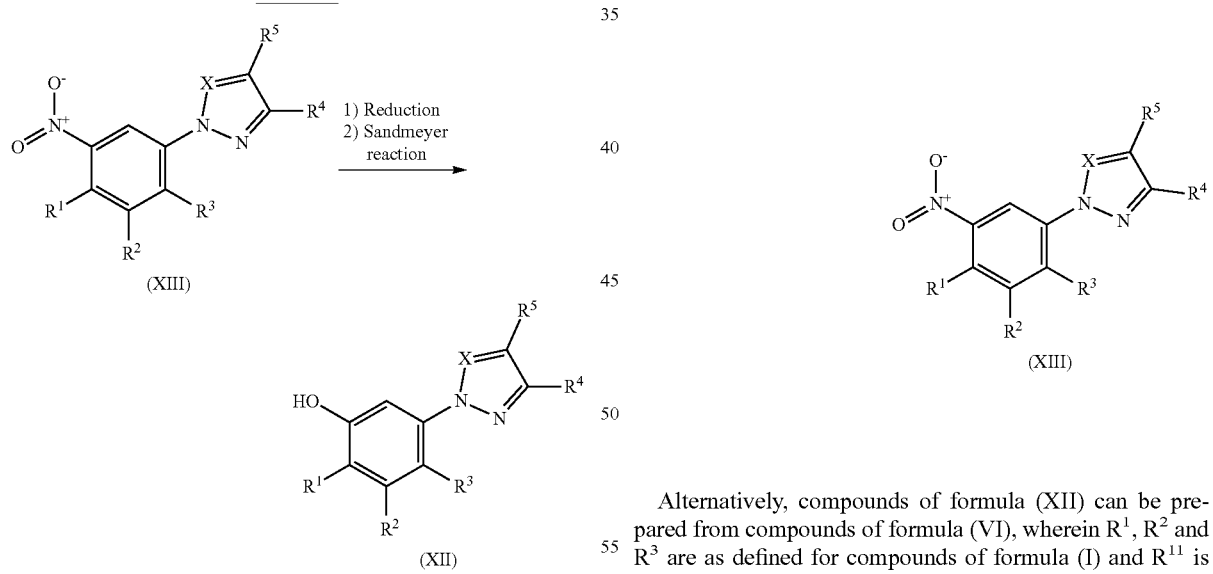

Alternatively, compounds of formula (XII) can be prepared from compounds of formula (VI), wherein $R^1$, $R^2$ and $R^3$ are as defined for compounds of formula (I) and $R^{11}$ is halogen (preferably chloro, bromo or iodo), or psudohalogen (e.g., $—OSO_2CH_3$, $—OSO_2CF_3$ or $—OSO_2(CF_2)_3CF_3$) and compounds of formula (III) wherein X, $R^4$ and $R^5$ are as defined for compounds of formula (I), in the presence of a base (eg, $K_2CO_3$), a copper compound (eg, CuI) and optionally a co-reagent (eg, N,N'-dimethyl-1,2-ethanediamine or N,N'-dimethyl-1,2-cyclohexanediamine) in a suitable organic solvent (eg, toluene or dioxane) at temperatures between 20° C.-150° C. Such transformations are described in *ACS Omega* 2018, 3, 1955 or WO 2013083604 and are shown in the scheme 12.

Scheme 12

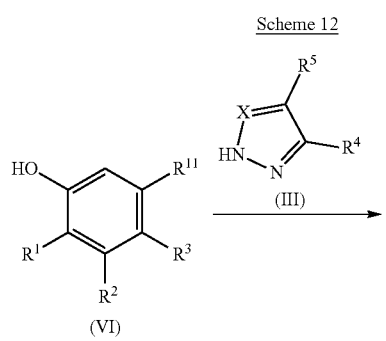

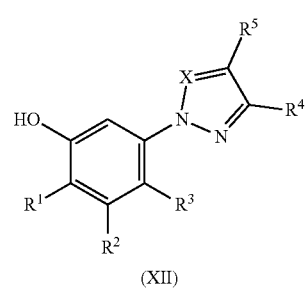

Alternatively, compounds of formula (XIIa) can be prepared from compounds of formula (VIa), wherein $R^1$, $R^2$ and $R^3$ are as defined for compounds of formula (I) and $R^{11}$ is halogen (preferably chloro, bromo or iodo), or psuedohalogen (e.g., —OSO$_2$CH$_3$, —OSO$_2$CF$_3$ or —OSO$_2$(CF$_2$)$_3$CF$_3$) and $R^{15}$ is a suitable protecting group for a phenol function (eg, silyl group, ether group, benzyl) and compounds of formula (III) wherein X, $R^4$ and $R^5$ are as defined for compounds of formula (I), in the presence of a base (eg, K$_2$CO$_3$), a copper compound (eg, CuI) and optionally a co-reagent (eg, N,N'-dimethyl-1,2-ethanediamine or N,N'-dimethyl-1,2-cyclohexanediamine) in a suitable organic solvent (eg, toluene or dioxane) at temperatures between 20° C.-150° C. Such transformations are described in *ACS Omega* 2018, 3, 1955-1969 or WO 2013083604 and are shown in the scheme 13.

Scheme 13

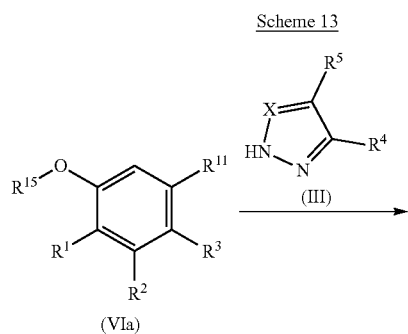

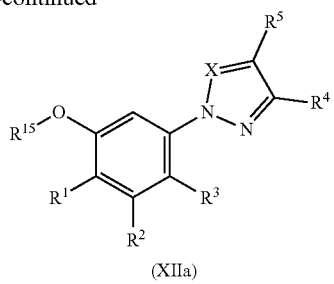

Alternatively, compounds of formula (XVII) can be prepared from compounds of formula (XV), wherein $R^1$, $R^2$ and $R^3$ are as defined for compounds of formula (I) and $R^{13}$ is H or C$_1$-C$_4$ alkyl and $R^{16}$ is as defined in Scheme 14 via nucleophilic aromatic substitution reactions with compound (XVI) in the presence of a nitrite source (eg, NaNO$_2$ or iso-amylnitrite) in acidic conditions (eg, H$_2$SO$_4$ or HBF$_4$) and a copper source (eg, CuSO$_4$ or CuCN) in an acceptable solvent system at suitable temperatures (e.g. 0° C. to 100° C.). Such transformations are described in CN 101580477 or *Journal of Iowa Academy of Science* 2010, 116, 27-35 and are shown in the scheme 14.

Scheme 14

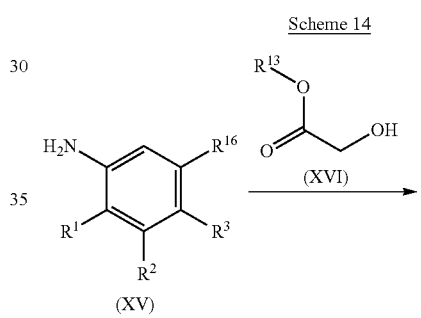

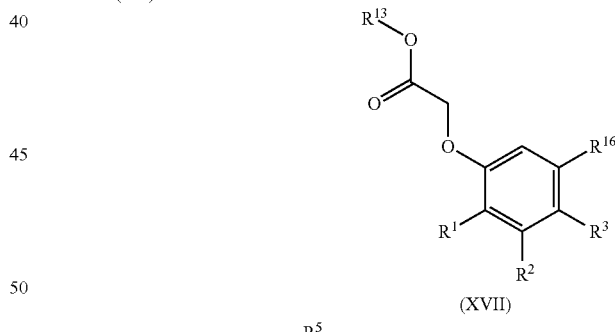

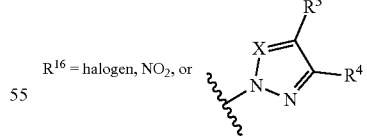

Alternatively, compounds of formula (XVII) can be prepared from compounds of formula (XVIII), wherein X, $R^1$, $R^2$, $R^3$, $R^4$ and $R^5$ are as defined for compounds of formula (I) and $R^{13}$ is H or C$_1$-C$_4$ alkyl and $R^{16}$ is as defined in Scheme 15 via nucleophilic aromatic substitution reactions with compound (XVI) in the presence of a base (eg, Cs$_2$CO$_3$), a catalyst (copper source; eg, CuI or CuO), optionally in the presence of a co-reagent (eg, 1,10-phenanthroline) in an acceptable solvent system (eg, toluene) at suitable temperatures (e.g. 0° C. to 110° C.). Such transformations are described in WO 2007010082 or WO200837626 and are shown in Scheme 15.

Scheme 15

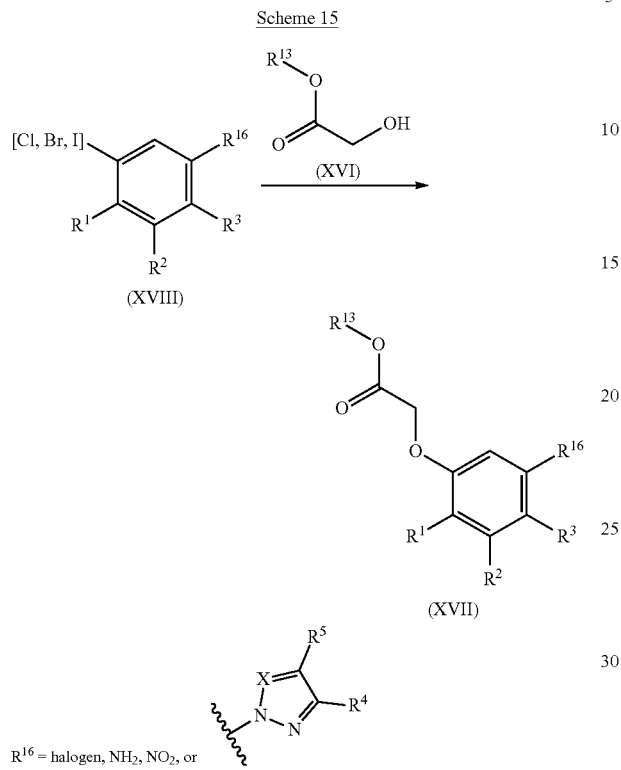

(XVIII)

(XVI)

(XVII)

$R^{16}$ = halogen, $NH_2$, $NO_2$, or

Alternatively, compounds of formula (XVIIc), wherein $R^1$, $R^2$ and $R^3$ are as defined for compounds of formula (I) and $R^{13}$ is H or $C_1$-$C_4$ alkyl, can be obtained from compounds of formula (XIX) wherein $R^1$, $R^2$ and $R^3$ are as defined for compounds of formula (I) by treatment with a base (eg, $Cs_2CO_3$ or $K_2CO_3$) and an alkylation agent of formula (VII), optionally in an organic solvent such as N-methyl pyrrolidone.

Compounds of formula (XX), wherein $R^1$, $R^2$ $R^3$ and $R^{13}$ are as defined above, can be obtained from compounds of formula (XVIIc) via nitro group reduction reaction using a metal (e.g. Pd/C, iron, or Raney Nickel) in a suitable solvent (e.g. MeOH or ethanol) in the presence of a reducing agent (e.g. hydrogen gas, ammonium chloride, formic acid, or hydrazine) at a temperature between 25° C. and 65° C. In some cases, an improved reaction performance is gained when an increase in pressure is applied.
This is shown in scheme 16.

Scheme 16

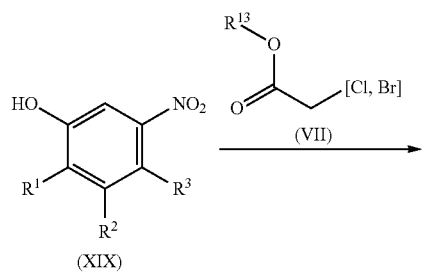

(XIX)

(VII)

-continued

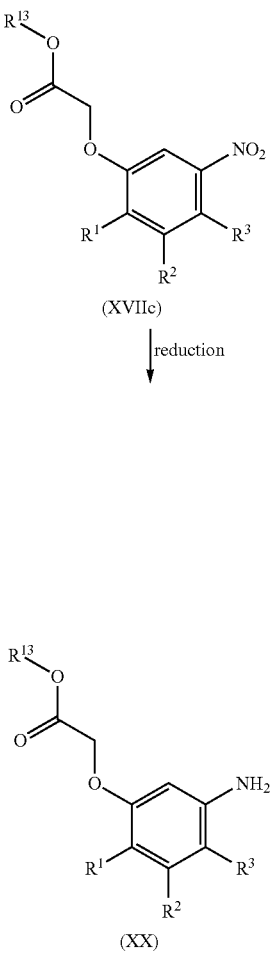

(XVIIc)

reduction (XX)

Alternatively, compounds of formula (XVIIc), wherein $R^1$, $R^2$ and $R^3$ are as defined for compounds of formula (I) and $R^{13}$ is H or $C_1$-$C_4$ alkyl, can be obtained from compounds of formula (XXI) wherein $R^1$, $R^2$ $R^3$ are as defined above and $R^{17}$ is halogen by treatment with compounds of formula (XVI) in the presence of a base (eg, $Cs_2CO_3$), a catalyst (copper source; eg, CuI) in an acceptable solvent system, such as aqueous DMSO, at suitable temperatures (e.g. 0° C. to 120° C.). Such transformations are described by Xiao, Yan et al. in J. Org. Chem. 2013, 78, 5804-5809 and are shown in the scheme 17.

Scheme 17

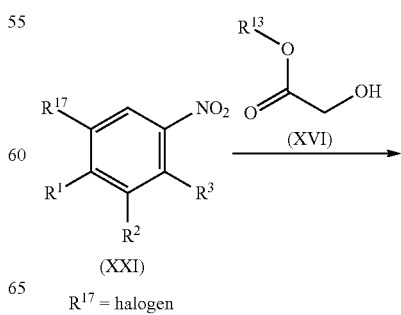

(XXI)

(XVI)

$R^{17}$ = halogen

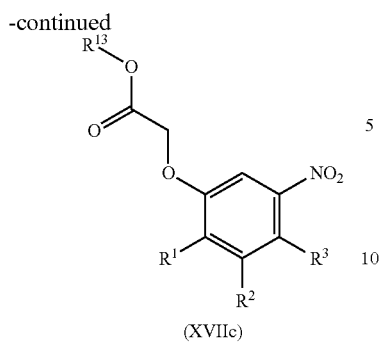

(XVIIc)

Alternatively, compounds of formula (XXIV) wherein $R^1$, $R^2$ and $R^3$ are as defined for compounds of formula (I) and $R^{18}$ is OH, $OR^{15}$, $OR^{19}$, $NO_2$, $NH_2$, $R^{12}$, wherein $R^{15}$ is a suitable protecting group for a phenol function, $R^{19}$ is an optionally substituted $C_1$-$C_4$ alkyl (eg, acetate function) and $R^{12}$ is a diborane species defined in scheme 18, can be obtained from compounds of formula (XXII) wherein $R^1$, $R^2$, $R^3$ and $R^{18}$ are defined above via a sequence comprising a selective reduction of the nitro function to give compounds (XXIII), wherein $R^1$, $R^2$, $R^3$ and $R^{18}$ are defined as above followed by a one-pot reaction sequence comprising a diazotization and a substitution of the corresponding diazonium salt with compounds of formula (III), wherein $R^4$, $R^5$, and X are defined for compounds of formula (I). This sequence is shown in scheme 18.

The nitro group reduction reaction can be performed using a metal (e.g. Pd/C, iron, or Raney Nickel) in a suitable solvent (e.g. MeOH or ethanol) in the presence of a reducing agent (e.g. hydrogen gas, ammonium chloride, formic acid, or hydrazine) at a temperature between 25° C. and 65° C. In some cases, an improved reaction performance is gained when an increase in pressure is applied. For related examples, see: *J. Org. Chem.* 1980, 45, 4992; *Bull. Chem. Soc. Jpn.* 1983, 56, 3159. The reduction reaction can be followed by a one-pot reaction diazotation-substitution reaction in the presence of a nitrite source (eg, $NaNO_2$ or iso-amylnitrite) in acidic conditions (eg, AcOH or $H_2SO_4$), and a copper source (eg, $Cu(OAc)_2$) in an acceptable solvent system, such as methanol, at suitable temperatures (e.g. 0° C. to 100° C.) For related examples, see: *Chem. Eur. J.* 2014, 20, 14619. This sequence is shown in Scheme 18.

Scheme 18

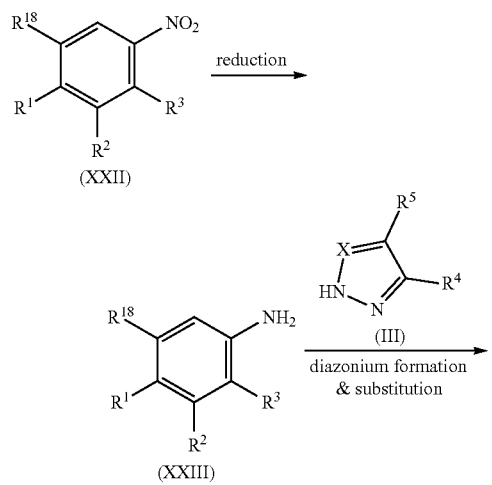

(XXIV)

$R^{18}$ = OH, $OR^{15}$, $OR^{19}$ $NO_2$, $NH_2$, $R^{12}$
$R^{15}$ = phenol protecting group; $R^{19}$ = optionally substituted $C_1$-$C_4$ alkyl

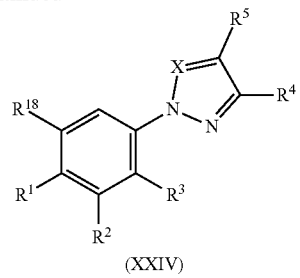

In particular, compounds (XIII), wherein $R^1$, $R^2$, $R^3$, $R^4$, $R^5$ and X are as defined for compounds of formula (I), can be obtained from compounds of formula (XXIIa) wherein $R^1$, $R^2$, $R^3$, $R^4$, $R^5$ and X are as defined for compounds of formula (I) via a sequence comprising a selective reduction of the nitro function to give compounds (XXIIIa) wherein $R^1$, $R^2$ and $R^3$ are as defined for compounds of formula (I) followed by a one-pot reaction sequence comprising a diazotization and a substitution of the corresponding diazonium salt with compounds of formula (III), wherein $R^4$, $R^5$, and X are as defined for compounds of formula (I), as described in scheme 19.

The nitro group reduction reaction can be performed using a metal (e.g. Pd/C, iron, or Raney Nickel) in a suitable solvent (e.g. MeOH or ethanol) in the presence of a reducing agent (e.g. hydrogen gas, ammonium chloride, formic acid, or hydrazine) at a temperature between 25° C. and 65° C. In some cases, an improved reaction performance is gained when an increase in pressure is applied. For related examples, see: *J. Org. Chem.* 1980, 45, 4992; *Bull. Chem. Soc. Jpn.* 1983, 56, 3159. The reduction reaction can be followed by a one-pot reaction diazotation-substitution reaction in the presence of a nitrite source (eg, $NaNO_2$ or iso-amylnitrite) in acidic conditions (eg, AcOH or $H_2SO_4$), and a copper source (eg, $Cu(OAc)_2$) in an acceptable solvent system, such as methanol, at suitable temperatures (e.g. 0° C. to 100° C.) to give compounds (XIII); for related examples, see: *Chem. Eur. J.* 2014, 20, 14619. Compounds of formula (XXV), wherein $R^1$, $R^2$, $R^3$, $R^4$, $R^5$ and X are as defined for compounds of formula (I), can be obtained via reduction of the nitro function of compounds of formula (XIII), wherein $R^1$, $R^2$, $R^3$, $R^4$, $R^5$ and X are as defined for compounds of formula (I). The nitro group reduction reaction can be performed using a metal (e.g. Pd/C, iron, or Raney Nickel) in a suitable solvent (e.g. MeOH or ethanol) in the presence of a reducing agent (e.g. hydrogen gas, ammonium chloride, formic acid, or hydrazine) at a temperature between 25° C. and 65° C. In some cases, an improved reaction performance is gained when an increase in pressure is applied. For related examples, see: *J. Org. Chem.* 1980, 45, 4992; *Bull. Chem. Soc. Jpn.* 1983, 56, 3159. This sequence is shown in Scheme 19.

Scheme 19

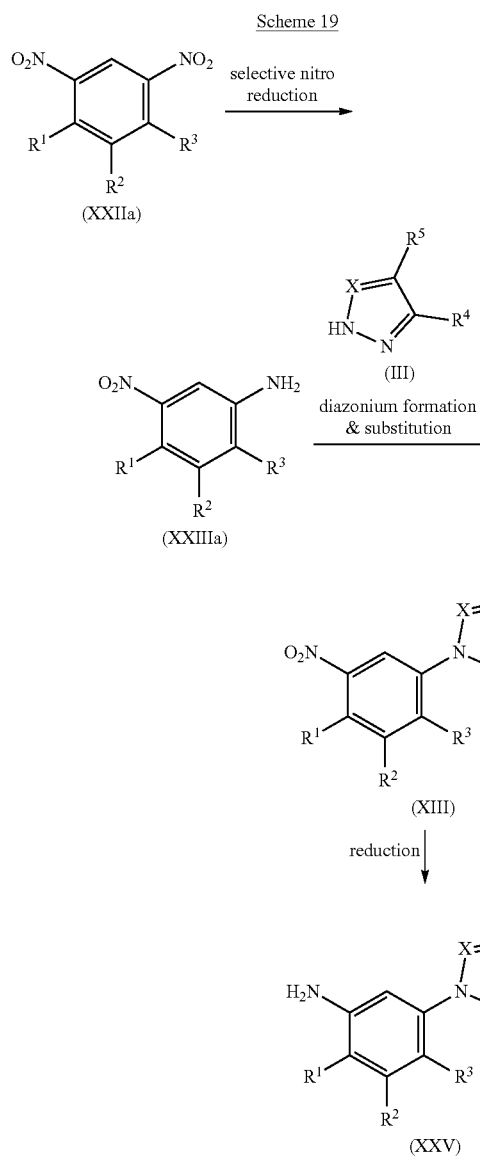

Scheme 20

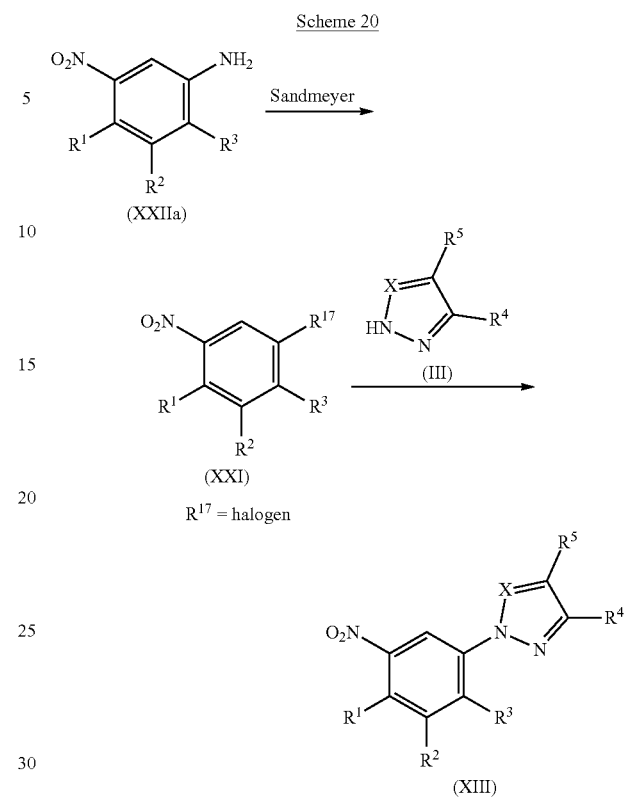

Alternatively, compounds of formula (XIII), wherein $R^1$, $R^2$, $R^3$, $R^4$, $R^5$ and X are as defined for compounds of formula (I), can be obtained from compounds of formula (XXIIIa) wherein $R^1$, $R^2$ and $R^3$ are as defined for compounds of formula (I) via a sequence comprising a Sandmeyer reaction, in the presence of a nitrite source (eg, $NaNO_2$ or iso-amylnitrite), and a copper source (eg, CuBr) in an acceptable solvent system, such as aqueous acetonitrile, at suitable temperatures (e.g. 0° C. to 100° C.), to give compounds of formula (XXI) wherein $R^1$, $R^2$, $R^3$ are as defined for compounds of formula (I) and $R^{17}$ is a halogen followed by a substitution with compounds of formula (III), wherein $R^4$, $R^5$, and X are as defined for compounds of formula (I), in the presence of a copper source (eg, CuO or CuI) as a catalyst and ligands (eg, oxime derived, bi-, tri-, tetra-dentate derived ligands) in an acceptable solvent system, such as acetonitrile, at suitable temperatures (e.g. 0° C. to 82° C.) as reported by Taillefer, M. et al. in Eur. J. Org. Chem. 2004, 4, 695-709. This sequence is shown in Scheme 20.

Alternatively, compounds of formula (XXVII) wherein $R^1$, $R^2$ and $R^3$ are as defined for compounds of formula (I) can be obtained from compounds of formula (XXVI) wherein $R^1$, $R^2$ and $R^3$ are as defined for compounds of formula (I) and $R^{12}$ is as defined in scheme 21, in the presence of an oxidant (eg, $H_2O_2$, $O_2$) in aqueous media at suitable temperatures (e.g. 20° C. to 100° C.). For related examples, see: Luo, D. P. et al. in Adv. Synth. Cat. 2019, 361, 961-964. This reaction is shown in Scheme 21.

Scheme 21

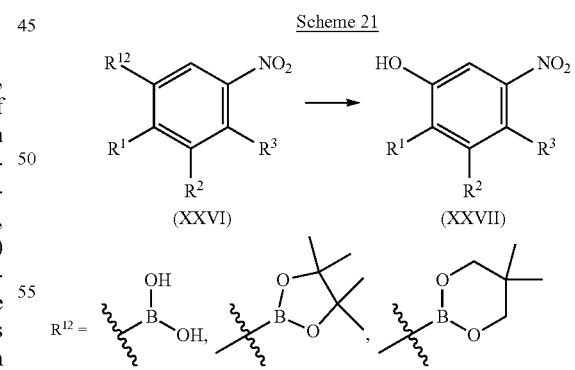

Alternatively, compounds of formula (XXIX), wherein $R^1$, $R^2$ and $R^3$ are as defined for compounds of formula (I) and $R^{16}$ is defined as in scheme 22, can be prepared from compounds of formula (XXVIII), wherein $R^1$, $R^2$ and $R^3$ are as defined for compounds of formula (I) and $R^{16}$ is defined as in scheme 22, via nitro group reduction reaction using a metal (e.g. Pd/C, iron, or Raney Nickel) in a suitable solvent (e.g. MeOH or ethanol) in the presence of a reducing agent (e.g. hydrogen gas, ammonium chloride, formic acid, or hydrazine) at a temperature between 25° C. and 65° C. In some cases, an improved reaction performance is gained when an increase in pressure is applied. For related examples, see: Yoshii, Y. et al Chem. Commun. 2015, 51, 1070; Takeshiba, H. et al Eur. Pat. Appl., (1997) 807631. The reduction reaction can be followed by a Sandmeyer reaction in the presence of a nitrite source (eg, $NaNO_2$ or iso-amylnitrite), and a copper source (eg, CuCN) in an acceptable solvent system, such as aqueous acetonitrile, at suitable temperatures (e.g. 0° C. to 100° C.). This reaction is shown in Scheme 22.

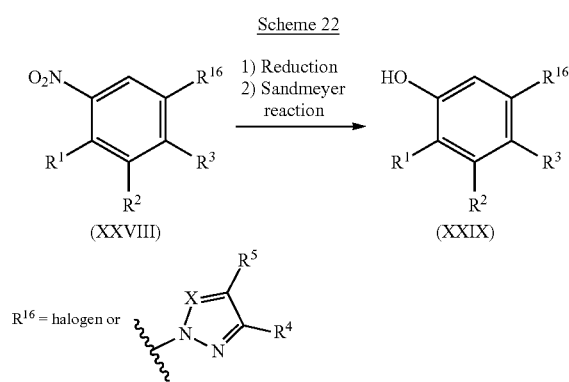

Alternatively, compounds of formula (I) wherein X, $R^1$, $R^2$, $R^3$, $R^4$ and $R^5$ are as defined above, can be obtained by transformation of another, closely related, compound of formula I (or an analogue thereof) using standard synthesis techniques known to the person skilled in the art. Non-exhaustive examples include oxidation reactions, reduction reactions, hydrogenation reactions, hydrolysis reactions, coupling reactions, aromatic nucleophilic or electrophilic substitution reactions, nucleophilic substitution reactions, alkylation reactions, nucleophilic addition reactions and halogenation reactions.

Functional group interconversions as described in the previous schemes are known to the persons skilled in the art. Extensive lists of reaction conditions can be found in: *Comprehensive Organic Functional Group Transformations*, Edited by A. R. Katritzky, O. Meth-Cohn and C. W. Rees. Pergamon Press (Elsevier Science Ltd.), Tarrytown, NY. 1995; or in: *Comprehensive Organic Transformations: A Guide to Functional Group Preparations*, Edited by Richard C. Larock, Wiley-VCH, New York 1999.

If the synthesis yields mixtures of isomers, a separation is generally not necessarily required because in some cases the individual isomers can be interconverted during work-up for use or during application (e. g. under the action of light, acids or bases). Such conversions may also take place after use, e. g. in the treatment of plants in the treated plant, or in the harmful fungus to be controlled.

As already indicated, it has now been found that the novel compounds of Formula (I) of the present invention have a very advantageous level of biological activity for protecting plants against diseases that are caused by fungi.

The compounds of formula (I) can be used in the agricultural sector and related fields of use, e.g., as active ingredients for controlling plant pests or on non-living materials for the control of spoilage microorganisms or organisms potentially harmful to man. The novel compounds are distinguished by excellent activity at low rates of application, by being well tolerated by plants and by being environmentally safe. They have very useful curative, preventive and systemic properties and can be used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The present invention further relates to a method for controlling or preventing infestation of plants or plant propagation material and/or harvested food crops susceptible to microbial attack by treating plants or plant propagation material and/or harvested food crops wherein an effective amount a compound of formula (I) is applied to the plants, to parts thereof or the locus thereof.

It is also possible to use compounds of formula (I) as fungicide. The term "fungicide" as used herein means a compound that controls, modifies, or prevents the growth of fungi. The term "fungicidally effective amount" where used means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It may also be possible to use compounds of formula (I) as dressing agents for the treatment of plant propagation material, e.g., seed, such as fruits, tubers or grains, or plant cuttings, for the protection against fungal infections as well as against phytopathogenic fungi occurring in the soil. The propagation material can be treated with a composition comprising a compound of formula (I) before planting: seed, for example, can be dressed before being sown. The active compounds of formula (I) can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore, the compounds of formula (I) can be used for controlling fungi in related areas, for example in the protection of technical materials, including wood and wood related products, in food storage, in hygiene management.

In addition, the invention could be used to protect non-living materials from fungal attack, e.g. lumber, wall boards and paint.

The compounds of formula (I) are for example, effective against fungi and fungal vectors of disease as well as phytopathogenic bacteria and viruses. These fungi and fungal vectors of disease as well as phytopathogenic bacteria and viruses are for example: *Absidia corymbifera*, *Alternaria* spp, *Aphanomyces* spp, *Ascochyta* spp, *Aspergillus* spp. including *A. flavus*, *A. fumigatus*, *A. nidulans*, *A. niger*, *A. terrus*, *Aureobasidium* spp. including *A. pullulans*, *Blastomyces dermatitidis*, *Blumeria graminis*, *Bremia lactucae*, *Botryosphaeria* spp. including *B. dothidea*, *B. obtusa*, *Botrytis* spp. including *B. cinerea*, *Candida* spp. including *C. albicans*, *C. glabrata*, *C. krusei*, *C. lusitaniae*, *C. parapsilosis*, *C. tropicalis*, *Cephaloascus fragrans*, *Ceratocystis* spp, *Cercospora* spp. including *C. arachidicola*, *Cercosporidium personatum*, *Cladosporium* spp, *Claviceps purpurea*, *Coccidioides immitis*, *Cochliobolus* spp, *Colletotrichum* spp. including *C. musae, Cryptococcus neoformans, Diaporthe* spp, *Didymella* spp, *Drechslera* spp, *Elsinoe* spp, *Epidermophyton* spp, *Erwinia amylovora, Erysiphe* spp. including *E. cichoracearum, Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. digitatum, P. italicum, Petriellidium* spp, *Peronosclerospora* spp. Including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedii, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. triticina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi, Sclerotinia* spp, *Sclerotium* spp, *Septoria* spp, including *S. nodorum, S. tritici, Sphaerotheca macularis, Sphaerotheca fusca (Sphaerotheca fuliginea), Sporothorix* spp, *Stagonospora nodorum, Stemphylium* spp., *Stereum hirsutum, Thanatephorus cucumeris, Thielaviopsis basicola, Tilletia* spp, *Trichoderma* spp. including *T. harzianum, T. pseudokoningii, T. viride, Trichophyton* spp, *Typhula* spp, *Uncinula necator, Urocystis* spp, *Ustilago* spp, *Venturia* spp. including *V. inaequalis, Verticillium* spp, and *Xanthomonas* spp.

The compounds of formula (I) may be used for example on turf, ornamentals, such as flowers, shrubs, broad-leaved trees or evergreens, for example conifers, as well as for tree injection, pest management and the like.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as also including useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as also including useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyltransferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

Further, in the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO93/07278, WO95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The compounds of formula (I) (including any one of compounds E-1 to E-118 or F-1 to F-13) or fungicidal compositions according to the present invention comprising a compound of formula (I) may be used in controlling or preventing phytopathogenic diseases, especially phytopathogenic fungi (such as *Phakopsora pachyrhizi*) on soy bean plants.

In particular, transgenic soybean plants expressing toxins, for example insecticidal proteins such as delta-endotoxins, e.g. Cry1Ac (Cry1Ac Bt protein). Accordingly, this may include transgenic soybean plants comprising event MON87701 (see U.S. Pat. No. 8,049,071 and related applications and patents, as well as WO 2014/170327 A1 (eg, see paragraph [008] reference to Intacta RR2 PRO™ soybean)), event MON87751 (US. Patent Application Publication No. 2014/0373191) or event DAS-81419 (U.S. Pat. No. 8,632, 978 and related applications and patents).

Other transgenic soybean plants may comprise event SYHT0H2-HPPD tolerance (U.S. Patent Application Publication No. 2014/0201860 and related applications and patents), event MON89788-glyphosate tolerance (U.S. Pat. No. 7,632,985 and related applications and patents), event MON87708-dicamba tolerance (U.S. Patent Application Publication No. US 2011/0067134 and related applications and patents), event DP-356043-5-glyphosate and ALS tolerance (U.S. Patent Application Publication No. US 2010/0184079 and related applications and patents), event A2704-

12-glufosinate tolerance (U.S. Patent Application Publication No. US 2008/0320616 and related applications and patents), event DP-305423-1-ALS tolerance (U.S. Patent Application Publication No. US 2008/0312082 and related applications and patents), event A5547-127-glufosinate tolerance (U.S. Patent Application Publication No. US 2008/0196127 and related applications and patents), event DAS-40278-9-tolerance to 2,4-dichlorophenoxyacetic acid and aryloxyphenoxypropionate (see WO 2011/022469, WO 2011/022470, WO 2011/022471, and related applications and patents), event 127-ALS tolerance (WO 2010/080829 and related applications and patents), event GTS 40-3-2-glyphosate tolerance, event DAS-68416-4-2,4-dichlorophenoxyacetic acid and glufosinate tolerance, event FG72-glyphosate and isoxaflutole tolerance, event BPS-CV127-9-ALS tolerance and GU262-glufosinate tolerance or event SYHT04R-HPPD tolerance.

The compounds of formula (I) (including any one of compounds E-1 to E-118 or F-1 to F-13) or fungicidal compositions according to the present invention comprising a compound of formula (I) may be used in controlling or preventing phytopathogenic diseases, especially phytopathogenic fungi (such as *Phakopsora pachyrhizi*) on soy bean plants. In particular, there are known in the scientific literature certain Elite soybean plant varieties where R-gene stacks, conferring a degree of immunity or resistance to specific *Phakopsora pachyrhizi*, have been introgressed in the plant genome, see for example: "*Fighting Asian Soybean Rust*", Langenbach C, et al, *Front Plant Science* 7(797) 2016).

An elite plant is any plant from an elite line, such that an elite plant is a representative plant from an elite variety. Non-limiting examples of elite soybean varieties that are commercially available to farmers or soybean breeders include: AG00802, A0868, AG0902, A1923, AG2403, A2824, A3704, A4324, A5404, AG5903, AG6202 AG0934; AG1435; AG2031; AG2035; AG2433; AG2733; AG2933; AG3334; AG3832; AG4135; AG4632; AG4934; AG5831; AG6534; and AG7231 (Asgrow Seeds, Des Moines, Iowa, USA); BPR0144RR, BPR 4077NRR and BPR 4390NRR (Bio Plant Research, Camp Point, Ill., USA); DKB17-51 and DKB37-51 (DeKalb Genetics, DeKalb, Ill., USA); DP 4546 RR, and DP 7870 RR (Delta & Pine Land Company, Lubbock, Tex., USA); JG 03R501, JG 32R606C ADD and JG 55R503C (JGL Inc., Greencastle, Ind., USA); NKS 13-$K_2$ (NK Division of Syngenta Seeds, Golden Valley, Minn., USA); 90M01, 91M30, 92M33, 93M11, 94M30, 95M30, 97652, P008T22R2; P16T17R2; P22T69R; P25T51R; P34T07R2; P35T58R; P39T67R; P47T36R; P46T21R; and P56T03R2 (Pioneer Hi-Bred International, Johnston, Iowa, USA); SG4771NRR and SG5161NRR/STS (Soygenetics, LLC, Lafayette, Ind., USA); S00-$K_5$, S11-L2, S28-Y2, S43-B1, S53-A1, S76-L9, S78-G6, S0009-M2; S007-Y4; S04-D3; S14-A6; S20-T6; S21-M7; S26-P3; S28-N6; S30-V6; S35-C3; S36-Y6; S39-C4; S47-$K_5$; S48-D9; S52-Y2; S58-Z4; S67-R6; S73-S8; and S78-G6 (Syngenta Seeds, Henderson, Ky., USA); Richer (Northstar Seed Ltd. Alberta, CA); 14RD62 (Stine Seed Co. la., USA); or Armor 4744 (Armor Seed, LLC, Ar., USA).

Thus, in a further preferred embodiment, the compounds of Formula (I) (including any one of compounds E-1 to E-118 or F-1 to F-13), or fungicidal compositions according to the present invention comprising a compound of formula (I), are used to control *Phakopsora pachyrhizi*, (including fungicidally-resistant strains thereof, as outlined herein) on Elite soybean plant varieties where R-gene stacks, conferring a degree of immunity or resistance to specific *Phakopsora pachyrhizi*, have been introgressed in the plant genome. Numerous benefits may be expected to ensue from said use, e.g. improved biological activity, an advantageous or broader spectrum of activity (inc. sensitive and resistant strains of *Phakopsora pachyrhizi*), an increased safety profile, improved crop tolerance, synergistic interactions or potentiating properties, improved onset of action or a longer lasting residual activity, a reduction in the number of applications and/or a reduction in the application rate of the compounds and compositions required for effective control of the phytopathogen (*Phakopsora pachyrhizi*), thereby enabling beneficial resistance-management practices, reduced environmental impact and reduced operator exposure.

Fungicidal-resistant strains of *Phakopsora pachyrhizi* have been reported in the scientific literature, with strains resistant to one or more fungicides from at least each of the following fungicidal mode of action classes being observed: sterol demethylation-inhibitors (DMI), quinone-outside-inhibitors (QoI) and succinate dehydrogenase inhibitors (SDHI). See for example: "Sensitivity of *Phakopsora pachyrhizi* towards quinone-outside-inhibitors and demethylation-inhibitors, and corresponding resistance mechanisms." Schmitz H K et al, *Pest Manag Sci* (2014) 70: 378-388; "First detection of a SDH variant with reduced SDHI sensitivity in *Phakopsora pachyrhizi*" Simões K et al, *J Plant Dis Prot* (2018) 125: 21-2; "Competitive fitness of *Phakopsora pachyrhizi* isolates with mutations in the CYP51 and CYTB genes." Klosowski A C et al, *Phytopathology* (2016) 106: 1278-1284; "Detection of the F129L mutation in the cytochrome b gene in *Phakopsora pachyrhizi*." Klosowski A C et al, *Pest Manag Sci* (2016) 72: 1211-1215.

Thus, in a preferred embodiment, the compounds of Formula (I) (including any one of compounds E-1 to E-118 or F-1 to F-13), or fungicidal compositions according to the present invention comprising a compound of formula (I), are used to control *Phakopsora pachyrhizi* which are resistant to one or more fungicides from any of the following fungicidal MoA classes: sterol demethylation-inhibitors (DMI), quinone-outside-inhibitors (QoI) and succinate dehydrogenase inhibitors (SDHI).

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There can be mentioned for example seeds (in the strict sense), roots, fruits, tubers, bulbs, rhizomes and parts of plants. Germinated plants and young plants which are to be transplanted after germination or after emergence from the soil, may also be mentioned. These young plants can be protected before transplantation by a total or partial treatment by immersion. Preferably "plant propagation material" is understood to denote seeds.

The compounds of formula I may be used in unmodified form or, preferably, together with the adjuvants conventionally employed in the art of formulation. To this end they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which treatment is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art.

Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants and sticking agents.

In addition, further, other biocidally active ingredients or compositions may be combined with the compositions of the invention and used in the methods of the invention and applied simultaneously or sequentially with the compositions of the invention. When applied simultaneously, these further active ingredients may be formulated together with the compositions of the invention or mixed in, for example, the spray tank. These further biocidally active ingredients may be fungicides, herbicides, insecticides, bactericides, acaricides, nematicides and/or plant growth regulators.

Pesticidal agents are referred to herein using their common name are known, for example, from "The Pesticide Manual", 15th Ed., British Crop Protection Council 2009.

In addition, the compositions of the invention may also be applied with one or more systemically acquired resistance inducers ("SAR" inducer). SAR inducers are known and described in, for example, U.S. Pat. No. 6,919,298 and include, for example, salicylates and the commercial SAR inducer acibenzolar-S-methyl.

The compounds of formula (I) are normally used in the form of agrochemical compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as defined herein, in free form or in agrochemically usable salt form, and at least one of the above-mentioned adjuvants.

The invention therefore provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably said composition may comprise at least one or more pesticidally-active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate.

Examples of suitable additional active ingredients include the following: acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, and zinc fungicides.

Examples of suitable additional active ingredients also include the following: 3-difluoromethyl-1-methyl-1H-pyrazole-4-carboxylic acid (9-dichloromethylene-1,2,3,4-tetrahydro-1,4-methano-naphthalen-5-yl)-amide, 3-difluoromethyl-1-methyl-1H-pyrazole-4-carboxylic acid methoxy-[1-methyl-2-(2,4,6-trichlorophenyl)-ethyl]-amide, 1-methyl-3-difluoromethyl-1H-pyrazole-4-carboxylic acid (2-dichloromethylene-3-ethyl-1-methyl-indan-4-yl)-amide (1072957-71-1), 1-methyl-3-difluoromethyl-1H-pyrazole-4-carboxylic acid (4'-methylsulfanyl-biphenyl-2-yl)-amide, 1-methyl-3-difluoromethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichloro-phenyl)-1-methyl-prop-2-en-(E)-ylideneaminooxymethyl]-phenyl}-2-[(Z)-methoxyimino]-N-methyl-acetamide, 3-[5-(4-Chloro-phenyl)-2,3-dimethyl-isoxazolidin-3-yl]-pyridine, (E)-N-methyl-2-[2-(2,5-dimethylphenoxymethyl) phenyl]-2-methoxy-iminoacetamide, 4-bromo-2-cyano-N, N-dimethyl-6-trifluoromethylbenzimidazole-1-sulphonamide, a-[N-(3-chloro-2,6-xylyl)-2-methoxyacetamido]-y- butyrolactone, 4-chloro-2-cyano-N,N-dimethyl-5-p-tolylimidazole-1-sulfonamide, N-allyl-4,5,-dimethyl-2-trimethylsilylthiophene-3-carboxamide, N-(I-cyano-1,2-dimethylpropyl)-2-(2,4-dichlorophenoxy) propionamide, N-(2-methoxy-5-pyridyl)-cyclopropane carboxamide, (.+−.)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one, methyl (E)-2-[2-[6-(2-cyanophenoxy)pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy)pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-m ethylpyrimidin-2-yloxy)-phenoxy]phenyl]-3-methoxyacrylate, methyl (E)-2-[2-[3-(phenyl-sulphonyloxy)phenoxy]phenyl-3-methoxyacrylate, methyl (E)-2-[2-(3-nitrophenoxy)phenoxy]phenyl]-3-methoxyacrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenoxy)phenyl]-3-methoxyacrylate, methyl (E)-2[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy)phenyl]-3-methoxyacrylate, methyl (E)-2-[2-[3-(2-fluoro-phenoxy)phenoxy]phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy]phenyl]-3-methoxyacrylate, methyl (E)-2-[2-[(3-methyl-pyridin-2-yloxymethyl)phenyl]-3-methoxyacrylate, methyl (E)-2-[2-[6-(2-methyl-phenoxy)pyrimidin-4-yloxy]phenyl]-3-methoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-dimethylpyrazin-2-ylmethyloximinomethyl)phenyl]-3-methoxyacrylate, methyl (E)-2-{2-[6-(6-methylpyridin-2-yloxy)pyrimidin-4-yloxy]phenyl}-3-methoxy-acrylate, methyl (E),(E)-2-{2-(3-methoxyphenyl)methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy]phenyl}-3-methoxyacrylate, methyl (E),(E)-2-{2-[(3-nitrophenyl)methyloximinomethyl]phenyl}-3-methoxyacrylate, 3-chloro-7-(2-aza-2,7,7-trimethyl-oct-3-en-5-ine), 2,6-dichloro-N-(4-trifluoromethylbenzyl)-benzamide, 3-iodo-2-propynyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propynyl n-butylcarbamate, 3-iodo-2-propynyl n-hexylcarbamate, 3-iodo-2-propynyl cyclohexyl-carbamate, 3-iodo-2-propynyl phenylcarbamate; phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 5-hydroxy-2 (5H)-furanone; 4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, acibenzolar, acypetacs, alanycarb, albendazole, aldimorph, allicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, benzovindiflupyr, berberine, bethoxazin, biloxazol, binapacryl, biphenyl, bitertanol, bithionol, bixafen, blasticidin-S, boscalid, bromothalonil, bromuconazole, bupirimate, buthiobate, butylamine calcium polysulfide, captafol, captan, carbamorph, carbendazim, carbendazim chlorhydrate, carboxin, carpropamid, carvone, CGA41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymoxanil, cypendazole, cyproconazole, cyprodinil, dazomet, debacarb, decafentin, dehydroacetic acid, di-2-pyridyl disulphide 1,1'-dioxide, dichlofluanid, diclomezine, dichlone, dicloran, dichlorophen, dichlozoline, diclobutrazol, diclocymet, diethofencarb, difenoconazole, difenzoquat, diflumetorim, O, O-di-iso-propyl-S-benzyl thiophosphate, dimefluazole, dimetachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)—N-benzyl-N([methyl (methyl-thioethylideneamino-oxycarbonyl) amino] thio)-ß-alaninate, etridiazole, famoxadone, fenamidone, fenaminosulf, fenapanil, fenarimol, fenbuconazole, fenfuram, fenhexamid, fenitropan, fenoxanil, fenpiclonil, fenpicoxamid, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, fluotrimazole, fluoxastrobin, fluquinconazole, flusilazole, flusulfamide, flutanil, flutolanil, flutriafol, fluxapyroxad, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexa chlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, ipfentrifluconazole, iprobenfos, iprodione, iprovalicarb, isopropanyl butyl carbamate, isoprothiolane, isopyrazam, isotianil, isovaledione, izopamfos, kasugamycin, kresoximmethyl, LY186054, LY211795, LY248908, mancozeb, mandipropamid, maneb, mebenil, mecarbinzid, mefenoxam, mefentrifluconazole, mepanipyrim, mepronil, mercuric chloride, mercurous chloride, meptyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-isopropyl, nuarimol, octhilinone, ofurace, organomercury compounds, orysastrobin, osthol, oxadixyl, oxasulfuron, oxathiapiprolin, oxine-copper, oxolinic acid, oxpoconazole, oxycarboxin, paclobutrazol, parinol, pefurazoate, penconazole, pencycuron, penflufen, pentachlorophenol, penthiopyrad, phenamacril, phenazin oxide, phosdiphen, phosetyl-Al, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pydiflumetofen, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, spiroxamine, streptomycin, sulphur, sultropen, tebuconazole, tebfloquin, tecloftalam, tecnazene, tecoram, tetraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolclofos-methyl, tolylfluanid, triadimefon, triadimenol, triamiphos, triarimol, triazbutil, triazoxide, tricyclazole, tridemorph, trifloxystrobin, triflumazole, triforine, triflumizole, triticonazole, uniconazole, urbacide, validamycin, valifenalate, vapam, vinclozolin, zarilamid, zineb, ziram, and zoxamide.

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO 96/15121 and also with anthelmintic active cyclic depsipeptides such as those described in WO 96/11945, WO 93/19053, WO 93/25543, EP 0 626 375, EP 0 382 173, WO 94/19334, EP 0 382 173, and EP 0 503 538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO 95/19363 or WO 04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai*, *kurstaki*, *Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

Thus, compounds of formula (I) can be used in combination with one or more other active ingredients to provide various fungicidal mixtures. Specific examples of such mixtures include (wherein "I" represents a compound of formula (I)): a compound selected from the group of substances consisting of petroleum oils+I, 1,1-bis(4-chlorophenyl)-2-ethoxyethanol+I, 2,4-dichlorophenyl benzenesulfonate+I, 2-fluoro-N-methyl-N-1-naphthylacetamide+I, 4-chlorophenyl phenyl sulfone+I, acetoprole+I, aldoxycarb+I, amidithion+I, amidothioate+I, amiton+I, amiton hydrogen oxalate+I, amitraz+I, aramite+I, arsenous oxide+I, azobenzene+I, azothoate+I, benomyl+I, benoxafos+I, benzyl benzoate+I, bixafen+I, brofenvalerate+I, bromocyclen+I, bromophos+I, bromopropylate+I, buprofezin+I, butocarboxim+I, butoxycarboxim+I, butylpyridaben+I, calcium polysulfide+I, camphechlor+I, carbanolate+I, carbophenothion+I, cymiazole+I, chinomethionat+I, chlorbenside+I, chlordimeform+I, chlordimeform hydrochloride+I, chlorfenethol+I, chlorfenson+I, chlorfensulfide+I, chlorobenzilate+I, chloromebuform+I, chloromethiuron+I, chloropropylate+I, chlorthiophos+I, cinerin I+I, cinerin II+I, cinerins+I, closantel+I, coumaphos+I, crotamiton+I, crotoxyphos+I, cufraneb+I, cyanthoate+I, DCPM+I, DDT+I, demephion+I, demephion-O+I, demephion-S+I, demeton-methyl+I, demeton-O+I, demeton-O-methyl+I, demeton-S+I, demeton-S-methyl+I, demeton-S-methylsulfon+I, dichlofluanid+I, dichlorvos+I, dicliphos+I, dienochlor+I, dimefox+I, dinex+I, dinex-diclexine+I, dinocap-4+I, dinocap-6+I, dinocton+I, dinopenton+I, dinosulfon+I, dinoterbon+I, dioxathion+I, diphenyl sulfone+I, disulfiram+I, DNOC+I, dofenapyn+I, doramectin+I, endothion+I, eprinomectin+I, ethoate-methyl+I, etrimfos+I, fenazaflor+I, fenbutatin oxide+I, fenothiocarb+I, fenpyrad+I, fenpyroximate+I, fenpyrazamine+I, fenson+I, fentrifanil+I, flubenzimine+I, flucycloxuron+I, fluenetil+I, fluorbenside+I, FMC 1137+I, formetanate+I, formetanate hydrochloride+I, formparanate+I, gamma-HCH+I, glyodin+I, halfenprox+I, hexadecyl cyclopropanecarboxylate+I, isocarbophos+I, jasmolin I+I, jasmolin II+I, jodfenphos+I, lindane+I, malonoben+I, mecarbam+I, mephosfolan+I, mesulfen+I, methacrifos+I, methyl bromide+I, metolcarb+I, mexacarbate+I, milbemycin oxime+I, mipafox+I, monocrotophos+I, morphothion+I, moxidectin+I, naled+I, 4-chloro-2-(2-chloro-2-methyl-propyl)-5-[(6-iodo-3-pyridyl)methoxy]pyridazin-3-one+I, niflurididde+I, nikkomycins+I, nitrilacarb+I, nitrilacarb 1:1 zinc chloride complex+I, omethoate+I, oxydeprofos+I, oxydisulfoton+I, pp'-DDT+I, parathion+I, permethrin+I, phenkapton+I, phosalone+I, phosfolan+I, phosphamidon+I, polychloroterpenes+I, polynactins+I, proclonol+I, promacyl+I, propoxur+I, prothidathion+I, prothoate+I, pyrethrin I+I, pyrethrin II+I, pyrethrins+I, pyridaphenthion+I, pyrimitate+I, quinalphos+I, quintiofos+I, R-1492+I, phosglycin+I, rotenone+I, schradan+I, sebufos+I, selamectin+I, sophamide+I, SSI-121+I, sulfiram+I, sulfluramid+I, sulfotep+I, sulfur+I, diflovidazin+I, tau-fluvalinate+I, TEPP+I, terbam+I, tetradifon+I, tetrasul+I, thiafenox+I, thiocarboxime+I, thiofanox+I, thiometon+I, thioquinox+I, thuringiensin+I, triamiphos+I, triarathene+I, triazophos+I, triazuron+I, trifenofos+I, trinactin+I, vamidothion+I, vaniliprole+I, bethoxazin+I, copper dioctanoate+I, copper sulfate+I, cybutryne+I, dichlone+I, dichlorophen+I, endothal+I, fentin+I, hydrated lime+I, nabam+I, quinoclamine+I, quinonamid+I, simazine+I, triphenyltin acetate+I, triphenyltin hydroxide+I, crufomate+I, piperazine+I, thiophanate+I, chloralose+I, fenthion+I, pyridin-4-amine+I, strychnine+I, 1-hydroxy-1H-pyridine-2-thione+I, 4-(quinoxalin-2-ylamino)benzenesulfonamide+I, 8-hydroxyquinoline sulfate+I, bronopol+I, copper hydroxide+I, cresol+I, dipyrithione+I, dodicin+I, fenaminosulf+I, formaldehyde+I, hydrargaphen+I, kasugamycin+I, kasugamycin hydrochloride hydrate+I, nickel bis(dimethyldithiocarbamate)+I, nitrapyrin+I, octhilinone+I, oxolinic acid+I, oxytetracycline+I, potassium hydroxyquinoline sulfate+I, probenazole+I, streptomycin+I, streptomycin sesquisulfate+I, tecloftalam+I, thiomersal+I, *Adoxophyes orana* GV+I, *Agrobacterium radiobacter*+I, *Amblyseius* spp.+I, *Anagrapha falcifera* NPV+I, *Anagrus atomus*+I, *Aphelinus abdominalis*+I, *Aphidius colemani*+I, *Aphidoletes aphidimyza*+I, *Autographa californica* NPV+I, *Bacillus sphaericus* Neide+I, *Beauveria brongniartii*+I, *Chrysoperla carnea*+I, *Cryptolaemus montrouzieri*+I, *Cydia pomonella* GV+I, *Dacnusa sibirica*+I, *Diglyphus isaea*+I, *Encarsia formosa*+I, *Eretmocerus eremicus*+I, *Heterorhabditis bacteriophora* and *H. megidis*+I, *Hippodamia convergens*+I, *Leptomastix dactylopii*+I, *Macrolophus caliginosus*+I, *Mamestra brassicae* NPV+I, *Metaphycus helvolus*+I, *Metarhizium anisopliae* var. *acridum*+I, *Metarhizium anisopliae* var. *anisopliae*+I, *Neodiprion sertifer* NPV and *N. lecontei* NPV+I, *Orius* spp.+I, *Paecilomyces fumosoroseus*+I, *Phytoseiulus persimilis*+I, *Steinernema bibionis*+I, *Steinernema carpocapsae*+I, *Steinernema feltiae*+I, *Steinernema glaseri*+I, *Steinernema riobrave*+I, *Steinernema riobravis*+I, *Steinernema scapterisci*+I, *Steinernema* spp.+I, *Trichogramma* spp.+I, *Typhlodromus occidentalis*+I, *Verticillium lecanii*+I, apholate+I, bisazir+I, busulfan+I, dimatif+I, hemel+I, hempa+I, metepa+I, methiotepa+I, methyl apholate+I, morzid+I, penfluron+I, tepa+I, thiohempa+I, thiotepa+I, tretamine+I, uredepa+I, (E)-dec-5-en-1-yl acetate with (E)-dec-5-en-1-ol+I, (E)-tridec-4-en-1-yl acetate+I, (E)-6-methylhept-2-en-4-ol+I, (E,Z)-tetradeca-4,10-dien-1-yl acetate+I, (Z)-dodec-7-en-1-yl acetate+I, (Z)-hexadec-11-enal+I, (Z)-hexadec-11-en-1-yl acetate+I, (Z)-hexadec-13-en-11-yn-1-yl acetate+I, (Z)-icos-13-en-10-one+I, (Z)-tetradec-7-en-1-al+I, (Z)-tetradec-9-en-1-ol+I, (Z)-tetradec-9-en-1-yl acetate+I, (7E,9Z)-dodeca-7,9-dien-1-yl acetate+I, (9Z,11E)-tetradeca-9,11-dien-1-yl acetate+I, (9Z,12E)-tetradeca-9,12-dien-1-yl acetate+I, 14-methyloctadec-1-ene+I, 4-methylnonan-5-ol with 4-methylnonan-5-one+I, alpha-multistriatin+I, brevicomin+I, codlelure+I, codlemone+I, cuelure+I, disparlure+I, dodec-8-en-1-yl acetate+I, dodec-9-en-1-yl acetate+I, dodeca-8+I, 10-dien-1-yl acetate+I, dominicalure+I, ethyl 4-methyloctanoate+I, eugenol+I, frontalin+I, grandlure+I, grandlure I+I, grandlure II+I, grandlure III+I, grandlure IV+I, hexalure+I, ipsdienol+I, ipsenol+I, japonilure+I, lineatin+I, litlure+I, looplure+I, medlure+I, megatomoic acid+I, methyl eugenol+I, muscalure+I, octadeca-2,13-dien-1-yl acetate+I, octadeca-3,13-dien-1-yl acetate+I, orfralure+I, oryctalure+I, ostramone+I, siglure+I, sordidin+I, sulcatol+I, tetradec-11-en-1-yl acetate+I, trimedlure+I, trimedlure A+I, trimedlure $B_1$+I, trimedlure $B_2$+I, trimedlure C+I, trunc-call+I, 2-(octylthio) ethanol+I, butopyronoxyl+I, butoxy(polypropylene glycol)+I, dibutyl adipate+I, dibutyl phthalate+I, dibutyl succinate+I, diethyltoluamide+I, dimethyl carbate+I, dimethyl phthalate+I, ethyl hexanediol+I, hexamide+I, methoquin-butyl+I, methylneodecanamide+I, oxamate+I, picaridin+I, 1-dichloro-1-nitroethane+I, 1,1-dichloro-2,2-bis(4-ethylphenyl)ethane+I, 1,2-dichloropropane with 1,3-dichloropropene+I, 1-bromo-2-chloroethane+I, 2,2,2-trichloro-1-(3,4-dichlorophenyl)ethyl acetate+I, 2,2-dichlorovinyl 2-ethylsulfinylethyl methyl phosphate+I, 2-(1,3-dithiolan-2-yl)phenyl dimethylcarbamate+I, 2-(2-butoxyethoxy)ethyl thiocyanate+I, 2-(4,5-dimethyl-1,3-dioxolan-2-yl)phenyl methylcarbamate+I, 2-(4-chloro-3,5-xylyloxy)ethanol+I, 2-chlorovinyl diethyl phosphate+I, 2-imidazolidone+I, 2-isovalerylindan-1,3-dione+I, 2-methyl(prop-2-ynyl)aminophenyl methylcarbamate+I, 2-thiocyanatoethyl laurate+I, 3-bromo-1-chloro-prop-1-ene+I, 3-methyl-1-phenylpyrazol-5-yl dimethylcarbamate+I, 4-methyl(prop-2-ynyl)amino-3,5-xylyl methylcarbamate+I, 5,5-dimethyl-3-oxocyclohex-1-enyl dimethylcarbamate+I, acethion+I, acrylonitrile+I, aldrin+I, allosamidin+I, allyxycarb+I, alpha-ecdysone+I, aluminium phosphide+I, aminocarb+I, anabasine+I, athidathion+I, azamethiphos+I, *Bacillus thuringiensis* delta endotoxins+I, barium hexafluorosilicate+I, barium polysulfide+I, barthrin+I, Bayer 22/190+I, Bayer 22408+I, beta-cyfluthrin+I, beta-cypermethrin+I, bioethanomethrin+I, biopermethrin+I, bis (2-chloroethyl) ether+I, borax+I, bromfenvinfos+I, bromo-DDT+I, bufencarb+I, butacarb+I, butathiofos+I, butonate+I, calcium arsenate+I, calcium cyanide+I, carbon disulfide+I, carbon tetrachloride+I, cartap hydrochloride+I, cevadine+I, chlorbicyclen+I, chlordane+I, chlordecone+I, chloroform+I, chloropicrin+I, chlorphoxim+chlorprazophos+I, cis-resmethrin+I, cismethrin+I, clocythrin+I, copper acetoarsenite+I, copper arsenate+I, copper oleate+I, coumithoate+I, cryolite+I, CS 708+I, cyanofenphos+I, cyanophos+I, cyclethrin+I, cythioate+I, d-tetramethrin DAEP+I, dazomet+I, decarbofuran+I, diamidafos+I, dicapthon+I, dichlofenthion+I, dicresyl+I, dicyclanil+I, dieldrin+I, diethyl 5-methylpyrazol-3-yl phosphate+I, dilor+I, dimefluthrin+I, dimetan+I, dimethrin+I, dimethylvinphos+I, dimetilan+dinoprop+I, dinosam+I, dinoseb+I, diofenolan+I, dioxabenzofos+I, dithicrofos+I, DSP+ecdysterone+I, EI 1642+I, EMPC+I, EPBP+I, etaphos+I, ethiofencarb+I, ethyl formate+ethylene dibromide+I, ethylene dichloride+I, ethylene oxide+I EXD+I, fenchlorphos+fenethacarb+I, fenitrothion+I, fenoxacrim+I, fenpirithrin+I, fensulfothion+I, fenthion-ethyl flucofuron+I, fosmethilan fospirate+I, fosthietan+I, furathiocarb+I, furethrin+I, guazatine+guazatine acetates+I, sodium tetrathiocarbonate+I, halfenprox+I, HCH+I, HEOD+I, heptachlor+I, heterophos+I, HHDN+I, hydrogen cyanide+I, hyquincarb+I, IPSP+I, isazofos+I, isobenzan+I, isodrin+I, isofenphos+I, isolane+I, isoprothiolane+I, isoxathion+I, juvenile hormone I+I, juvenile hormone II+I, juvenile hormone III+I, kelevan+I, kinoprene+I, lead arsenate+I, leptophos+I, lirimfos+I, lythidathion+I, m-cumenyl methylcarbamate+I, magnesium phosphide+I, mazidox+I, mecarphon+I, menazon+I, mercurous chloride+I, mesulfenfos+I, metam+I, metam-potassium+I, metam-sodium+I, methanesulfonyl fluoride+I, methocrotophos+I, methoprene+I, methothrin+I, methoxychlor+I, methyl isothiocyanate+I, methylchloroform+I, methylene chloride+I, metoxadiazone+I, mirex+I, naftalofos+I, naphthalene+I, NC-170+I, nicotine+I, nicotine sulfate+I, nithiazine+I, nornicotine+I, O-5-dichloro-4-iodophenyl O-ethyl ethylphosphonothioate+I, O,O-diethyl O-4-methyl-2-oxo-2H-chromen-7-ylphosphorothioate+I, O,O-diethyl O-6-methyl-2-propylpyrimidin-4-ylphosphorothioate+I, O,O,O',O'-tetrapropyl dithiopyrophosphate+I, oleic acid+I, para-dichlorobenzene+I, parathion-methyl+I, pentachlorophenol+I, pentachlorophenyl laurate+I, PH 60-38+I, phenkapton+I, phosnichlor+I, phosphine+I, phoxim-methyl+I, pirimetaphos+I, polychlorodicyclopentadiene isomers+I, potassium arsenite+I, potassium thiocyanate+I, precocene I+I, precocene II+I, precocene III+I, primidophos+I, profluthrin+I, promecarb+I, prothiofos+I, pyrazophos+I, pyresmethrin+I, quassia+I, quinalphos-methyl+I, quinothion+I, rafoxanide+I, resmethrin+I, rotenone+I, kadethrin+I, ryania+I, ryanodine+I, sabadilla)+I, schradan+I, sebufos+I, SI-0009+I, thiapronil+I, sodium arsenite+I, sodium cyanide+I, sodium fluoride+I, sodium hexafluorosilicate+I, sodium pentachlorophenoxide+I, sodium selenate+I, sodium thiocyanate+I, sulcofuron+I, sulcofuron-sodium+I, sulfuryl fluoride+I, sulprofos+I, tar oils+I, tazimcarb+I, TDE+I, tebupirimfos+I, temephos+I, terallethrin+I, tetrachloroethane+I, thicrofos+I, thiocyclam+I, thiocyclam hydrogen oxalate+I, thionazin+I, thiosultap+I, thiosultap-sodium+I, tralomethrin+I, transpermethrin+I, triazamate+I, trichlormetaphos-3+I, trichloronat+I, trimethacarb+I, tolprocarb+I, triclopyricarb+I, triprene+I, veratridine+I, veratrine+I, XMC+I, zetamethrin+I, zinc phosphide+I, zolaprofos+I, and meperfluthrin+I, tetramethylfluthrin+I, bis(tributyltin) oxide+I, bromoacetamide+I, ferric phosphate+I, niclosamide-olamine+I, tributyltin oxide+I, pyrimorph+I, trifenmorph+I, 1,2-dibromo-3-chloropropane+I, 1,3-dichloropropene+I, 3,4-dichlorotetrahydrothiophene 1,1-dioxide+I, 3-(4-chlorophenyl)-5-methylrhodanine+I, 5-methyl-6-thioxo-1,3,5-thiadiazinan-3-ylacetic acid+I, 6-isopentenylaminopurine+I, benclothiaz+I, cytokinins+I, DCIP+I, furfural+I, isamidofos+I, kinetin+I, Myrothecium verrucaria composition+I, tetrachlorothiophene+I, xylenols+I, zeatin+I, potassium ethylxanthate+I, acibenzolar+I, acibenzolar-S-methyl+I, Reynoutria sachalinensis extract+I, alpha-chlorohydrin+I, antu+I, barium carbonate+I, bisthiosemi+I, brodifacoum+I, bromadiolone+I, bromethalin+I, chlorophacinone+I, cholecalciferol+I, coumachlor+I, coumafuryl+I, coumatetralyl+I, crimidine+I, difenacoum+I, difethialone+I, diphacinone+I, ergocalciferol+I, flocoumafen+I, fluoroacetamide+I, flupropadine+I, flupropadine hydrochloride+I, norbormide+I, phosacetim+I, phosphorus+I, pindone+I, pyrinuron+I, scilliroside+I, sodium fluoroacetate+I, thallium sulfate+I, warfarin+I, 2-(2-butoxyethoxy)ethyl piperonylate+I, 5-(1,3-benzodioxol-5-yl)-3-hexylcyclohex-2-enone+I, farnesol with nerolidol+I, verbutin+I, MGK 264+I, piperonyl butoxide+I, piprotal+I, propyl isomer+I, S421+I, sesamex+I, sesasmolin+I, sulfoxide+I, anthraquinone+I, copper naphthenate+I, copper oxychloride+I, dicyclopentadiene+I, thiram+I, zinc naphthenate+I, ziram+I, imanin+I, ribavirin+I, mercuric oxide+I, thiophanate-methyl+I, azaconazole+I, bitertanol+I, bromuconazole+I, cyproconazole+I, difenoconazole+I, diniconazole+I, epoxiconazole+I, fenbuconazole+I, fluquinconazole+I, flusilazole+I, flutriafol+I, furametpyr+I, hexaconazole+I, imazalil+I, imiben-conazole+I, ipconazole+I, metconazole+I, myclobutanil+I, paclobutrazole+I, pefurazoate+I, penconazole+I, prothioconazole+I, pyrifenox+I, prochloraz+I, propiconazole+I, pyrisoxazole+I, simeconazole+I, tebuconazole+I, tetraconazole+I, triadimefon+I, triadimenol+I, triflumizole+I, triticonazole+I, ancymidol+I, fenarimol+I, nuarimol+I, bupirimate+I, dimethirimol+I, ethirimol+I, dodemorph+I, fenpropidine+I, fenpropimorph+I, spiroxamine+I, tridemorph+I, cyprodinil+I, mepanipyrim+I, pyrimethanil+I, fenpiclonil+I, fludioxonil+I, benalaxyl+I, furalaxyl+I, metalaxyl+I, R-metalaxyl+I, ofurace+I, oxadixyl+I, carbendazim+I, debacarb+I, fuberidazole+I, thiaben-dazole+I, chlozolinate+I, dichlozoline+I, myclozoline+I, procymidone+I, vinclozoline+I, boscalid+I, carboxin+I, fenfuram+I, flutolanil+I, mepronil+I, oxycarboxin+I, penthiopyrad+I, thifluzamide+I, dodine+I, iminoctadine+I, azoxystrobin+I, dimoxystrobin+I, enestroburin+I, fenaminstrobin+I, flufenoxystrobin+I, fluoxastrobin+I, kresoxim-methyl+I, metominostrobin+I, trifloxystrobin+I, orysastrobin+I, picoxystrobin+I, pyraclostrobin+I, pyrametostrobin+I, pyraoxystrobin+I, ferbam+I, mancozeb+I, maneb+I, metiram+I, propineb+I, zineb+I, captafol+I, captan+I, fluoroimide+I, folpet+I, tolylfluanid+I, bordeaux mixture+I, copper oxide+I, mancopper+I, oxine-copper+I, nitrothal-isopropyl+I, edifenphos+I, iprobenphos+I, phosdiphen+I, tolclofos-methyl+I, anilazine+I, benthiavalicarb+I, blasticidin-S+I, chloroneb+I, chlorothalonil+I, cyflufenamid+I, cymoxanil+I, diclocymet+I, diclomezine+I, dicloran+I, diethofencarb+I, dimethomorph+I, flumorph+I, dithianon+I, ethaboxam+I, etridiazole+I, famoxadone+I, fenamidone+I, fenoxanil+I, ferimzone+I, fluazinam+I, fluopicolide+I, flusulfamide+I, fluxapyroxad+I, fenhexamid+I, fosetyl-aluminium+I, hymexazol+I, iprovalicarb+I, cyazofamid+I, methasulfocarb+I, metrafenone+I, pencycuron+I, phthalide+I, polyoxins+I, propamocarb+I, pyribencarb+I, proquinazid+I, pyroquilon+I, pyriofenone+I, quinoxyfen+I, quintozene+I, tiadinil+I, triazoxide+I, tricyclazole+I, triforine+I, validamycin+I, valifenalate+I, zoxamide+I, mandipropamid+I, isopyrazam+I, sedaxane+I, benzovindiflupyr+I, pydiflumetofen+I, 3-difluoromethyl-1-methyl-1H-pyrazole-4-carboxylic acid (3',4',5'-trifluoro-biphenyl-2-yl)-amide+I, isoflucypram+I, isotianil+I, dipymetitrone+I, 6-ethyl-5,7-dioxo-pyrrolo[4,5][1,4]dithiino[1,2-c]isothiazole-3-carbonitrile+I, 2-(difluoromethyl)-N-[3-ethyl-1,1-dimethyl-indan-4-yl]pyridine-3-carboxamide+I, 4-(2,6-difluorophenyl)-6-methyl-5-phenyl-pyridazine-3-carbonitrile+I, (R)-3-(difluoromethyl)-1-methyl-N-[1,1,3-trimethylindan-4-yl]pyrazole-4-carboxamide+I, 4-(2-bromo-4-fluoro-phenyl)-N-(2-chloro-6-fluoro-phenyl)-2,5-dimethyl-pyrazol-3-amine+I, 4-(2-bromo-4-fluorophenyl)-N-(2-chloro-6-fluorophenyl)-1,3-dimethyl-1H-pyrazol-5-amine+I, fluindapyr+I, coumethoxystrobin (jiaxiangjunzhi)+I, Ivbenmixianan+I, dichlobentiazox+I, mandestrobin+I, 3-(4,4-difluoro-3,4-dihydro-3,3-dimethyl-isoquinolin-1-yl)quinolone+I, 2-[2-fluoro-6-[(8-fluoro-2-methyl-3-quinolyl)oxy]phenyl]propan-2-ol+I, oxathiapiprolin+I, tert-butyl N-[6-[[[(1-methyltetrazol-5-yl)-phenyl-methylene]amino]oxymethyl]-2-pyridyl]carbamate+I, pyraziflumid+I, inpyrfluxam+I, trolprocarb+I, mefentrifluconazole+I, ipfentrifluconazole+I, 2-(difluoromethyl)-N-[(3R)-3-ethyl-1,1-dimethyl-indan-4-yl]pyridine-3-carboxamide+I, N'-(2,5-dimethyl-4-phenoxy-phenyl)-N-ethyl-N-methyl-formamidine+I, N'-[4-(4,5-dichlorothiazol-2-yl)oxy-2,5-dimethyl-phenyl]-N-ethyl-N-methyl-formamidine+I, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl] methanesulfonate+I, but-3-ynyl N-[6-[[(Z)-[(1-methyltetrazol-5-yl)-phenyl-methylene]amino]oxymethyl]-2-pyridyl]carbamate+I, methyl N-[[5-[4-(2,4-dimethylphenyl)triazol-2-yl]-2-methyl-phenyl]methyl]carbamate+I, 3-chloro-6-methyl-5-phenyl-4-(2,4,6-trifluorophenyl)pyridazine+I, pyridachlometyl+I, 3-(difluoromethyl)-1-methyl-N-[1,1,3-trimethylindan-4-yl]pyrazole-4-carboxamide+I, 1-[2-[[1-(4-chlorophenyl)pyrazol-3-yl]oxymethyl]-3-methyl-phenyl]-4-methyl-tetrazol-5-one+I, 1-methyl-4-[3-methyl-2-[[2-methyl-4-(3,4,5-trimethylpyrazol-1-yl)phenoxy]methyl]phenyl]tetrazol-5-one+I, aminopyrifen+I, ametoctradin+I, amisulbrom+I, penflufen+I, (Z,2E)-5-[1-(4-chlorophenyl)pyrazo-3-yl]oxy-2-methoxyimino-N,3-dimethyl-pent-3-enamide+I, florylpicoxamid+I, fenpicoxamid+I, tebufloquin+I, ipflufenoquin+I, quinofumelin+I, isofetamid+I, N-[2-[2,4-dichlorophenoxy]phenyl]-3-(difluoromethyl)-1-methyl-pyrazole-4-carboxamide+I, N-[2-[2-chloro-4-(trifluoromethyl)phenoxy]phenyl]-3-(difluoromethyl)-1-methyl-pyrazole-4-carboxamide+I, benzothiostrobin+I, phenamacril+I, 5-amino-1,3,4-thiadiazole-2-thiol zinc salt (2:1)+I, fluopyram+I, flutianil+I, fluopimomide+I, pyrapropoyne+I, picarbutrazox+I, 2-(difluoromethyl)-N-(3-ethyl-1,1-dimethyl-indan-4-yl)pyridine-3-carboxamide+I, 2-(difluoromethyl)-N-((3R)-1,1,3-trimethylindan-4-yl)pyridine-3-carboxamide+I, 4-[[6-[2-(2,4-difluorophenyl)-1,1-difluoro-2-hydroxy-3-(1,2,4-triazol-1-yl)propyl]-3-pyridyl]oxy]benzonitrile+I, metyltetraprole+I, 2-(difluoromethyl)-N-((3R)-1,1,3-trimethylindan-4-yl)pyridine-3-carboxamide+I, α-(1,1-dimethylethyl)-α-[4''-(trifluoromethoxy)[1,1'-biphenyl]-4-yl]-5-pyrimidinemethanol+I, fluoxapiprolin+I, enoxastrobin+I, 4-[[6-[2-(2,4-difluorophenyl)-1,1-difluoro-2-hydroxy-3-(1,2,4-triazol-1-yl)propyl]-3-pyridyl]oxy]benzonitrile+I, 4-[[6-[2-(2,4-difluorophenyl)-1,1-difluoro-2-hydroxy-3-(5-sulfanyl-1,2,4-triazol-1-yl)propyl]-3-pyridyl]oxy]benzonitrile+I, 4-[[6-[2-(2,4-difluorophenyl)-1,1-difluoro-2-hydroxy-3-(5-thioxo-4H-1,2,4-triazol-1-yl)propyl]-3-pyridyl]oxy]benzonitrile+I, trinexapac+I, coumoxystrobin+I, zhongshengmycin+I, thiodiazole copper+I, zinc thiazole+I, amectotractin+I, iprodione+I. N-methoxy-N-[[4-[5-(trifluoromethyl)-1,2,4-oxadiazol-3-yl]phenyl]methyl]cyclopropanecarboxamide+I, N,2-dimethoxy-N-[[4-[5-(trifluoromethyl)-1,2,4-oxadiazol-3-yl]phenyl]methyl]propanamide+I, N-ethyl-2-methyl-N-[[4-[5-(trifluoromethyl)-1,2,4-oxadiazol-3-yl]phenyl]methyl]propanamide+I, 1-methoxy-3-methyl-1-[[4-[5-(trifluoromethyl)-1,2,4-oxadiazol-3-yl]phenyl]methyl]urea+I, 1,3-dimethoxy-1-[[4-[5-(trifluoromethyl)-1,2,4-oxadiazol-3-yl]phenyl]methyl]urea+I, 3-ethyl-1-methoxy-1-[[4-[5-(trifluoromethyl)-1,2,4-oxadiazol-3-yl]phenyl]methyl]urea+I, N-[[4-[5-(trifluoromethyl)-1,2,4-oxadiazol-3-yl]phenyl]methyl]propanamide+I, 4,4-dimethyl-2-[[4-[5-(trifluoromethyl)-1,2,4-oxadiazol-3-yl]phenyl]methyl]isoxazolidin-3-one+I, 5,5-dimethyl-2-[[4-[5-(trifluoromethyl)-1,2,4-oxadiazol-3-yl]phenyl]methyl]isoxazolidin-3-one+I, ethyl 1-[[4-[5-(trifluoromethyl)-1,2,4-oxadiazol-3-yl]phenyl]methyl]pyrazole-4-carboxylate+I, N,N-dimethyl-1-[[4-[5-(trifluoromethyl)-1,2,4-oxadiazol-3-yl]phenyl]methyl]-1,2,4-triazol-3-amine+I. The compounds in this paragraph may be prepared from the methods described in WO 2017/055473, WO 2017/055469, WO 2017/093348 and WO 2017/118689.

2-[6-(4-chlorophenoxy)-2-(trifluoromethyl)-3-pyridyl]-1-(1,2,4-triazol-1-yl)propan-2-ol+I (this compound may be prepared from the methods described in WO 2017/029179).

2-[6-(4-bromophenoxy)-2-(trifluoromethyl)-3-pyridyl]-1-(1,2,4-triazol-1-yl)propan-2-ol+I (this compound may be prepared from the methods described in WO 2017/029179).

3-[2-(1-chlorocyclopropyl)-3-(2-fluorophenyl)-2-hydroxy-propyl]imidazole-4-carbonitrile I (this compound may be prepared from the methods described in WO 2016/156290).

3-[2-(1-chlorocyclopropyl)-3-(3-chloro-2-fluoro-phenyl)-2-hydroxy-propyl]imidazole-4-carbonitrile+I (this compound may be prepared from the methods described in WO 2016/156290).

(4-phenoxyphenyl)methyl 2-amino-6-methyl-pyridine-3-carboxylate+I (this compound may be prepared from the methods described in WO 2014/006945).

2,6-Dimethyl-1H,5H-[1,4]dithiino[2,3-c:5,6-c']dipyrrole-1,3,5,7(2H,6H)-tetrone+I (this compound may be prepared from the methods described in WO 2011/138281).

N-methyl-4-[5-(trifluoromethyl)-1,2,4-oxadiazol-3-yl]benzenecarbothioamide+I.

N-methyl-4-[5-(trifluoromethyl)-1,2,4-oxadiazol-3-yl]benzamide+I.

(Z,2E)-5-[1-(2,4-dichlorophenyl)pyrazo]-3-yl]oxy-2-methoxyimino-N,3-dimethyl-pent-3-enamide+I (this compound may be prepared from the methods described in WO 2018/153707).

N'-(2-chloro-5-methyl-4-phenoxy-phenyl)-N-ethyl-N-methyl-formamidine+I.

N'-[2-chloro-4-(2-fluorophenoxy)-5-methyl-phenyl]-N-ethyl-N-methyl-formamidine+I (this compound may be prepared from the methods described in WO 2016/202742).

2-(difluoromethyl)-N-[(3S)-3-ethyl-1,1-dimethyl-indan-4-yl]pyridine-3-carboxamide+I (this compound may be prepared from the methods described in WO 2014/095675).

The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula (I) and an active ingredient as described above are preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula (I) and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) and the active ingredient(s) as described above, is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds of formula (I) for the preparation of these compositions are also a subject of the invention.

Another aspect of the invention is related to the use of a compound of formula (I) or of a preferred individual compound as defined herein, of a composition comprising at least one compound of formula (I) or at least one preferred individual compound as above-defined, or of a fungicidal or insecticidal mixture comprising at least one compound of formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g. harvested food crops, or non-living materials by insects or by phytopathogenic microorganisms, preferably fungal organisms.

A further aspect of the invention is related to a method of controlling or preventing an infestation of plants, e.g., useful plants such as crop plants, propagation material thereof, e.g. seeds, harvested crops, e.g., harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

When the combinations of the present invention are used for treating seed, rates of 0.001 to 50 g of a compound of formula I per kg of seed, preferably from 0.01 to 10 g per kg of seed are generally sufficient.

Suitably, a composition comprising a compound of formula (I) according to the present invention is applied either preventative, meaning prior to disease development or curative, meaning after disease development.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) optionally together with other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Whereas it is preferred to formulate commercial products as concentrates, the end user will normally use dilute formulations.

EXAMPLES

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 60 ppm, 20 ppm or 2 ppm.

Compounds of formula (I) may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile (including improved crop tolerance), improved physico-chemical properties, or increased biodegradability).

Throughout this description, temperatures are given in degrees Celsius and "m.p." means melting point. LC/MS means Liquid Chromatography Mass Spectroscopy and the description of the apparatus and the methods is as follows:
Method G:

Spectra were recorded on a Mass Spectrometer from Waters (SQD, SQDII Single quadrupole mass spectrometer) equipped with an electrospray source (Polarity: positive and negative ions), Capillary: 3.00 kV, Cone range: 30 V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (ml/min) 0.85

Method H:

Spectra were recorded on a Mass Spectrometer from Waters (SQD, SQDII Single quadrupole mass spectrometer) equipped with an electrospray source (Polarity: positive and negative ions), Capillary: 3.00 kV, Cone range: 30V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 2.7 min; Flow (ml/min) 0.85

Method I:

Spectra were recorded on a Mass Spectrometer (ACQUITY UPLC) from Waters (SQD, SQDII or ZQ Single quadrupole mass spectrometer) equipped with an electrospray source (Polarity: positive or negative ions, Capillary (kV) 3.5, Cone (V) 30.00, Extractor (V) 3.00, Source Temperature (° C.) 150, Desolvation Temperature (° C.) 400, Cone Gas Flow (L/Hr) 60, Desolvation Gas Flow (L/Hr) 700, Mass range: 140 to 800 Da) and an Acquity UPLC from Waters: Binary pump, heated column compartment and diode-array detector. Solvent degasser, binary pump, heated column compartment and diode-array detector. Solvent degasser, binary pump, heated column compartment and diode-array detector. Column: Waters ACQUITY UPLC HSS T3; Column length: 30 mm; Internal diameter of column: 2.1 mm; Particle Size: 1.8 µm; Temperature: 60° C., DAD Wavelength range (nm): 210 to 400. Solvent Gradient A: Water/Methanol 9:1,0.1% formic acid and Solvent B: Acetonitrile, 0.1% formic acid

| Time (minutes) | A (%) | B (%) | Flow rate (ml/min) |
| --- | --- | --- | --- |
| 0 | 100 | 0 | 0.75 |
| 2.5 | 0 | 100 | 0.75 |
| 2.8 | 0 | 100 | 0.75 |
| 3.0 | 100 | 0 | 0.75 |

Method J:

Spectra were recorded on a Mass Spectrometer 6410 Triple Quadruple Mass Spectrometer from Agilent Technologies equipped with an electrospray source (Positive and Negative Polarity Switch, Capillary (kV) 4.00, Scan Type MS2 Scan, Fragmentor (V) 100.00, Gas Temperature (° C.) 350, Gas Flow (L/min) 11, Nebulizer Gas (psi) 45, Mass range: 110 to 1000 Da) and an Agilent 1200 Series HPLC: DAD Wavelength range: 210 to 400 nm, Column: KINETEX EVO C18, Column length: 50 mm, Internal diameter of column: 4.6 mm, Particle Size: 2.6 µm, Column oven temperature: 40° C.

Gradient Conditions:
Solvent A: Water with 0.1% formic acid:Acetonitrile: 95:5 v/v
Solvent B: Acetonitrile with 0.1% formic acid

| Time (minutes) | A (%) | B (%) | Flow rate (ml/min) |
| --- | --- | --- | --- |
| 0 | 90 | 10 | 1.8 |
| 0.9 | 0 | 100 | 1.8 |
| 1.8 | 0 | 100 | 1.8 |
| 2.2 | 90 | 10 | 1.8 |
| 2.5 | 90 | 10 | 1.8 |

Where necessary, enantiomerically pure final compounds may be obtained from racemic materials as appropriate via standard physical separation techniques, such as reverse phase chiral chromatography, or through stereoselective synthetic techniques, eg, by using chiral starting materials.

Formulation Examples

| | Wettable powders | | |
| --- | --- | --- | --- |
| | a) | b) | c) |
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| | Powders for dry seed treatment | | |
| --- | --- | --- | --- |
| | a) | b) | c) |
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

| Emulsifiable concentrate | |
| --- | --- |
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | | | |
|---|---|---|---|
| | a) | b) | 0) |
| Active ingredient [compound of formula (I)] | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient [compound of formula (I)] | 15% |
| sodium lignosulfonate | 2% |
| Carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsionin water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow-Release Capsule Suspension 28 parts of a combination of the compound of formula (I) are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

List of Abbreviations $CDCl_3$=chloroform-d
° C.=degrees Celsius
DCM=dichloromethane
DMF=dimethylformamide
DMSO=dimethyl sulfoxide
d=doublet
EtOAc=ethyl acetate
h=hour(s)
HCl=hydrochloric acid
M=molar
min=minutes
MHz=mega hertz
mp=melting point
$Pd_2(dba)_3$=Tris(dibenzylideneacetone)dipalladium(0)
ppm=parts per million
RT=room temperature
Rt=retention time
rh=relative humidity
s=singlet
=triplet
THF=tetrahydrofuran
LCMS=Liquid Chromatography Mass Spectrometry (description of the apparatus and the methods used for LC/MS analysis are given above)

PREPARATION EXAMPLES

Example A1: Preparation of methyl (Z)-2-[5-(4-cyclopropyltriazol-2-yl)-2-methyl-phenoxy]-3-methoxy-prop-2-enoate (F-8)

Step 1:

To a solution of 5-bromo-2-methylphenol (53.47 mmol, 10.00 g) and methyl 2-bromoacetate (1.5 equiv., 80.20 mmol, 12.27 g, 7.44 mL) in tetrahydrofuran (0.5 mol/L, 106.9 mL) at room temperature was added potassium carbonate (2 equiv., 106.9 mmol, 14.78 g), and the light brown suspension was heated to 65° C. for 2 h and then allowed to cool down to room temperature overnight. The reaction mixture was diluted with EtOAc and washed with water. The aqueous phase was extracted with EtOAc, and the total combined organic layer was washed with water, brine, dried with $Na_2SO_4$, filtered and concentrated in vacuo to give methyl 2-(5-bromo-2-methyl-phenoxy)acetate (47.22 mmol, 15.89 g, 88% yield) as a brown liquid. The crude oil was slightly contaminated with residual methyl-2-bromoacetate, but was taken directly to the next step without further purification.

LCMS (Method H), Rt=1.59 min, MS: (M+1)=259, 261; $^1$H NMR (400 MHz, CDCl3) δ ppm 2.25 (s, 3H) 3.84 (s, 3H) 4.66 (s, 2H) 6.84 (d, 1H) 7.05 (m, 2H)

Step 2:

Part 1: To a solution of 2-(5-bromo-2-methyl-phenoxy)acetate (20.8 g, 80.3 mmol) and methyl formate (6.0 equiv., 482 mmol, 29.5 g, 30.5 mL) in tetrahydrofuran (0.5 mol/L, 161 mL) at room temperature under argon was added sodium methoxide (20 equiv., 161 mmol, 9.13 g) portion-wise. The reaction was slightly exothermic and was kept below 30° C. with the assistance of a room temperature water bath. The reaction mixture was stirred at room temperature for 1 h and quenched by the slow addition of an aqueous saturated solution of $NaHCO_3$. The two phases were separated and the aqueous phase was extracted with EtOAc. The total combined organic layer was washed with aqueous saturated solution of $NaHCO_3$, brine, dried with $Na_2SO_4$, filtered and concentrated in vacuo to give methyl-2-(5-bromo-2-methyl-phenoxy)-3-hydroxy-prop-2-enoate, which was taken directly to the next step without further purification.

LCMS (Method G), Rt=0.80 and 0.90 min, MS: (M+1)=287, 289

Part 2: To a solution of the crude methyl-2-(5-bromo-2-methyl-phenoxy)-3-hydroxy-prop-2-enoate and dimethyl sulfate (1.2 equiv., 93.2 mmol, 11.8 g, 8.8 mL) in DMF (0.5 mol/L, 155 mL) at room temperature under argon was added potassium carbonate (1.5 equiv., 117 mmol, 16.3 g), and the reaction mixture was stirred at room temperature for 2 h. The reaction mixture was quenched by the slow addition of water, and the mixture was extracted with EtOAc. The total combined organic layer was washed with aqueous saturated solution of $NaHCO_3$, brine, dried with $Na_2SO_4$, filtered and concentrated in vacuo. The residue was purified by flash chromatography (cyclohexane:EtOAc) to give methyl (Z)-2-(5-bromo-2-methyl-phenoxy)-3-methoxy-prop-2-enoate (59.6 mmol, 18.0 g, 75% yield) as an off-white solid. LCMS (Method G), Rt=1.02 min, MS: (M+1)=301, 303; $^1$H NMR (400 MHz, CDCl$_3$) δ ppm 2.31 (s, 3H) 3.74 (s, 3H) 3.91 (s, 3H) 6.86 (d, 1H) 7.05 (m, 2H) 7.35 (s, 1H)

Step 3:

A solution of Tetramethyl-t-BuXphos (0.10 equiv., 0.066 mmol, 0.033 g) and $Pd_2(dba)_3$ (0.05 equiv., 0.033 mmol, 0.031 g) in 1 mL toluene under argon was heated at 110° C. for 3 minutes, and the mixture was then allowed to cool down to room temperature. The pre-formed palladium catalyst was transferred to a mixture of methyl (Z)-2-(5-bromo-2-methyl-phenoxy)-3-methoxy-prop-2-enoate (0.66 mmol, 0.20 g), 4-cyclopropyl-2H-triazole (1.1 equiv., 0.73 mmol, 0.080 g) and potassium carbonate (2.0 equiv., 1.33 mmol, 0.184 g) in toluene (0.2 mol/L, 3.3 mL) at room temperature and the obtained dark brown suspension was heated to 110° C. for 1 h. The reaction mixture was allowed to cool down to room temperature, then EtOAc was added. The organic phase was washed with water, and the aqueous was extracted with EtOAc. The total combined organic layer was washed with brine, dried with $Na_2SO_4$, filtered and concentrated in vacuo. The residue was purified by flash chromatography (cyclohexane:EtOAc) to give methyl (Z)-2-[5-(4-cyclopropyltriazol-2-yl)-2-methyl-phenoxy]-3-methoxy-prop-2-enoate (0.23 mmol, 0.075 g, 34% yield).

LCMS (Method G), Rt=1.07 min, MS: (M+1)=330; $^1$H NMR (400 MHz, CDCl$_3$) δ ppm 0.88 (m, 2H) 1.04 (m, 2H) 2.03 (m, 1H) 2.40 (s, 3H) 3.74 (s, 3H) 3.91 (s, 3H) 7.24 (d, 1H) 7.40 (s, 1H) 7.41 (d, 1H) 7.46 (s, 1H) 7.58 (dd, 1H)

Example A2: Preparation of methyl (Z)-3-methoxy-2-[2-methyl-5-[3-(trifluoromethyl)pyrazo]-1-yl]phenoxy]prop-2-enoate (E-105)

A solution of Tetramethyl-t-BuXphos (0.10 equiv., 0.050 mmol, 0.025 g) and $Pd_2(dba)_3$ (0.05 equiv., 0.025 mmol, 0.024 g) in 1 mL toluene under argon was heated at 110° C. for 3 minutes. This mixture was then allowed to cool down to room temperature. The pre-formed active palladium catalyst was transferred to a mixture of methyl (Z)-2-(5-bromo-2-methyl-phenoxy)-3-methoxy-prop-2-enoate (0.50 mmol, 0.15 g), 3-(trifluoromethyl)-1H-pyrazole (1.2 equiv., 0.60 mmol, 0.082 g) and potassium carbonate (2.0 equiv., 1.0 mmol, 0.138 g) in toluene (0.2 mol/L, 2.5 mL) at room temperature and the obtained dark brown suspension was heated to 110° C. for 1 h. The reaction mixture was allowed to cool down to room temperature, then EtOAc was added. The organic phase was washed with water, and the aqueous was extracted with EtOAc. The total combined organic layer was washed with brine, dried with $Na_2SO_4$, filtered and concentrated in vacuo. The residue was purified by flash chromatography (cyclohexane:EtOAc) to give methyl (Z)-3-methoxy-2-[2-methyl-5-[3-(trifluoromethyl)pyrazo]-1-yl]phenoxy]prop-2-enoate (0.28 mmol, 0.10 g, 56% yield) as a white solid.

mp: 154-156° C.; LCMS (Method G), Rt=1.07 min, MS: (M+1)=357; $^1$H NMR (400 MHz, CDCl$_3$) δ ppm 2.40 (s, 3H) 3.75 (s, 3H) 3.93 (s, 3H) 6.69 (m, 1H) 7.10 (d, 1H) 7.19-7.30 (m, 2H) 7.40 (s, 1H) 7.87 (m, 1H)

Example A3: Preparation of methyl (Z)-2-[5-(3-iodopyrazol-1-yl)-2-methyl-phenoxy]-3-methoxy-prop-2-enoate (E-78)

Step 1:

To a solution of methyl (Z)-2-(5-bromo-2-methyl-phenoxy)-3-methoxy-prop-2-enoate (66.4 mmol, 20.0 g) in 1,4-dioxane (133 mL) at room temperature were added bis(pinacolato)diboron (1.10 equiv., 73.1 mmol, 18.7), potassium acetate (2.00 equiv., 133 mmol, 13.6 g) and 1,1'-bis(diphenylphosphino)ferrocene-palladium(II)dichloride dichloromethane complex (0.025 equiv., 1.66 mmol, 1.38 g), and the reaction mixture was then heated at 100° C. (inside temperature 94° C.) for 90 min. The dark brown suspension was diluted with EtOAc and water was added. The layers were separated and the aqueous phase was extracted with EtOAc. The total combined organic layer was washed with brine, dried with $Na_2SO_4$, filtered, and concentrated in vacuo. The residue was purified by flash chromatography (cyclohexane:EtOAc) to give a beige wet crystalline solid, which was triturated with a small amount of hexane, filtered and dried in vacuo to give methyl (Z)-3-methoxy-2-[2-methyl-5-(4,4,5,5-tetramethyl-1,3,2-dioxaborolan-2-yl)phenoxy]prop-2-enoate (32.6 mmol, 12.0 g, 49% yield) as a white solid.

LCMS (Method H), Rt=1.82 min, MS: (M+1)=349; $^1$H NMR (400 MHz, $CDCl_3$) δ ppm 1.34 (s, 12H) 2.39 (s, 3H) 3.72 (s, 3H) 3.89 (s, 3H) 7.12 (s, 1H) 7.19 (d, 1H) 7.34 (s, 1H) 7.39 (d, 1H)

Step 2:

To a solution of methyl (Z)-3-methoxy-2-[2-methyl-5-(4,4,5,5-tetramethyl-1,3,2-dioxaborolan-2-yl)phenoxy]prop-2-enoate (14.4 mmol, 5.00 g) in tetrahydrofuran:water mixture (4:1 V/V, 72 mL) was added sodium periodate (3.00 equiv., 43.1 mmol, 9.31 g) followed by a solution of hydrochloric acid (2.0 M, 0.25 equiv., 3.59 mmol, 1.79 mL). The obtained white suspension was stirred at room temperature for 4 h, then EtOAc and water were added. The layers were separated, and the aqueous phase was extracted with EtOAc. The total combined organic layer was washed with brine, dried with $Na_2SO_4$, filtered and concentrated in vacuo to give [3-[(Z)-2-methoxy-1-methoxycarbonyl-vinyloxy]-4-methyl-phenyl]boronic acid (12.1 mmol, 3.58 g, 84% yield) as a white solid.

LCMS (Method H), Rt=1.00 min, MS: (M+H)=367; $^1$H NMR (400 MHz, DMSO-d6) δ ppm 2.23 (s, 3H) 3.64 (s, 3H) 3.85 (s, 3H) 7.12 (m, 2H) 7.33 (d, 1H) 7.54 (s, 1H) 7.96 (brs, 2H)

Step 3:

To a suspension of [3-[(Z)-2-methoxy-1-methoxycarbonyl-vinyloxy]-4-methyl-phenyl]boronic acid (0.28 mmol, 0.075 g), 3-iodo-1h-pyrazole (1.1 equiv., 0.31 mmol, 0.060 g) and sodium carbonate (1.5 equiv., 0.42 mmol, 0.045 g) in N,N-dimethylacetamide (0.33 mol/L, 0.85 mL) at room temperature under air, were added copper(II) acetate (0.25 equiv., 0.070 mmol, 0.013 g) and pyridine (0.50 equiv., 0.141 mmol, 0.011 g, 0.012 mL), and the reaction mixture was heated at 80° C. overnight. The mixture was diluted with EtOAc and quenched with an aqueous solution of $NH_4Cl$ (2.5 mol/L). The layers were separated and the aqueous phase was extracted with EtOAc. The combined organic layers were washed with brine, dried with $Na_2SO_4$, filtered and concentrated in vacuo. The residue was purified by flash chromatography to give methyl (Z)-2-[5-(3-iodopyrazol-1-yl)-2-methyl-phenoxy]-3-methoxy-prop-2-enoate (0.12 mmol, 0.057 g, 44% yield) as a white solid.

mp: 156-159° C.; LCMS (Method H), Rt=1.69 min, MS: (M+1)=415; $^1$H NMR (400 MHz, $CDCl_3$) δ ppm 2.39 (s, 3H) 3.74 (s, 3H) 3.92 (s, 3H) 6.60 (d, 1H) 7.06 (d, 1H) 7.14 (dd, 1H) 7.22 (d, 1H) 7.38 (s, 1H) 7.66 (d, 1H)

Example A4: Preparation of methyl (Z)-2-[5-(3-cyclohexylpyrazol-1-yl)-2-methyl-phenoxy]-3-methoxy-prop-2-enoate (E-36)

Step 1:

Procedure: To a solution of methyl (Z)-2-[5-(3-iodopyrazol-1-yl)-2-methyl-phenoxy]-3-methoxy-prop-2-enoate (0.18 mmol, 0.075 g), cesium carbonate (2.5 equiv., 0.45 mmol, 0.148 g) and cyclohex-1-en-1-ylboronic acid (1.75 equiv., 0.32 mmol, 0.040 g) in 1,4-dioxane (0.25 mol/L, 0.73 mL) and water (0.40 mL/mmol, 0.072 mL) at room temperature was added CATACXIUM-A® Pd-G3 (0.10 equiv., 0.018 mmol, 0.014 g), and the reaction mixture was heated at 100° C. for 80 min. The reaction mixture was allowed to cool down to room temperature, filtered over a pad of $Na_2SO_4$. The pad was washed with EtOAc, and the filtrate was concentrated in vacuo. The residue was purified by flash chromatography to give methyl (Z)-2-[5-[3-(cyclohexen-1-yl)pyrazol-1-yl]-2-methyl-phenoxy]-3-methoxy-prop-2-enoate (0.10 mmol, 0.040 g, 57% yield) as a beige solid.

mp: 108-110° C.; LCMS (Method H), Rt=2.05 min, MS: (M+1)=369; $^1$H NMR (400 MHz, $CDCl_3$) δ ppm 1.69 (m, 2H) 1.78 (m, 2H) 2.23 (m, 2H) 2.36 (s, 3H) 2.52 (m, 2H) 3.72 (s, 3H) 3.90 (s, 3H) 6.40 (m, 1H) 6.46 (d, 1H) 7.09 (s, 1H) 7.19 (m, 2H) 7.36 (s, 1H) 7.74 (d, 1H)

Step 2:

To a solution of methyl (Z)-2-[5-[3-(cyclohexen-1-yl)pyrazol-1-yl]-2-methyl-phenoxy]-3-methoxy-prop-2-enoate (0.060 mmol, 0.022 g) in ethyl acetate (0.1 mol/L, 0.60 mL) and n-hexane (0.1 mol/L, 0.60 mL) at room temperature was added Pd/C (5% wt, 0.05 equiv., 0.006 g). The reaction mixture was purged with hydrogen gas using a balloon. The reaction mixture was stirred at room temperature until no more starting material was observed by LCMS. The black suspension was filtered through a pad of celite and silica and washed with EtOAc. The filtrate was concentrated in vacuo to give methyl (Z)-2-[5-(3-cyclohexylpyrazol-1-yl)-2-methyl-phenoxy]-3-methoxy-prop-2-enoate (0.049 mmol, 0.020 g, 81% yield) as a beige solid.

mp: 85-89° C.; LCMS (Method H), Rt=2.06 min, MS: (M+1)=371; $^1$H NMR (400 MHz, $CDCl_3$) δ ppm 1.39-1.50 (m, 4H) 1.54-1.59 (m, 1H) 1.72-1.79 (m, 1H) 1.80-1.88 (m, 2H) 2.02 (m, 2H) 2.37 (s, 3H) 2.71-2.82 (m, 1H) 3.73 (s, 3H) 3.91 (s, 3H) 6.24 (d, 1H) 7.05 (s, 1H) 7.19 (m, 2H) 7.37 (s, 1H) 7.72 (d, 1H)

TABLE E

Physical data of compounds of formula (I)

| Entry | Structure | Name | Rt (min) | Mass charge [M + H] | LCMS Method | mp (° C.) |
|---|---|---|---|---|---|---|
| E-1 | 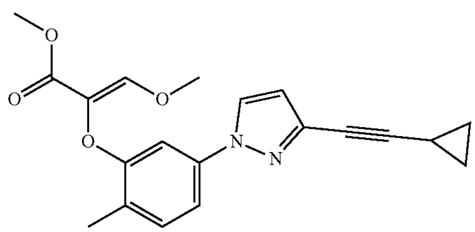 [SMILES: CO/C=C(\Oc1cc(-n2ccc(C#CC3CC3)n2)ccc1C)C(=O)OC] | methyl (Z)-2-[5-[3-(2-cyclopropylethynyl)pyrazol-1-yl]-2-methyl-phenoxy]-3-methoxy-prop-2-enoate | 1.57 | 353 | J | 158-162 |
| E-2 | 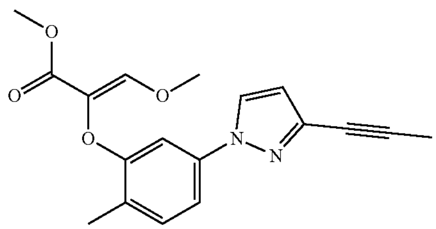 [SMILES: CC#Cc1ccn(-c2ccc(C)c(O/C(=C\OC)C(=O)OC)c2)n1] | methyl (Z)-3-methoxy-2-[2-methyl-5-(3-prop-1-ynylpyrazol-1-yl)phenoxy]prop-2-enoate | 1.51 | 327 | J | 175-179 |
| E-3 | 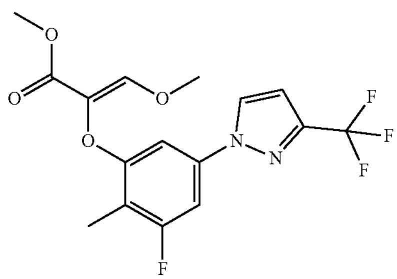 [SMILES: CO/C=C(\Oc1cc(-n2ccc(C(F)(F)F)n2)cc(F)c1C)C(=O)OC] | methyl (Z)-2-[3-fluoro-2-methyl-5-[3-(trifluoromethyl)pyrazol-1-yl]phenoxy]-3-methoxy-prop-2-enoate | 1.58 | 375 | J | 133-135 |
| E-4 | 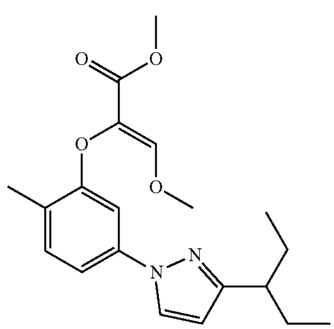 [SMILES: CCC(CC)c1ccn(-c2ccc(C)c(O/C(=C\OC)C(=O)OC)c2)n1] | methyl (Z)-2-[5-[3-(1-ethylpropyl)pyrazol-1-yl]-2-methyl-phenoxy]-3-methoxy-prop-2-enoate | 1.18 | 359 | G | 108-111 |
| E-5 | 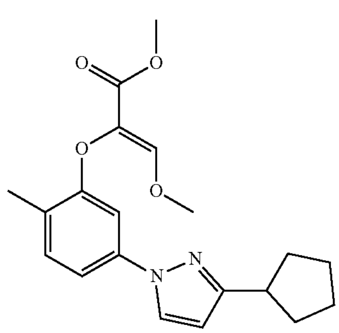 [SMILES: CO/C=C(\Oc1cc(-n2ccc(C3CCCC3)n2)ccc1C)C(=O)OC] | methyl (Z)-2-[5-(3-cyclopentylpyrazol-1-yl)-2-methyl-phenoxy]-3-methoxy-prop-2-enoate | 1.16 | 357 | G | |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-6 | 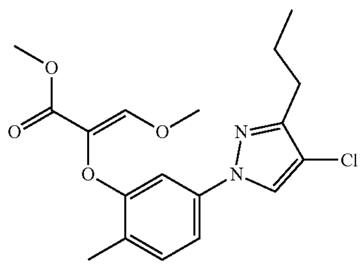 [SMILES: CCCc1nn(-c2ccc(C)c(O/C(=C\OC)C(=O)OC)c2)cc1Cl] | methyl (Z)-2-[5-(4-chloro-3-propyl-pyrazol-1-yl)-2-methyl-phenoxy]-3-methoxy-prop-2-enoate | 1.19 | 365 | G | |
| E-7 | 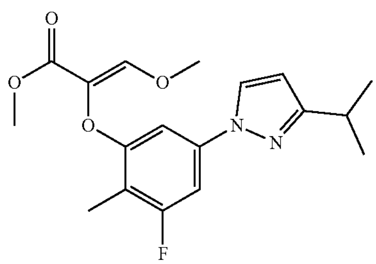 [SMILES: CO/C=C(\Oc1cc(-n2ccc(C(C)C)n2)cc(F)c1C)C(=O)OC] | methyl (Z)-2-[3-fluoro-5-(3-isopropylpyrazol-1-yl)-2-methyl-phenoxy]-3-methoxy-prop-2-enoate | 1.59 | 349 | J | 114-116 |
| E-9 | 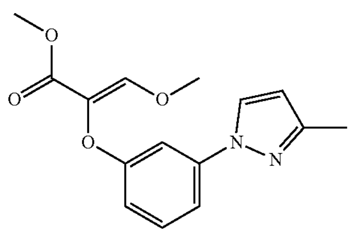 [SMILES: CO/C=C(\Oc1cccc(-n2ccc(C)n2)c1)C(=O)OC] | methyl (Z)-3-methoxy-2-[3-(3-methylpyrazol-1-yl)phenoxy]prop-2-enoate | 0.90 | 289 | G | |
| E-10 | 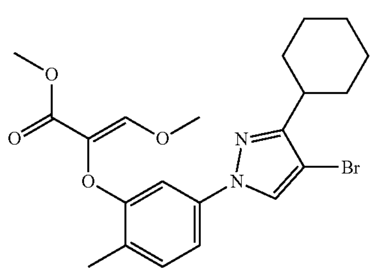 [SMILES: CO/C=C(\Oc1cc(-n2cc(Br)c(C3CCCCC3)n2)ccc1C)C(=O)OC] | methyl (Z)-2-[5-(4-bromo-3-cyclohexyl-pyrazol-1-yl)-2-methyl-phenoxy]-3-methoxy-prop-2-enoate | 1.32 | 451 | G | 120-126 |
| E-11 | 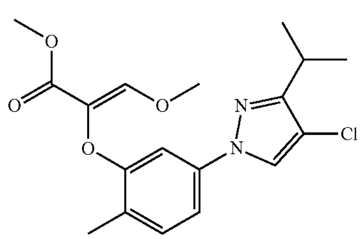 [SMILES: CO/C=C(\Oc1cc(-n2cc(Cl)c(C(C)C)n2)ccc1C)C(=O)OC] | methyl (Z)-2-[5-(4-chloro-3-isopropyl-pyrazol-1-yl)-2-methyl-phenoxy]-3-methoxy-prop-2-enoate | 1.20 | 365 | G | 95-100 |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-12 | 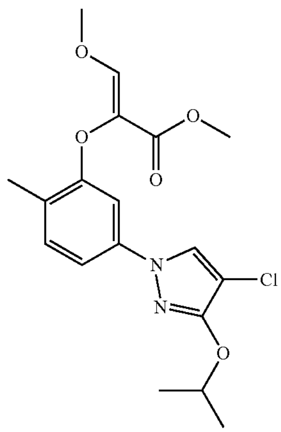 [SMILES: CO/C=C(\Oc1cc(-n2cc(Cl)c(OC(C)C)n2)ccc1C)C(=O)OC] | methyl (Z)-2-[5-(4-chloro-3-isopropoxy-pyrazol-1-yl)-2-methyl-phenoxy]-3-methoxy-prop-2-enoate | 1.17 | 381 | G | 104-107 |
| E-13 | 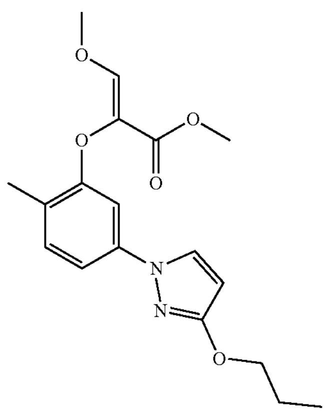 [SMILES: CCCOc1ccn(-c2ccc(C)c(O/C(=C\OC)C(=O)OC)c2)n1] | methyl (Z)-3-methoxy-2-[2-methyl-5-(3-propoxypyrazol-1-yl)phenoxy]prop-2-enoate | 1.56 | 347 | J | 85-87 |
| E-14 | 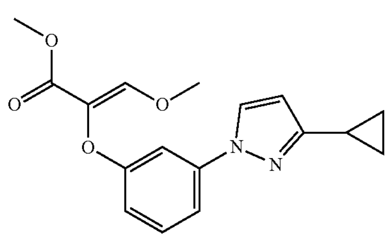 [SMILES: CO/C=C(\Oc1cccc(-n2ccc(C3CC3)n2)c1)C(=O)OC] | methyl (Z)-2-[3-(3-cyclopropylpyrazol-1-yl)phenoxy]-3-methoxy-prop-2-enoate | 0.98 | 315 | G | |
| E-15 | 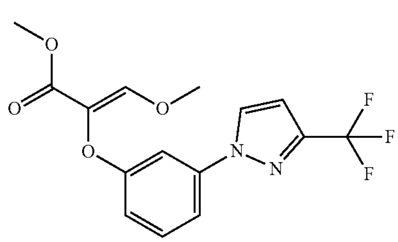 [SMILES: CO/C=C(\Oc1cccc(-n2ccc(C(F)(F)F)n2)c1)C(=O)OC] | methyl (Z)-3-methoxy-2-[3-[3-(trifluoromethyl)pyrazol-1-yl]phenoxy]prop-2-enoate | 1.02 | 343 | G | |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-16 | 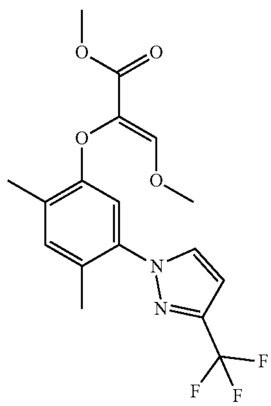 [SMILES: CO/C=C(\Oc1cc(-n2ccc(C(F)(F)F)n2)c(C)cc1C)C(=O)OC] | methyl (Z)-2-[2,4-dimethyl-5-[3-(trifluoromethyl)pyrazol-1-yl]phenoxy]-3-methoxy-prop-2-enoate | 1.56 | 371 | J | 96-98 |
| E-17 | 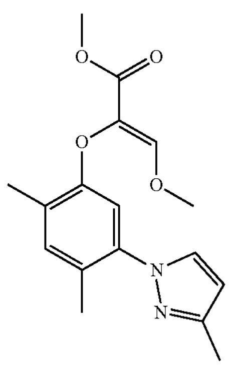 [SMILES: CO/C=C(\Oc1cc(-n2ccc(C)n2)c(C)cc1C)C(=O)OC] | methyl (Z)-2-[2,4-dimethyl-5-(3-methylpyrazol-1-yl)phenoxy]-3-methoxy-prop-2-enoate | 1.42 | 317 | J | 123-124 |
| E-18 | 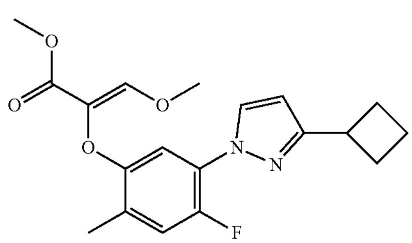 [SMILES: CO/C=C(\Oc1cc(-n2ccc(C3CCC3)n2)c(F)cc1C)C(=O)OC] | methyl (Z)-2-[5-(3-cyclobutylpyrazol-1-yl)-4-fluoro-2-methyl-phenoxy]-3-methoxy-prop-2-enoate | 1.89 | 361 | H | |
| E-19 | 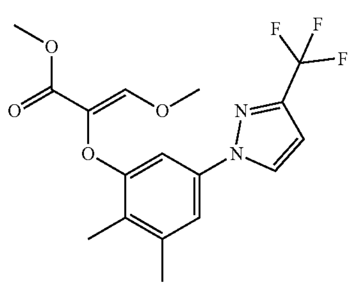 [SMILES: CO/C=C(\Oc1cc(-n2ccc(C(F)(F)F)n2)cc(C)c1C)C(=O)OC] | methyl (Z)-2-[2,3-dimethyl-5-[3-(trifluoromethyl)pyrazol-1-yl]phenoxy]-3-methoxy-prop-2-enoate | 1.56 | 371 | J | 144-146 |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-20 | 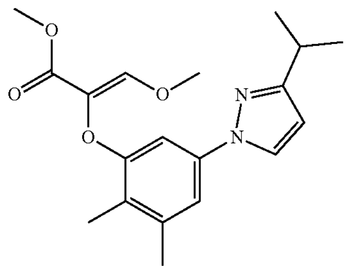 [SMILES: CO/C=C(\Oc1cc(-n2ccc(C(C)C)n2)cc(C)c1C)C(=O)OC] | methyl (Z)-2-[5-(3-isopropylpyrazol-1-yl)-2,3-dimethyl-phenoxy]-3-methoxy-prop-2-enoate | 1.56 | 345 | J | 103-105 |
| E-21 | 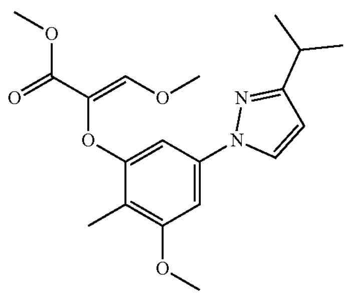 [SMILES: CO/C=C(\Oc1cc(-n2ccc(C(C)C)n2)cc(OC)c1C)C(=O)OC] | methyl (Z)-2-[5-(3-isopropylpyrazol-1-yl)-3-methoxy-2-methyl-phenoxy]-3-methoxy-prop-2-enoate | 1.56 | 361 | J | 90-92 |
| E-22 | 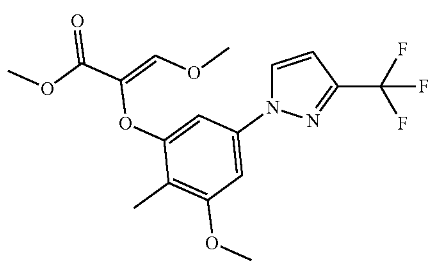 [SMILES: CO/C=C(\Oc1cc(-n2ccc(C(F)(F)F)n2)cc(OC)c1C)C(=O)OC] | methyl (Z)-3-methoxy-2-[3-methoxy-2-methyl-5-[3-(trifluoromethyl)pyrazol-1-yl]phenoxy]prop-2-enoate | 1.53 | 387 | J | 153-156 |
| E-23 | 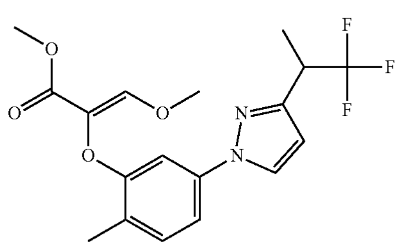 [SMILES: CO/C=C(\Oc1cc(-n2ccc(C(C)C(F)(F)F)n2)ccc1C)C(=O)OC] | methyl (Z)-3-methoxy-2-[2-methyl-5-[3-(2,2,2-trifluoro-1-methyl-ethyl)pyrazol-1-yl]phenoxy]prop-2-enoate | 1.82 | 385 | H | 119-122 |
| E-24 | 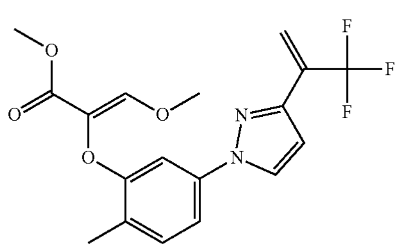 [SMILES: C=C(c1ccn(-c2ccc(C)c(O/C(=C\OC)C(=O)OC)c2)n1)C(F)(F)F] | methyl (Z)-3-methoxy-2-[2-methyl-5-[3-[1-(trifluoromethyl)vinyl]pyrazol-1-yl]phenoxy]prop-2-enoate | 1.87 | 383 | H | |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-25 | 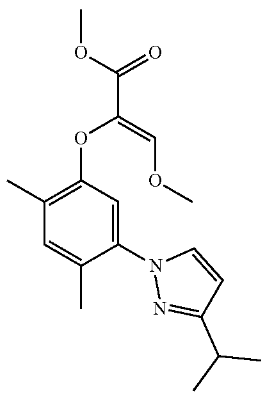 [SMILES: CO/C=C(\Oc1cc(-n2ccc(C(C)C)n2)c(C)cc1C)C(=O)OC] | methyl (Z)-2-[5-(3-isopropylpyrazol-1-yl)-2,4-dimethyl-phenoxy]-3-methoxy-prop-2-enoate | 1.54 | 345 | J | 96-98 |
| E-26 | 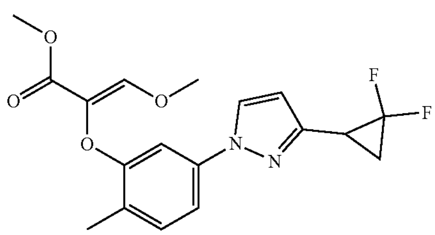 [SMILES: CO/C=C(\Oc1cc(-n2ccc(C3CC3(F)F)n2)ccc1C)C(=O)OC] | methyl (Z)-2-[5-[3-(2,2-difluorocyclopropyl)pyrazol-1-yl]-2-methyl-phenoxy]-3-methoxy-prop-2-enoate | 1.68 | 365 | H | |
| E-27 | 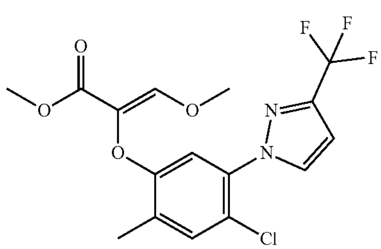 [SMILES: CO/C=C(\Oc1cc(-n2ccc(C(F)(F)F)n2)c(Cl)cc1C)C(=O)OC] | methyl (Z)-2-[4-chloro-2-methyl-5-[3-(trifluoromethyl)pyrazol-1-yl]phenoxy]-3-methoxy-prop-2-enoate | 1.59 | 391 | J | |
| E-28 | 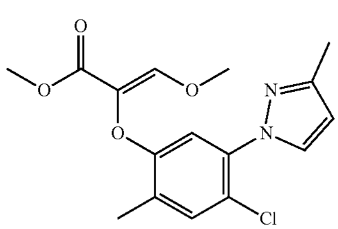 [SMILES: CO/C=C(\Oc1cc(-n2ccc(C)n2)c(Cl)cc1C)C(=O)OC] | methyl (Z)-2-[4-chloro-2-methyl-5-(3-methylpyrazol-1-yl)phenoxy]-3-methoxy-prop-2-enoate | 1.48 | 337 | J | |
| E-29 | 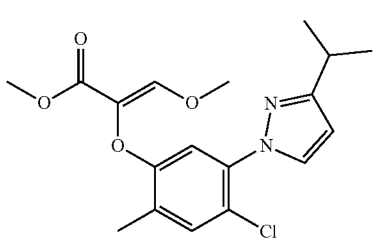 [SMILES: CO/C=C(\Oc1cc(-n2ccc(C(C)C)n2)c(Cl)cc1C)C(=O)OC] | methyl (Z)-2-[4-chloro-5-(3-isopropylpyrazol-1-yl)-2-methyl-phenoxy]-3-methoxy-prop-2-enoate | 1.58 | 365 | J | 96-98 |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-30 | 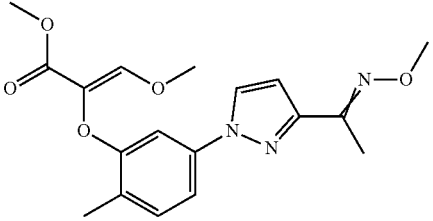 [SMILES: CO/C=C(\Oc1cc(-n2ccc(C(C)=NOC)n2)ccc1C)C(=O)OC] | methyl (Z)-3-methoxy-2-[5-[3-(N-methoxy-C-methyl-carbonimidoyl)pyrazol-1-yl]-2-methyl-phenoxy]prop-2-enoate | 1.72 1.75 | 360 | H | 130-133 |
| E-31 | 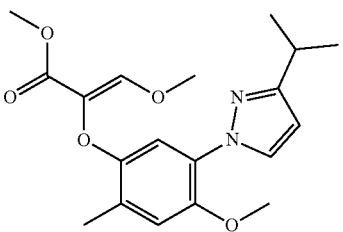 [SMILES: CO/C=C(\Oc1cc(-n2ccc(C(C)C)n2)c(OC)cc1C)C(=O)OC] | methyl (Z)-2-[5-(3-isopropylpyrazol-1-yl)-4-methoxy-2-methyl-phenoxy]-3-methoxy-prop-2-enoate | 1.56 | 361 | J | |
| E-32 | 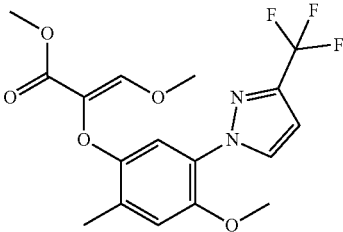 [SMILES: CO/C=C(\Oc1cc(-n2ccc(C(F)(F)F)n2)c(OC)cc1C)C(=O)OC] | methyl (Z)-3-methoxy-2-[4-methoxy-2-methyl-5-[3-(trifluoromethyl)pyrazol-1-yl]phenoxy]prop-2-enoate | 1.54 | 387 | J | 130-133 |
| E-33 | 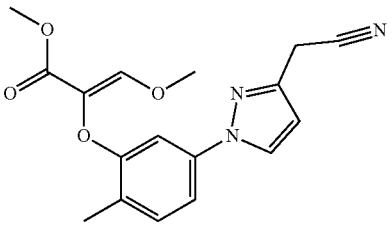 [SMILES: CO/C=C(\Oc1cc(-n2ccc(CC#N)n2)ccc1C)C(=O)OC] | methyl (Z)-2-[5-[3-(cyanomethyl)pyrazol-1-yl]-2-methyl-phenoxy]-3-methoxy-prop-2-enoate | 1.38 | 328 | H | 120-123 |
| E-34 | 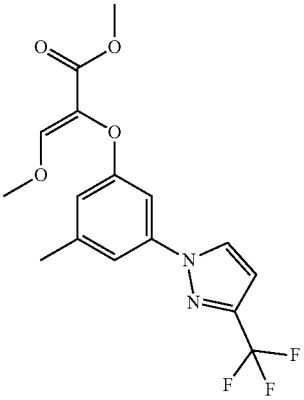 [SMILES: CO/C=C(\Oc1cc(C)cc(-n2ccc(C(F)(F)F)n2)c1)C(=O)OC] | methyl (Z)-3-methoxy-2-[3-methyl-5-[3-(trifluoromethyl)pyrazol-1-yl]phenoxy]prop-2-enoate | 1.54 | 357 | J | |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-35 | 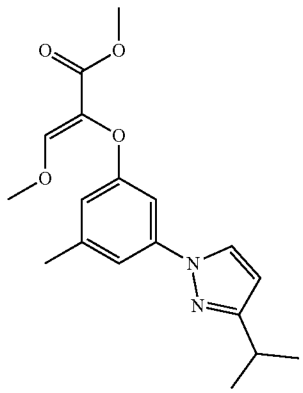 [SMILES: CO/C=C(\Oc1cc(C)cc(-n2ccc(C(C)C)n2)c1)C(=O)OC] | methyl (Z)-2-[3-(3-isopropylpyrazol-1-yl)-5-methyl-phenoxy]-3-methoxy-prop-2-enoate | 1.54 | 331 | J | |
| E-36 | 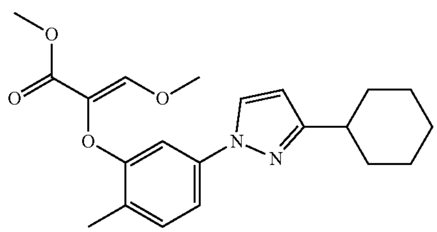 [SMILES: CO/C=C(\Oc1cc(-n2ccc(C3CCCCC3)n2)ccc1C)C(=O)OC] | methyl (Z)-2-[5-(3-cyclohexylpyrazol-1-yl)-2-methyl-phenoxy]-3-methoxy-prop-2-enoate | 2.06 | 371 | H | 85-89 |
| E-37 | 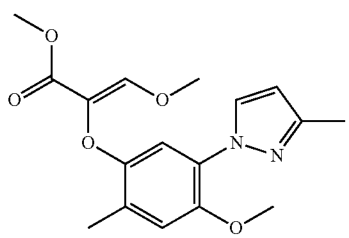 [SMILES: CO/C=C(\Oc1cc(-n2ccc(C)n2)c(OC)cc1C)C(=O)OC] | methyl (Z)-3-methoxy-2-[4-methoxy-2-methyl-5-(3-methylpyrazol-1-yl)phenoxy]prop-2-enoate | 1.40 | 333 | J | 99-101 |
| E-38 | 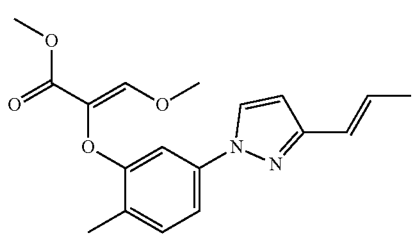 [SMILES: C/C=C/c1ccn(-c2ccc(C)c(O/C(=C\OC)C(=O)OC)c2)n1] | methyl (Z)-3-methoxy-2-[2-methyl-5-[3-[(E)-prop-1-enyl]pyrazol-1-yl]phenoxy]prop-2-enoate | 1.72 | 328 | H | 110-112 |
| E-39 | 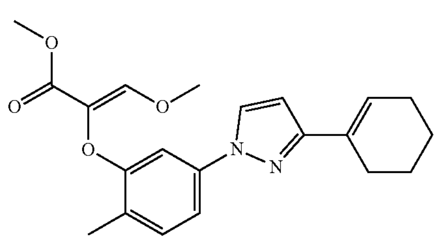 [SMILES: CO/C=C(\Oc1cc(-n2ccc(C3=CCCCC3)n2)ccc1C)C(=O)OC] | methyl (Z)-2-[5-[3-(cyclohexen-1-yl)pyrazol-1-yl]-2-methyl-phenoxy]-3-methoxy-prop-2-enoate | 2.05 | 369 | H | 108-110 |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-40 | 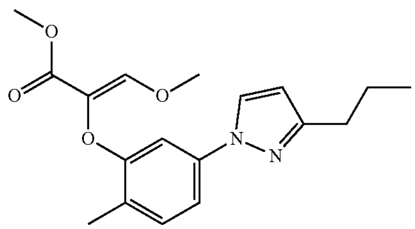 [SMILES: CCCc1ccn(-c2ccc(C)c(O/C(=C\OC)C(=O)OC)c2)n1] | methyl (Z)-3-methoxy-2-[2-methyl-5-(3-propylpyrazol-1-yl)phenoxy]prop-2-enoate | 1.77 | 331 | H | 91-94 |
| E-41 | 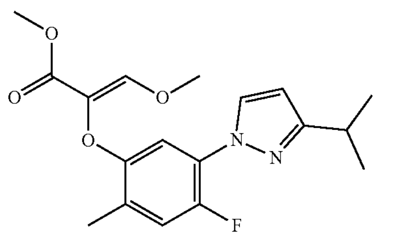 [SMILES: CO/C=C(\Oc1cc(-n2ccc(C(C)C)n2)c(F)cc1C)C(=O)OC] | methyl (Z)-2-[4-fluoro-5-(3-isopropylpyrazol-1-yl)-2-methyl-phenoxy]-3-methoxy-prop-2-enoate | 1.58 | 349 | J | |
| E-42 | 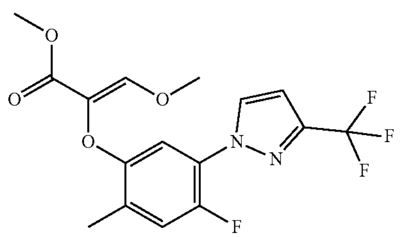 [SMILES: CO/C=C(\Oc1cc(-n2ccc(C(F)(F)F)n2)c(F)cc1C)C(=O)OC] | methyl (Z)-2-[4-fluoro-2-methyl-5-[3-(trifluoromethyl)pyrazol-1-yl]phenoxy]-3-methoxy-prop-2-enoate | 1.54 | 375 | J | 104-108 |
| E-43 | 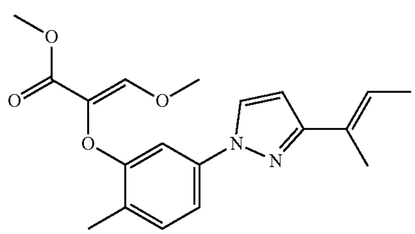 [SMILES: C/C=C(\C)c1ccn(-c2ccc(C)c(O/C(=C\OC)C(=O)OC)c2)n1] | methyl (Z)-3-methoxy-2-[2-methyl-5-[3-[(E)-1-methylprop-1-enyl]pyrazol-1-yl]phenoxy]prop-2-enoate | 1.90 | 343 | H | 115-118 |
| E-44 | 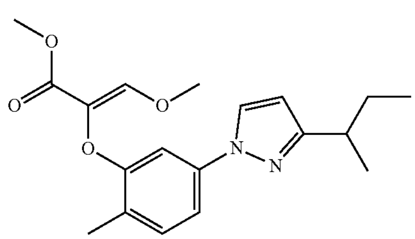 [SMILES: CCC(C)c1ccn(-c2ccc(C)c(O/C(=C\OC)C(=O)OC)c2)n1] | methyl (Z)-3-methoxy-2-[2-methyl-5-(3-sec-butylpyrazol-1-yl)phenoxy]prop-2-enoate | 1.90 | 345 | H | 110-113 |
| E-45 | 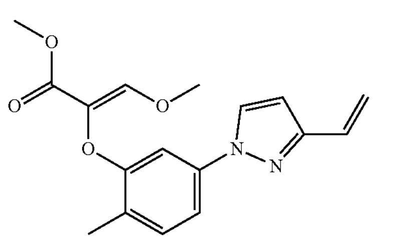 [SMILES: C=Cc1ccn(-c2ccc(C)c(O/C(=C\OC)C(=O)OC)c2)n1] | methyl (Z)-3-methoxy-2-[2-methyl-5-(3-vinylpyrazol-1-yl)phenoxy]prop-2-enoate | 1.61 | 315 | H | 114-117 |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-46 | 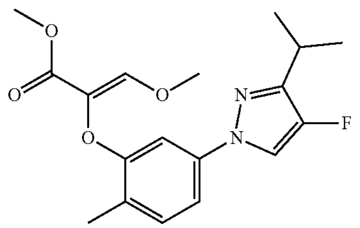 [SMILES: CO/C=C(\Oc1cc(-n2cc(F)c(C(C)C)n2)ccc1C)C(=O)OC] | methyl (Z)-2-[5-(4-fluoro-3-isopropyl-pyrazol-1-yl)-2-methyl-phenoxy]-3-methoxy-prop-2-enoate | 1.92 | 349 | H | 111-113 |
| E-47 | 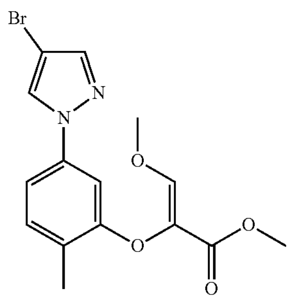 | methyl (Z)-2-[5-(4-bromopyrazol-1-yl)-2-methyl-phenoxy]-3-methoxy-prop-2-enoate | 1.65 | 366.97 | I | |
| E-48 | 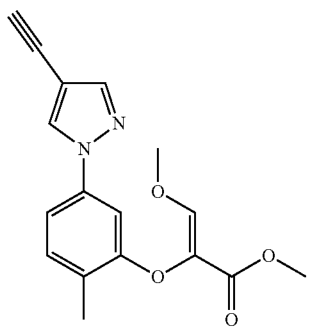 [SMILES: C#Cc1cnn(-c2ccc(C)c(O/C(=C\OC)C(=O)OC)c2)c1] | methyl (Z)-2-[5-(4-ethynylpyrazol-1-yl)-2-methyl-phenoxy]-3-methoxy-prop-2-enoate | 1.54 | 313.06 | I | |
| E-49 | 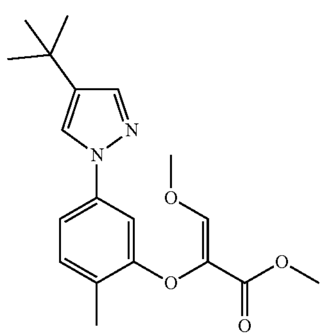 [SMILES: CO/C=C(\Oc1cc(-n2cc(C(C)(C)C)cn2)ccc1C)C(=O)OC] | methyl (Z)-2-[5-(4-tert-butylpyrazol-1-yl)-2-methyl-phenoxy]-3-methoxy-prop-2-enoate | 1.83 | 345.13 | I | |
| E-50 | 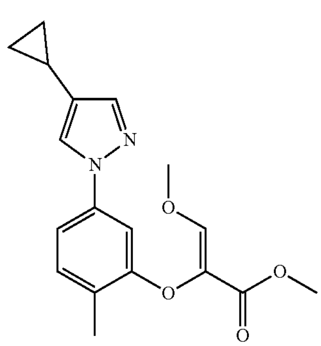 [SMILES: CO/C=C(\Oc1cc(-n2cc(C3CC3)cn2)ccc1C)C(=O)OC] | methyl (Z)-2-[5-(4-cyclopropylpyrazol-1-yl)-2-methyl-phenoxy]-3-methoxy-prop-2-enoate | 1.64 | 329.10 | I | |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-51 | 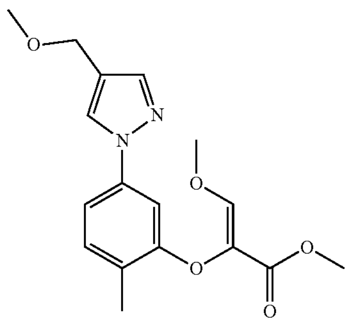 | methyl (Z)-3-methoxy-2-[5-[4-(methoxymethyl)pyrazol-1-yl]-2-methyl-phenoxy]prop-2-enoate | 1.37 | 333.09 | I | |
| E-52 | 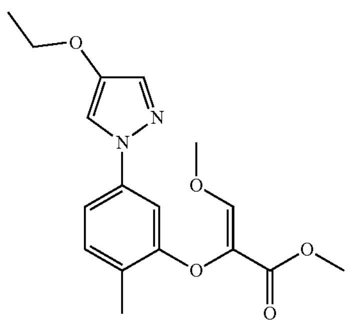 [SMILES: CCOc1cnn(-c2ccc(C)c(O/C(=C\OC)C(=O)OC)c2)c1] | methyl (Z)-2-[5-(4-ethoxypyrazol-1-yl)-2-methyl-phenoxy]-3-methoxy-prop-2-enoate | 1.54 | 333.07 | I | |
| E-53 | 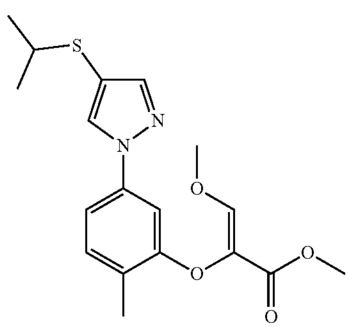 [SMILES: CO/C=C(\Oc1cc(-n2cc(SC(C)C)cn2)ccc1C)C(=O)OC] | methyl (Z)-2-[5-(4-isopropylsulfanylpyrazol-1-yl)-2-methyl-phenoxy]-3-methoxy-prop-2-enoate | 1.81 | 363.08 | I | |
| E-54 | 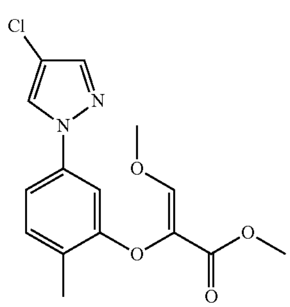 [SMILES: CO/C=C(\Oc1cc(-n2cc(Cl)cn2)ccc1C)C(=O)OC] | methyl (Z)-2-[5-(4-chloropyrazol-1-yl)-2-methyl-phenoxy]-3-methoxy-prop-2-enoate | 1.62 | 322.07 | I | |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-55 | 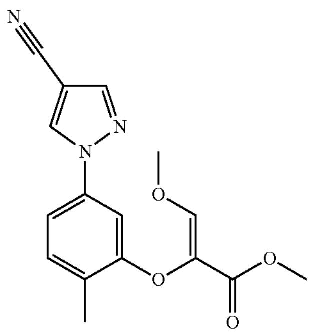 [SMILES: CO/C=C(\Oc1cc(-n2cc(C#N)cn2)ccc1C)C(=O)OC] | methyl (Z)-2-[5-(4-cyanopyrazol-1-yl)-2-methyl-phenoxy]-3-methoxy-prop-2-enoate | 1.42 | 314.07 | I | |
| E-56 | 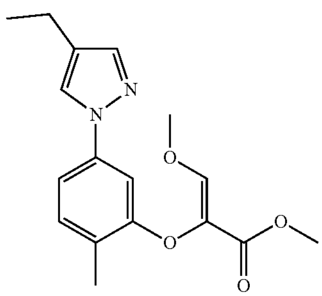 [SMILES: CCc1cnn(-c2ccc(C)c(O/C(=C\OC)C(=O)OC)c2)c1] | methyl (Z)-2-[5-(4-ethylpyrazol-1-yl)-2-methyl-phenoxy]-3-methoxy-prop-2-enoate | 1.63 | 317.08 | I | |
| E-57 | 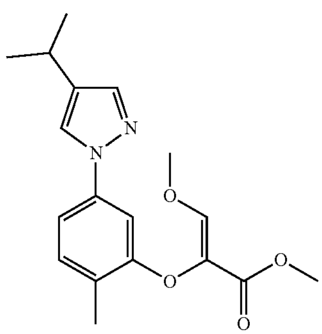 [SMILES: CO/C=C(\Oc1cc(-n2cc(C(C)C)cn2)ccc1C)C(=O)OC] | methyl (Z)-2-[5-(4-isopropylpyrazol-1-yl)-2-methyl-phenoxy]-3-methoxy-prop-2-enoate | 1.74 | 331.11 | I | |
| E-58 | 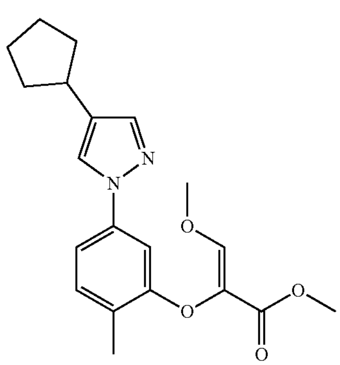 [SMILES: CO/C=C(\Oc1cc(-n2cc(C3CCCC3)cn2)ccc1C)C(=O)OC] | methyl (Z)-2-[5-(4-cyclopentylpyrazol-1-yl)-2-methyl-phenoxy]-3-methoxy-prop-2-enoate | 1.90 | 357.11 | I | |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-59 | 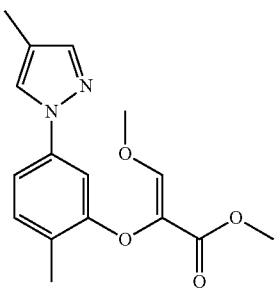 | methyl (Z)-3-methoxy-2-[2-methyl-5-(4-methylpyrazol-1-yl)phenoxy]prop-2-enoate | 1.50 | 303.03 | I | |
| E-60 | 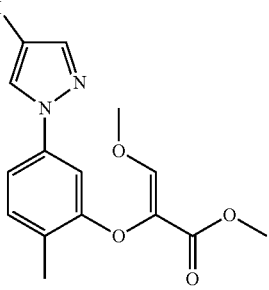 | methyl (Z)-2-[5-(4-iodopyrazol-1-yl)-2-methyl-phenoxy]-3-methoxy-prop-2-enoate | 1.69 | 414.98 | I | |
| E-61 | 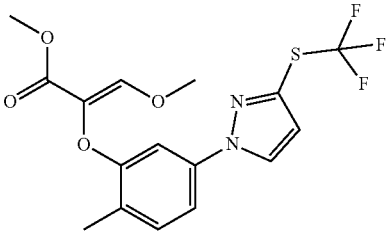 [SMILES: CO/C=C(\Oc1cc(-n2ccc(SC(F)(F)F)n2)ccc1C)C(=O)OC] | methyl (Z)-3-methoxy-2-[2-methyl-5-[3-(trifluoromethylsulfanyl)pyrazol-1-yl]phenoxy]prop-2-enoate | 1.88 | 389 | H | 137-139 |
| E-64 | 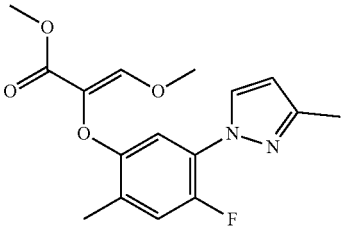 [SMILES: CO/C=C(\Oc1cc(-n2ccc(C)n2)c(F)cc1C)C(=O)OC] | methyl (Z)-2-[4-fluoro-2-methyl-5-(3-methylpyrazol-1-yl)phenoxy]-3-methoxy-prop-2-enoate | 1.43 | 321 | J | 134-138 |
| E-65 | 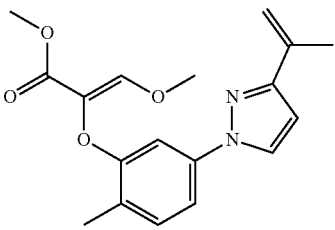 [SMILES: C=C(C)c1ccn(-c2ccc(C)c(O/C(=C\OC)C(=O)OC)c2)n1] | methyl (Z)-2-[5-(3-isopropenylpyrazol-1-yl)-2-methyl-phenoxy]-3-methoxy-prop-2-enoate | 1.81 | 329 | H | 80-84 |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-66 | 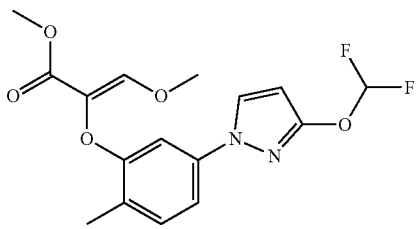 [SMILES: CO/C=C(\Oc1cc(-n2ccc(OC(F)F)n2)ccc1C)C(=O)OC] | methyl (Z)-2-[5-[3-(difluoromethoxy)pyrazol-1-yl]-2-methyl-phenoxy]-3-methoxy-prop-2-enoate | 1.67 | 355 | H | 123-126 |
| E-67 | 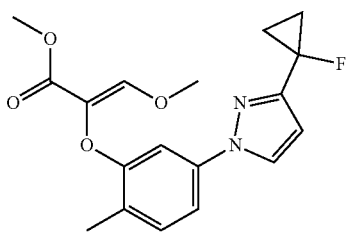 [SMILES: CO/C=C(\Oc1cc(-n2ccc(C3(F)CC3)n2)ccc1C)C(=O)OC] | methyl (Z)-2-[5-[3-(1-fluorocyclopropyl)pyrazol-1-yl]-2-methyl-phenoxy]-3-methoxy-prop-2-enoate | 1.73 | 347 | H | 128-131 |
| E-68 | 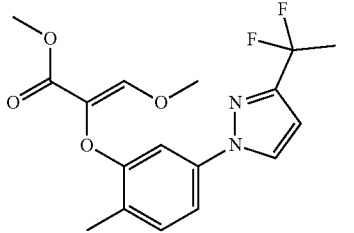 [SMILES: CO/C=C(\Oc1cc(-n2ccc(C(C)(F)F)n2)ccc1C)C(=O)OC] | methyl (Z)-2-[5-[3-(1,1-difluoroethyl)pyrazol-1-yl]-2-methyl-phenoxy]-3-methoxy-prop-2-enoate | 1.74 | 353 | H | 119-121 |
| E-69 | 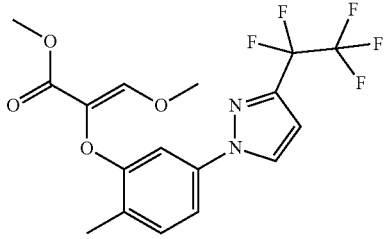 [SMILES: CO/C=C(\Oc1cc(-n2ccc(C(F)(F)C(F)(F)F)n2)ccc1C)C(=O)OC] | methyl (Z)-3-methoxy-2-[2-methyl-5-[3-(1,1,2,2,2-pentafluoroethyl)pyrazol-1-yl]phenoxy]prop-2-enoate | 1.94 | 407 | H | 117-120 |
| E-70 | 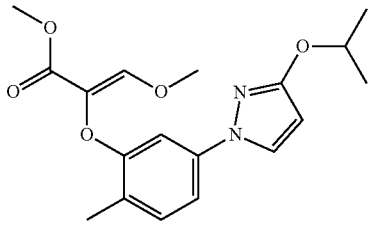 [SMILES: CO/C=C(\Oc1cc(-n2ccc(OC(C)C)n2)ccc1C)C(=O)OC] | methyl (Z)-2-[5-(3-isopropoxypyrazol-1-yl)-2-methyl-phenoxy]-3-methoxy-prop-2-enoate | 1.78 | 347 | H | 94-97 |
| E-75 | 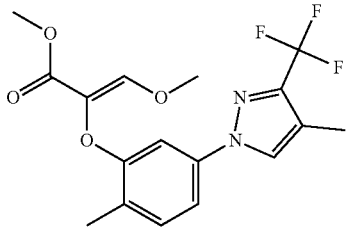 [SMILES: CO/C=C(\Oc1cc(-n2cc(C)c(C(F)(F)F)n2)ccc1C)C(=O)OC] | methyl (Z)-3-methoxy-2-[2-methyl-5-[4-methyl-3-(trifluoromethyl)pyrazol-1-yl]phenoxy]prop-2-enoate | 1.88 | 371 | H | 131-134 |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-76 | 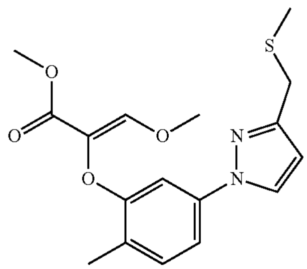 [SMILES: CO/C=C(\Oc1cc(-n2ccc(CSC)n2)ccc1C)C(=O)OC] | methyl (Z)-3-methoxy-2-[2-methyl-5-[3-(methylsulfanylmethyl)pyrazol-1-yl]phenoxy]prop-2-enoate | 1.61 | 349 | H | 78-80 |
| E-77 | 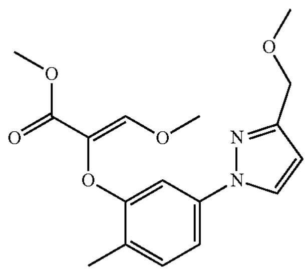 [SMILES: CO/C=C(\Oc1cc(-n2ccc(COC)n2)ccc1C)C(=O)OC] | methyl (Z)-3-methoxy-2-[5-[3-(methoxymethyl)pyrazol-1-yl]-2-methyl-phenoxy]prop-2-enoate | 1.41 | 333 | H | 107-110 |
| E-78 | 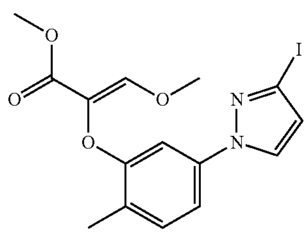 [SMILES: CO/C=C(\Oc1cc(-n2ccc(I)n2)ccc1C)C(=O)OC] | methyl (Z)-2-[5-(3-iodopyrazol-1-yl)-2-methyl-phenoxy]-3-methoxy-prop-2-enoate | 1.69 | 415 | H | 156-159 |
| E-80 | 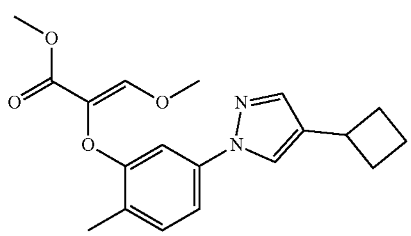 [SMILES: CO/C=C(\Oc1cc(-n2cc(C3CCC3)cn2)ccc1C)C(=O)OC] | methyl (Z)-2-[5-(4-cyclobutylpyrazol-1-yl)-2-methyl-phenoxy]-3-methoxy-prop-2-enoate | 1.82 | 343 | H | |
| E-81 | 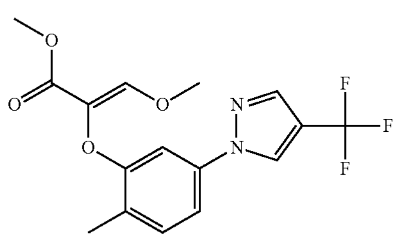 [SMILES: CO/C=C(\Oc1cc(-n2cc(C(F)(F)F)cn2)ccc1C)C(=O)OC] | methyl (Z)-3-methoxy-2-[2-methyl-5-[4-(trifluoromethyl)pyrazol-1-yl]phenoxy]prop-2-enoate | 1.75 | 357 | H | 102-105 |
| E-82 | 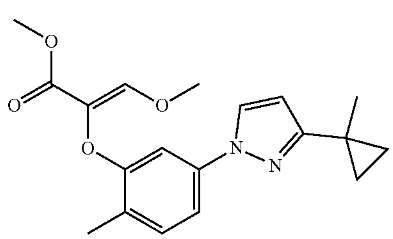 [SMILES: CO/C=C(\Oc1cc(-n2ccc(C3(C)CC3)n2)ccc1C)C(=O)OC] | methyl (Z)-3-methoxy-2-[2-methyl-5-[3-(1-methylcyclopropyl)pyrazol-1-yl]phenoxy]prop-2-enoate | 1.85 | 343 | H | 83-86 |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-83 | 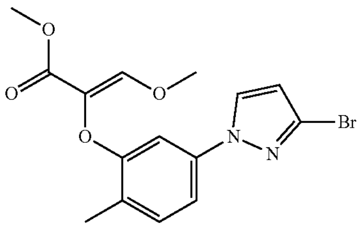 [SMILES: CO/C=C(\Oc1cc(-n2ccc(Br)n2)ccc1C)C(=O)OC] | methyl (Z)-2-[5-(3-bromopyrazol-1-yl)-2-methyl-phenoxy]-3-methoxy-prop-2-enoate | 1.64 | 367/369 | H | 106-110 |
| E-84 | 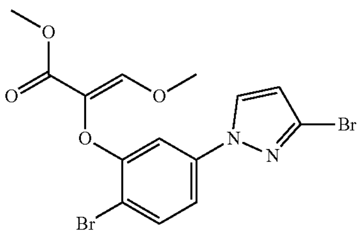 [SMILES: CO/C=C(\Oc1cc(-n2ccc(Br)n2)ccc1Br)C(=O)OC] | methyl (Z)-2-[2-bromo-5-(3-bromopyrazol-1-yl)phenoxy]-3-methoxy-prop-2-enoate | 1.04 | 431/433/435 | G | |
| E-85 | 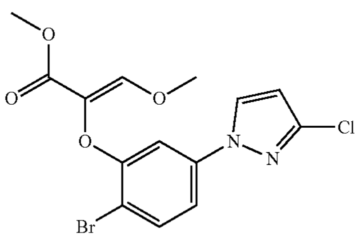 [SMILES: CO/C=C(\Oc1cc(-n2ccc(Cl)n2)ccc1Br)C(=O)OC] | methyl (Z)-2-[2-bromo-5-(3-chloropyrazol-1-yl)phenoxy]-3-methoxy-prop-2-enoate | 1.03 | 387/389 | G | |
| E-86 | 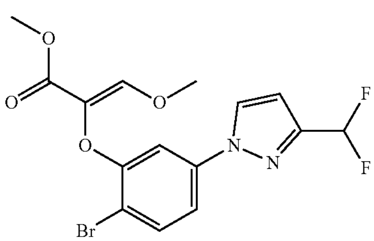 [SMILES: CO/C=C(\Oc1cc(-n2ccc(C(F)F)n2)ccc1Br)C(=O)OC] | methyl (Z)-2-[2-bromo-5-[3-(difluoromethyl)pyrazol-1-yl]phenoxy]-3-methoxy-prop-2-enoate | 1.01 | 403/405 | G | |
| E-87 | 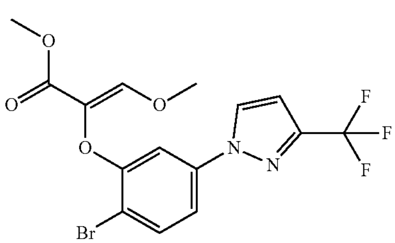 | methyl (Z)-2-[2-bromo-5-[3-(trifluoromethyl)pyrazol-1-yl]phenoxy]-3-methoxy-prop-2-enoate | 1.08 | 421/423 | G | |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-88 | 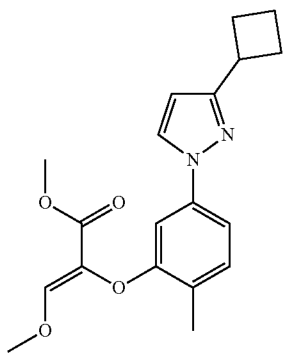 [SMILES: CO/C=C(\Oc1cc(-n2ccc(C3CCC3)n2)ccc1C)C(=O)OC] | methyl (Z)-2-[5-(3-cyclobutylpyrazol-1-yl)-2-methyl-phenoxy]-3-methoxy-prop-2-enoate | 1.76 | 343.25 | I | 91-94 |
| E-89 | 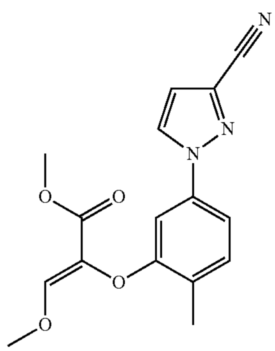 [SMILES: CO/C=C(\Oc1cc(-n2ccc(C#N)n2)ccc1C)C(=O)OC] | methyl (Z)-2-[5-(3-cyanopyrazol-1-yl)-2-methyl-phenoxy]-3-methoxy-prop-2-enoate | 1.47 | 314.2 | I | |
| E-90 | 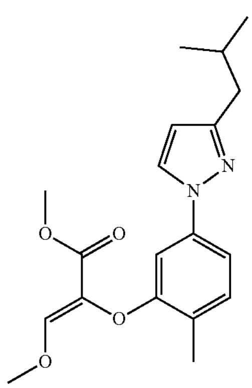 [SMILES: CO/C=C(\Oc1cc(-n2ccc(CC(C)C)n2)ccc1C)C(=O)OC] | methyl (Z)-2-[5-(3-isobutylpyrazol-1-yl)-2-methyl-phenoxy]-3-methoxy-prop-2-enoate | 1.82 | 345.27 | I | 76-80 |
| E-91 | 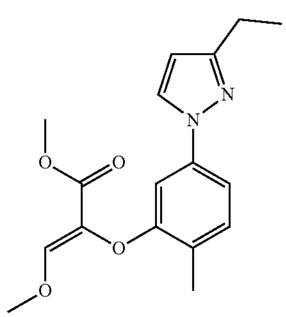 [SMILES: CCc1ccn(-c2ccc(C)c(O/C(=C\OC)C(=O)OC)c2)n1] | methyl (Z)-2-[5-(3-ethylpyrazol-1-yl)-2-methyl-phenoxy]-3-methoxy-prop-2-enoate | 1.57 | 317.24 | I | |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-92 | 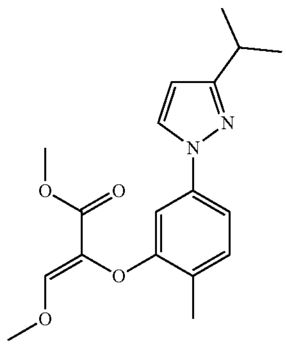 [SMILES: CO/C=C(\Oc1cc(-n2ccc(C(C)C)n2)ccc1C)C(=O)OC] | methyl (Z)-2-[5-(3-isopropylpyrazol-1-yl)-2-methyl-phenoxy]-3-methoxy-prop-2-enoate | 1.72 | 331.26 | I | 88-91 |
| E-94 | 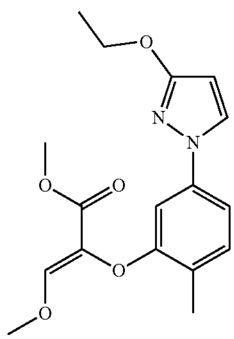 [SMILES: CCOc1ccn(-c2ccc(C)c(O/C(=C\OC)C(=O)OC)c2)n1] | methyl (Z)-2-[5-(3-ethoxypyrazol-1-yl)-2-methyl-phenoxy]-3-methoxy-prop-2-enoate | 1.59 | 333.23 | I | 94-96 |
| E-95 | 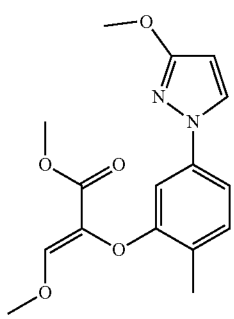 [SMILES: CO/C=C(\Oc1cc(-n2ccc(OC)n2)ccc1C)C(=O)OC] | methyl (Z)-3-methoxy-2-[5-(3-methoxypyrazol-1-yl)-2-methyl-phenoxy]prop-2-enoate | 1.47 | 319.21 | I | 120-123 |
| E-96 | 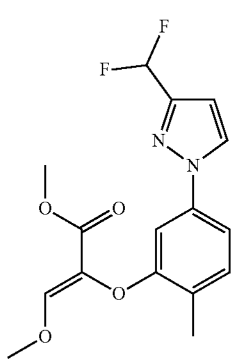 [SMILES: CO/C=C(\Oc1cc(-n2ccc(C(F)F)n2)ccc1C)C(=O)OC] | methyl (Z)-2-[5-[3-(difluoromethyl)pyrazol-1-yl]-2-methyl-phenoxy]-3-methoxy-prop-2-enoate | 1.53 | 339.19 | I | |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-97 | 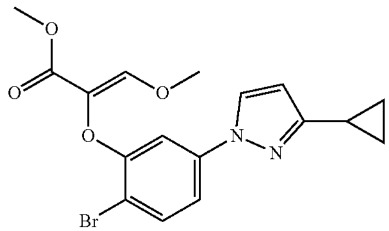 [SMILES: CO/C=C(\Oc1cc(-n2ccc(C3CC3)n2)ccc1Br)C(=O)OC] | methyl (Z)-2-[2-bromo-5-(3-cyclopropylpyrazol-1-yl)phenoxy]-3-methoxy-prop-2-enoate | 1.01 | 393/395 | G | |
| E-98 | 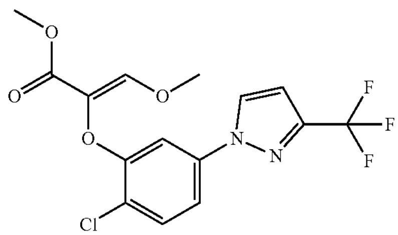 [SMILES: CO/C=C(\Oc1cc(-n2ccc(C(F)(F)F)n2)ccc1Cl)C(=O)OC] | methyl (Z)-2-[2-chloro-5-[3-(trifluoromethyl)pyrazol-1-yl]phenoxy]-3-methoxy-prop-2-enoate | 1.06 | 377/379 | G | |
| E-99 | 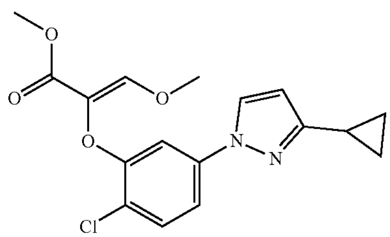 [SMILES: CO/C=C(\Oc1cc(-n2ccc(C3CC3)n2)ccc1Cl)C(=O)OC] | methyl (Z)-2-[2-chloro-5-(3-cyclopropylpyrazol-1-yl)phenoxy]-3-methoxy-prop-2-enoate | 1.03 | 349/351 | G | |
| E-100 | 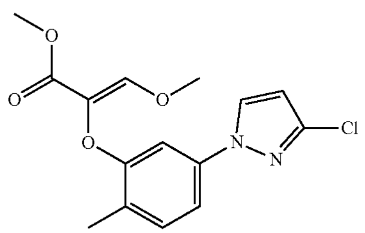 [SMILES: CO/C=C(\Oc1cc(-n2ccc(Cl)n2)ccc1C)C(=O)OC] | methyl (Z)-2-[5-(3-chloropyrazol-1-yl)-2-methyl-phenoxy]-3-methoxy-prop-2-enoate | 1.02 | 323/325 | G | 150-152 |
| E-101 | 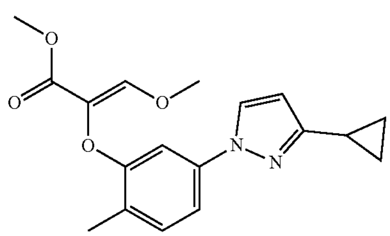 [SMILES: CO/C=C(\Oc1cc(-n2ccc(C3CC3)n2)ccc1C)C(=O)OC] | methyl (Z)-2-[5-(3-cyclopropylpyrazol-1-yl)-2-methyl-phenoxy]-3-methoxy-prop-2-enoate | 1.03 | 329 | G | 115-118 |
| E-103 | 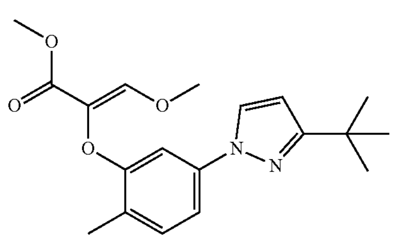 [SMILES: CO/C=C(\Oc1cc(-n2ccc(C(C)(C)C)n2)ccc1C)C(=O)OC] | methyl (Z)-2-[5-(3-tert-butylpyrazol-1-yl)-2-methyl-phenoxy]-3-methoxy-prop-2-enoate | 1.13 | 345 | G | |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-104 | 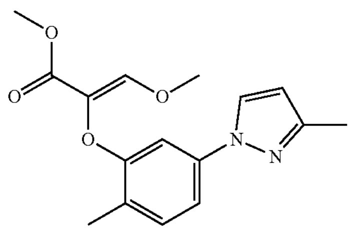 [SMILES: CO/C=C(\Oc1cc(-n2ccc(C)n2)ccc1C)C(=O)OC] | methyl (Z)-3-methoxy-2-[2-methyl-5-(3-methylpyrazol-1-yl)phenoxy]prop-2-enoate | 0.95 | 303 | G | |
| E-105 | 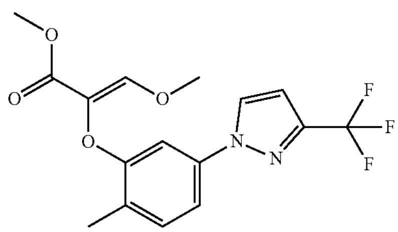 [SMILES: CO/C=C(\Oc1cc(-n2ccc(C(F)(F)F)n2)ccc1C)C(=O)OC] | methyl (Z)-3-methoxy-2-[2-methyl-5-[3-(trifluoromethyl)pyrazol-1-yl]phenoxy]prop-2-enoate | 1.07 | 357 | G | 154-156 |
| E-106 | 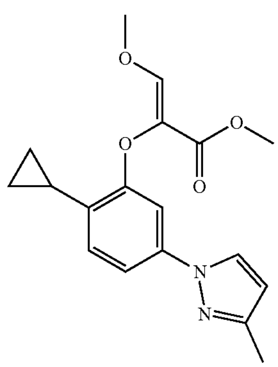 [SMILES: CO/C=C(\Oc1cc(-n2ccc(C)n2)ccc1C1CC1)C(=O)OC] | methyl (Z)-2-[2-cyclopropyl-5-(3-methylpyrazol-1-yl)phenoxy]-3-methoxy-prop-2-enoate | | | | 189-191 |
| E-107 | 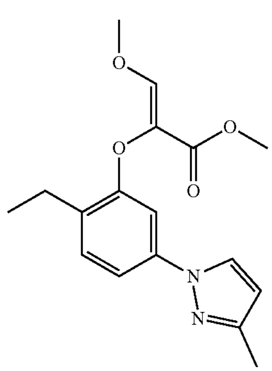 [SMILES: CCc1ccc(-n2ccc(C)n2)cc1O/C(=C\OC)C(=O)OC] | methyl (Z)-2-[2-ethyl-5-(3-methylpyrazol-1-yl)phenoxy]-3-methoxy-prop-2-enoate | | | | 169-171 |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-108 | 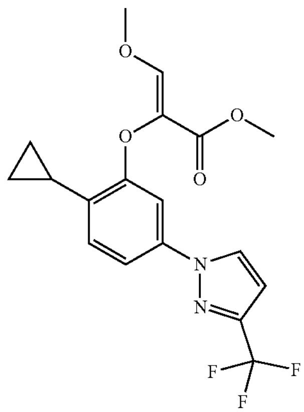 [SMILES: CO/C=C(\Oc1cc(-n2ccc(C(F)(F)F)n2)ccc1C1CC1)C(=O)OC] | methyl (Z)-2-[2-cyclopropyl-5-[3-(trifluoromethyl)pyrazol-1-yl]phenoxy]-3-methoxy-prop-2-enoate | | | | 130-132 |
| E-109 | 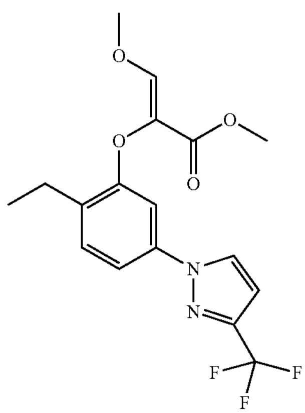 [SMILES: CCc1ccc(-n2ccc(C(F)(F)F)n2)cc1O/C(=C\OC)C(=O)OC] | methyl (Z)-2-[2-ethyl-5-[3-(trifluoromethyl)pyrazol-1-yl]phenoxy]-3-methoxy-prop-2-enoate | | | | 135-137 |
| E-110 | 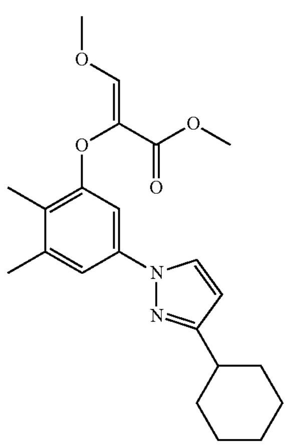 [SMILES: CO/C=C(\Oc1cc(-n2ccc(C3CCCCC3)n2)cc(C)c1C)C(=O)OC] | methyl (Z)-2-[5-(3-cyclohexylpyrazol-1-yl)-2,3-dimethyl-phenoxy]-3-methoxy-prop-2-enoate | | | | 90-93 |

TABLE E-continued
Physical data of compounds of formula (I)
| Entry | Structure | Name | Rt (min) | Mass charge [M + H] | LCMS Method | mp (° C.) |
|---|---|---|---|---|---|---|
| E-111 | 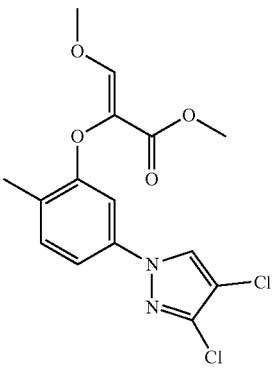 [SMILES: CO/C=C(\Oc1cc(-n2cc(Cl)c(Cl)n2)ccc1C)C(=O)OC] | methyl (Z)-2-[5-(3,4-dichloropyrazol-1-yl)-2-methyl-phenoxy]-3-methoxy-prop-2-enoate | | | | 140-144 |
| E-112 | 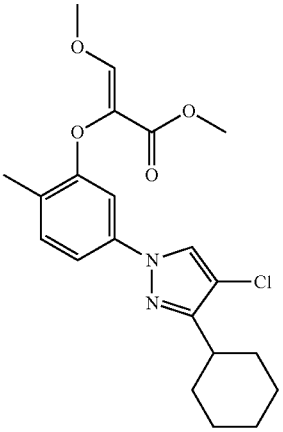 [SMILES: CO/C=C(\Oc1cc(-n2cc(Cl)c(C3CCCCC3)n2)ccc1C)C(=O)OC] | methyl (Z)-2-[5-(4-chloro-3-cyclohexyl-pyrazol-1-yl)-2-methyl-phenoxy]-3-methoxy-prop-2-enoate | | | | 150-152 |
| E-113 | 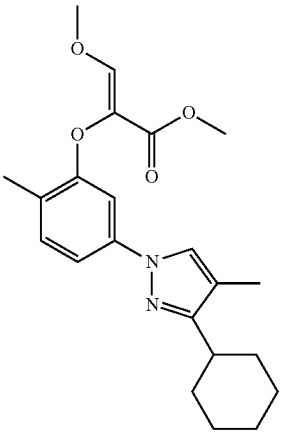 [SMILES: CO/C=C(\Oc1cc(-n2cc(C)c(C3CCCCC3)n2)ccc1C)C(=O)OC] | methyl (Z)-2-[5-(3-cyclohexyl-4-methyl-pyrazol-1-yl)-2-methyl-phenoxy]-3-methoxy-prop-2-enoate | | | | 145-148 |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-114 | 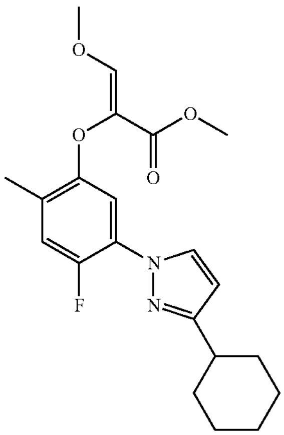 [SMILES: CO/C=C(\Oc1cc(-n2ccc(C3CCCCC3)n2)c(F)cc1C)C(=O)OC] | methyl (Z)-2-[5-(3-cyclohexylpyrazol-1-yl)-4-fluoro-2-methyl-phenoxy]-3-methoxy-prop-2-enoate | | | | |
| E-115 | 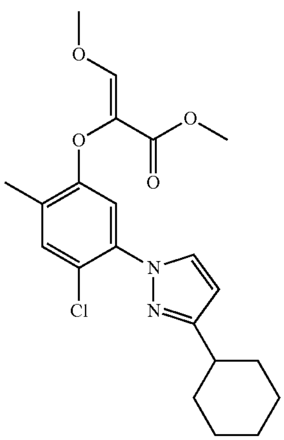 [SMILES: CO/C=C(\Oc1cc(-n2ccc(C3CCCCC3)n2)c(Cl)cc1C)C(=O)OC] | methyl (Z)-2-[4-chloro-5-(3-cyclohexylpyrazol-1-yl)-2-methyl-phenoxy]-3-methoxy-prop-2-enoate | | | | 127-129 |
| E-116 | 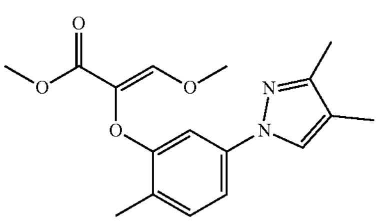 | methyl (Z)-2-[5-(3,4-dimethylpyrazol-1-yl)-2-methyl-phenoxy]-3-methoxy-prop-2-enoate | | | | 155-157 |
| E-117 | 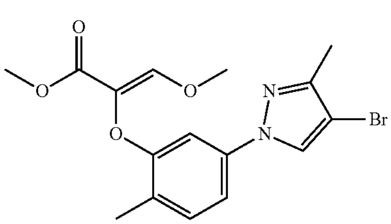 [SMILES: CO/C=C(\Oc1cc(-n2cc(Br)c(C)n2)ccc1C)C(=O)OC] | methyl (Z)-2-[5-(4-bromo-3-methyl-pyrazol-1-yl)-2-methyl-phenoxy]-3-methoxy-prop-2-enoate | | | | 120-122 |

TABLE E-continued

Physical data of compounds of formula (I)

| Entry | Structure | Name | Rt (min) | Mass charge [M + H] | LCMS Method | mp (° C.) |
|---|---|---|---|---|---|---|
| E-118 | 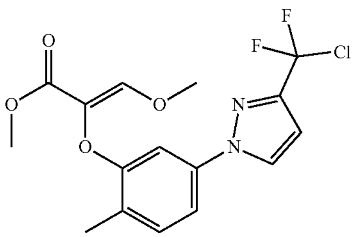 [SMILES: CO/C=C(\Oc1cc(-n2ccc(C(F)(F)Cl)n2)ccc1C)C(=O)OC] | methyl (Z)-2-[5-[3-[chloro(difluoro)methyl]pyrazol-1-yl]-2-methyl-phenoxy]-3-methoxy-prop-2-enoate | | | | 146-148 |

TABLE F

Physical data of compounds of formula (I)

| Entry | Structure | Name | Rt (min) | Mass charge [M + H] | LCMS Method | mp (° C.) |
|---|---|---|---|---|---|---|
| F-1 | | methyl (Z)-2-[5-(4-bromotriazol-2-yl)-2-methyl-phenoxy]-3-methoxy-prop-2-enoate | 1.10 | 368, 370 | G | |
| F-2 | | methyl (Z)-3-methoxy-2-[2-methyl-5-(4-propyltriazol-2-yl)phenoxy]prop-2-enoate | 1.15 | 332 | G | |

TABLE F-continued

Physical data of compounds of formula (I)

| Entry | Structure | Name | Rt (min) | Mass charge [M + H] | LCMS Method | mp (° C.) |
|---|---|---|---|---|---|---|
| F-3 | | methyl (Z)-2-[5-(4-butyltriazol-2-yl)-2-methyl-phenoxy]-3-methoxy-prop-2-enoate | | | | 68-70 |
| F-4 | | methyl (Z)-2-[5-(4-isopropyltriazol-2-yl)-2-methyl-phenoxy]-3-methoxy-prop-2-enoate | 1.14 | 332 | G | |
| F-5 | | methyl (Z)-2-[5-(4-cyclopentyltriazol-2-yl)-2-methyl-phenoxy]-3-methoxy-prop-2-enoate | 1.22 | 358 | G | |
| F-6 | | methyl (Z)-3-methoxy-2-[2-methyl-5-[4-(trifluoromethyl)triazol-2-yl]phenoxy]prop-2-enoate | | | | 107-109 |

TABLE F-continued

Physical data of compounds of formula (I)

| Entry | Name | Structure | Rt (min) | Mass charge [M + H] | LCMS Method | mp (° C.) |
|---|---|---|---|---|---|---|
| F-7 | methyl (Z)-2-[5-(4-cyclohexyltriazol-2-yl)-2-methyl-phenoxy]-3-methoxy-prop-2-enoate | | | | | 120-122 |
| F-8 | methyl (Z)-2-[5-(4-cyclopropyltriazol-2-yl)-2-methyl-phenoxy]-3-methoxy-prop-2-enoate | | 1.07 | 30 | G | |
| F-9 | methyl (Z)-2-[3-(4-cyclopropyltriazol-2-yl)phenoxy]-3-methoxy-prop-2-enoate | | 1.01 | 316 | G | |
| F-10 | methyl (Z)-2-[5-(4,5-dibromotriazol-2-yl)-2-methyl-phenoxy]-3-methoxy-prop-2-enoate | | 1.20 | 446, 448, 450 | G | |
| F-11 | methyl (Z)-2-[5-(4-isopropenyltriazol-2-yl)-2-methyl-phenoxy]-3-methoxy-prop-2-enoate | | 1.15 | 330 | G | |
| F-12 | methyl (Z)-2-[5-[4-(N-ethoxy-C-methyl-carbonimidoyl)triazol-2-yl]-2-methyl-phenoxy]-3-methoxy-prop-2-enoate | | | | | 113-116 |

TABLE F-continued

Physical data of compounds of formula (I)

| Entry | Structure | Name | Rt (min) | Mass charge [M + H] | LCMS Method | mp (° C.) |
|---|---|---|---|---|---|---|
| F-13 | | methyl (Z)-2-[5-[4-(N-hydroxy-C-methyl-carbonimidoyl)triazol-2-yl]-2-methyl-phenoxy]-3-methoxy-prop-2-enoate | | | | 146-150 |

Example B: Biological Examples/Test Methods

Example B1: *Alternaria solani*/Tomato/Leaf Disc (Early Blight)

Tomato leaf disks cv. Baby are placed on agar in multiwell plates (24-well format) and sprayed with the formulated test compound diluted in water. The leaf disks are inoculated with a spore suspension of the fungus 2 days after application. The inoculated leaf disks are incubated at 23° C./21° C. (day/night) and 80% rh (relative humidity) under a light regime of 12/12 h (light/dark) in a climate cabinet and the activity of a compound is assessed as percent disease control compared to untreated when an appropriate level of disease damage appears on untreated check disk leaf disks (5-7 days after application).

The following compounds gave at least 80% control of *Alternaria solani* at 200 ppm when compared to untreated control under the same conditions, which showed extensive disease development:

E-1, E-15, E-16, E-17, E-21, E-27, E-29, E-30, E-34, E-36, E-39, E-57, E-58, E-60, E-64, E-67, E-68, E-70, E-80, E-82, E-83, E-85, E-88, E-98, E-99, E-105, E-113, F-1, F-2, F-4, F-5, F-10, F-13

Example B2: *Botryotinia fuckeliana* (*Botrytis cinerea*)/Liquid Culture (Gray Mould)

Conidia of the fungus from cryogenic storage are directly mixed into nutrient broth (Vogels broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

The following compounds gave at least 80% control of *Botryotinia fuckeliana* at 20 ppm when compared to untreated control under the same conditions, which showed extensive disease development:

E-5, E-6, E-16, E-23, E-24, E-25, E-29, E-30, E-31, E-32, E-33, E-34, E-35, E-36, E-37, E-38, E-39, E-40, E-42, E-43, E-44, E-46, E-47, E-48, E-49, E-50, E-51, E-52, E-53, E-54, E-55, E-57, E-58, E-59, E-60, E-61, E-64, E-65, E-66, E-75, E-80, E-81, E-82, E-85, E-86, E-87, E-88, E-90, E-91, E-92, E-94, E-95, E-96, E-97, E-98, E-99, E-100, E-101, E-103, E-104, E-105, E-116, F-8

Example B3: *Glomerella lagenarium* (*Colletotrichum lagenarium*)/Liquid Culture (Anthracnose)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3-4 days after application.

The following compounds gave at least 80% control of *Glomerella lagenarium* at 20 ppm when compared to untreated control under the same conditions, which showed extensive disease development:

E-5, E-6, E-7, E-12, E-14, E-15, E-16, E-18, E-19, E-20, E-21, E-23, E-24, E-25, E-26, E-27, E-28, E-29, E-30, E-31, E-32, E-33, E-34, E-35, E-36, E-38, E-39, E-40, E-41, E-42, E-43, E-44, E-45, E-46, E-47, E-48, E-49, E-50, E-51, E-52, E-53, E-54, E-57, E-58, E-59, E-60, E-61, E-64, E-65, E-66, E-67, E-68, E-69, E-70, E-77, E-78, E-80, E-81, E-82, E-83, E-84, E-85, E-86, E-87, E-88, E-90, E-91, E-92, E-94, E-95, E-96, E-97, E-98, E-99, E-100, E-101, E-103, E-104, E-105, E-110, E-111, E-112, E-113, E-114, E-115, E-116, E-117, E-118, F-1, F-2, F-3, F-4, F-5, F-6, F-7, F-8, F-9, F-10, F-11, F-12, F-13

Example B4: *Blumeria Graminis* f. Sp. *tritici* (*Erysiphe graminis* f. Sp. *tritici*)/Wheat/Leaf Disc Preventative (Powdery Mildew on Wheat)

Wheat leaf segments cv. Kanzler are placed on agar in a multiwell plate (24-well format) and sprayed with the formulated test compound diluted in water. The leaf disks are inoculated by shaking powdery mildew infected plants above the test plates 1 day after application. The inoculated leaf disks are incubated at 20° C. and 60% rh under a light regime of 24 h darkness followed by 12 h light/12 h darkness in a climate chamber and the activity of a compound is assessed as percent disease control compared to untreated when an appropriate level of disease damage appears on untreated check leaf segments (6-8 days after application).

The following compounds gave at least 80% control of *Blumeria graminis* f. sp. *tritici* at 200 ppm when compared to untreated control under the same conditions, which showed extensive disease development:

E-3, E-4, E-7, E-15, E-16, E-17, E-18, E-19, E-22, E-24, E-25, E-26, E-27, E-28, E-29, E-32, E-34, E-35, E-38, E-39, E-40, E-41, E-42, E-44, E-45, E-47, E-48, E-50, E-51, E-54, E-57, E-58, E-59, E-60, E-61, E-64, E-66, E-67, E-68, E-69, E-70, E-75, E-77, E-78, E-80, E-81, E-82, E-83, E-84, E-85, E-86, E-87, E-88, E-90, E-91, E-92, E-94, E-95, E-96, E-97, E-98, E-99, E-100, E-101, E-103, E-104, E-105, E-108, E-109, E-111, E-114, E-115, E-116, E-117, E-118, F-1, F-4, F-5, F-6, F-7, F-8, F-9, F-10, F-11, F-12, F-13

Example B5: *Fusarium culmorum*/Wheat/Spikelet Preventative (Head Blight)

Wheat spikelets cv. Monsun are placed on agar in multiwell plates (24-well format) and sprayed with the formulated test compound diluted in water. The spikelets are inoculated with a spore suspension of the fungus 1 day after application. The inoculated spikelets are incubated at 20° C. and 60% rh under a light regime of 72 h semi darkness followed by 12 h light/12 h darkness in a climate chamber and the activity of a compound is assessed as percent disease control compared to untreated when an appropriate level of disease damage appears on untreated check spikelets (6-8 days after application).

The following compounds gave at least 80% control of *Fusarium culmorum* at 200 ppm when compared to untreated control under the same conditions, which showed extensive disease development:
E-68, E-92, E-103, E-117

Example B6: *Phaeosphaeria Nodorum* (*Septoria nodorum*)/Wheat/Leaf Disc Preventative (Glume Blotch)

Wheat leaf segments cv. Kanzler are placed on agar in a multiwell plate (24-well format) and sprayed with the formulated test compound diluted in water. The leaf disks are inoculated with a spore suspension of the fungus 2 days after application. The inoculated test leaf disks are incubated at 20° C. and 75% rh under a light regime of 12 h light/12 h darkness in a climate cabinet and the activity of a compound is assessed as percent disease control compared to untreated when an appropriate level of disease damage appears in untreated check leaf disks (5-7 days after application).

The following compounds gave at least 80% control of *Phaeosphaeria nodorum* at 200 ppm when compared to untreated control under the same conditions, which showed extensive disease development:
E-1, E-2, E-3, E-4, E-6, E-7, E-11, E-19, E-20, E-24, E-26, E-29, E-30, E-31, E-32, E-36, E-40, E-42, E-44, E-45, E-47, E-48, E-49, E-50, E-53, E-54, E-57, E-58, E-59, E-60, E-65, E-66, E-67, E-68, E-70, E-75, E-78, E-81, E-82, E-83, E-84, E-85, E-86, E-88, E-90, E-92, E-94, E-96, E-99, E-100, E-101, E-103, E-104, E-105, E-110, E-111, E-112, E-113, E-114, E-118, F-1, F-2, F-3, F-4, F-5, F-6, F-7, F-8, F-10, F-11, F-12, F-13

Example B7: *Monographella nivalis* (*Microdochium Nivale*)/Liquid Culture (Foot Rot Cereals)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

The following compounds gave at least 80% control of *Monographella nivalis* at 20 ppm when compared to untreated control under the same conditions, which showed extensive disease development:

E-1, E-2, E-3, E-4, E-5, E-6, E-7, E-9, E-10, E-11, E-12, E-14, E-15, E-16, E-17, E-18, E-19, E-20, E-21, E-22, E-23, E-24, E-25, E-26, E-27, E-28, E-29, E-30, E-31, E-32, E-33, E-34, E-35, E-36, E-37, E-38, E-39, E-40, E-41, E-42, E-43, E-44, E-45, E-46, E-47, E-48, E-49, E-50, E-51, E-52, E-53, E-54, E-55, E-57, E-58, E-59, E-60, E-61, E-64, E-65, E-66, E-67, E-68, E-69, E-70, E-75, E-76, E-77, E-78, E-80, E-81, E-82, E-83, E-84, E-85, E-86, E-87, E-88, E-89, E-90, E-91, E-92, E-94, E-95, E-96, E-97, E-98, E-99, E-100, E-101, E-103, E-104, E-105, E-108, E-109, E-110, E-111, E-112, E-113, E-114, E-115, E-116, E-117, E-118, F-1, F-2, F-3, F-4, F-5, F-6, F-7, F-8, F-9, F-11, F-12, F-13

Example B8: *Mycosphaerella arachidis* (*Cercospora arachidicola*)/Liquid Culture (Early Leaf Spot)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

The following compounds gave at least 80% control of *Mycosphaerella arachidis* at 20 ppm when compared to untreated control under the same conditions, which showed extensive disease development:

E-1, E-2, E-3, E-4, E-5, E-6, E-7, E-9, E-10, E-11, E-12, E-14, E-15, E-16, E-17, E-18, E-19, E-20, E-21, E-22, E-23, E-24, E-25, E-26, E-27, E-28, E-29, E-30, E-31, E-32, E-33, E-34, E-35, E-36, E-37, E-38, E-39, E-40, E-41, E-42, E-43, E-44, E-45, E-46, E-47, E-48, E-49, E-50, E-51, E-52, E-53, E-54, E-55, E-57, E-58, E-59, E-60, E-61, E-64, E-65, E-66, E-67, E-68, E-69, E-70, E-75, E-76, E-77, E-78, E-80, E-81, E-82, E-83, E-84, E-85, E-86, E-87, E-88, E-90, E-91, E-92, E-94, E-95, E-96, E-97, E-98, E-99, E-100, E-101, E-103, E-104, E-105, E-108, E-109, E-110, E-111, E-112, E-113, E-114, E-115, E-116, E-117, E-118, F-1, F-2, F-3, F-4, F-5, F-6, F-7, F-8, F-9, F-10, F-11, F-12, F-13

Example B9: *Phakopsora pachyrhizi*/Soybean/Preventative (Soybean Rust)

Soybean leaf disks are placed on agar in multiwell plates (24-well format) and sprayed with test solutions. After drying, the leaf disks are inoculated with a spore suspension of the fungus. After appropriate incubation the activity of a compound is assessed approx. 12 dpi (days after inoculation) as preventive fungicidal activity.

The following compounds gave at least 80% control of *Phakopsora pachyrhizi* at 200 ppm when compared to untreated control under the same conditions, which showed extensive disease development:

E-1, E-5, E-11, E-26, E-29, E-31, E-32, E-36, E-38, E-40, E-41, E-42, E-44, E-45, E-46, E-48, E-54, E-60, E-66, E-67, E-68, E-69, E-70, E-75, E-78, E-83, E-88, E-90, E-92, E-94, E-95, E-96, E-100, E-101, E-104, E-105, E-110, E-111, E-112, E-113, E-114, E-115, E-118, F-1, F-2, F-3, F-4, F-5, F-6, F-7, F-8

The following compounds gave at least 50% control of *Phakopsora pachyrhizi* at 200 ppm when compared to untreated control under the same conditions, which showed extensive disease development:

E-1, E-2, E-3, E-4, E-5, E-7, E-11, E-20, E-26, E-27, E-29, E-30, E-31, E-32, E-35, E-36, E-37, E-38, E-40, E-41, E-42, E-44, E-45, E-46, E-47, E-48, E-50, E-51, E-52, E-54, E-57, E-58, E-59, E-60, E-61, E-64, E-66, E-67, E-68, E-69, E-70, E-75, E-77, E-78, E-80, E-81, E-82, E-83, E-84, E-85, E-87, E-88, E-89, E-90, E-91, E-92, E-94, E-95, E-96, E-97,

E-98, E-99, E-100, E-101, E-103, E-104, E-105, E-110, E-111, E-112, E-113, E-114, E-115, E-118, F-1, F-2, F-3, F-4, F-5, F-6, F-7, F-8

Example B10: *Phytophthora infestans*/Tomato/Leaf Disc Preventative (Late Blight)

Tomato leaf disks are placed on water agar in multiwell plates (24-well format) and sprayed with the formulated test compound diluted in water. The leaf disks are inoculated with a spore suspension of the fungus 1 day after application. The inoculated leaf disks are incubated at 16° C. and 75% rh under a light regime of 24 h darkness followed by 12 h light/12 h darkness in a climate cabinet and the activity of a compound is assessed as percent disease control compared to untreated when an appropriate level of disease damage appears in untreated check leaf disks (5-7 days after application).

The following compounds gave at least 80% control of *Phytophthora infestans* at 200 ppm when compared to untreated control under the same conditions, which showed extensive disease development:

E-1, E-3, E-4, E-5, E-6, E-7, E-12, E-18, E-19, E-20, E-21, E-22, E-23, E-24, E-25, E-26, E-29, E-30, E-31, E-32, E-34, E-35, E-36, E-38, E-39, E-40, E-43, E-44, E-45, E-46, E-47, E-48, E-49, E-50, E-52, E-53, E-54, E-57, E-58, E-59, E-60, E-61, E-67, E-70, E-76, E-78, E-80, E-81, E-82, E-83, E-87, E-88, E-90, E-92, E-94, E-95, E-96, E-97, E-98, E-99, E-100, E-101, E-103, E-110, E-113, E-114, E-116, E-118, F-1, F-2, F-4, F-5, F-6, F-8, F-9, F-10, F-11, F-12, F-13

Example B11: *Plasmopara viticola*/Grape/Leaf Disc Preventative (Late Blight)

Grape vine leaf disks are placed on water agar in multiwell plates (24-well format) and sprayed with the formulated test compound diluted in water. The leaf disks are inoculated with a spore suspension of the fungus 1 day after application. The inoculated leaf disks are incubated at 19° C. and 80% rh under a light regime of 12 h light/12 h darkness in a climate cabinet and the activity of a compound is assessed as percent disease control compared to untreated when an appropriate level of disease damage appears in untreated check leaf disks (6-8 days after application).

The following compounds gave at least 80% control of *Plasmopara viticola* at 200 ppm when compared to untreated control under the same conditions, which showed extensive disease development:

E-1, E-2, E-3, E-5, E-6, E-7, E-11, E-12, E-18, E-19, E-20, E-21, E-23, E-24, E-25, E-26, E-27, E-28, E-29, E-30, E-31, E-32, E-33, E-34, E-35, E-36, E-37, E-38, E-39, E-40, E-41, E-42, E-43, E-44, E-45, E-46, E-47, E-48, E-49, E-50, E-51, E-52, E-53, E-54, E-57, E-58, E-59, E-60, E-61, E-64, E-65, E-66, E-67, E-68, E-69, E-70, E-75, E-76, E-77, E-78, E-80, E-81, E-82, E-83, E-84, E-85, E-87, E-88, E-89, E-90, E-92, E-94, E-95, E-96, E-98, E-99, E-100, E-101, E-103, E-105,
E-106, E-109, E-110, E-111, E-112, E-113, E-114, E-116, E-117, E-118, F-1, F-2, F-3, F-4, F-5, F-6, F-7, F-8, F-9, F-10, F-11, F-12, F-13

Example B12: *Puccinia recondita* f. Sp. *tritici*/Wheat/Leaf Disc Curative (Brown Rust)

Wheat leaf segments cv. Kanzler are placed on agar in multiwell plates (24-well format). The leaf segments are inoculated with a spore suspension of the fungus. Plates are stored in darkness at 19° C. and 75% rh. The formulated test compound diluted in water is applied 1 day after inoculation. The leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (6-8 days after application).

The following compounds gave at least 80% control of *Puccinia recondita* f. sp. *tritici* at 200 ppm when compared to untreated control under the same conditions, which showed extensive disease development:

E-5, E-7, E-11, E-15, E-16, E-17, E-18, E-20, E-21, E-23, E-24, E-25, E-26, E-27, E-28, E-29, E-30, E-31, E-32, E-35, E-36, E-37, E-38, E-39, E-40, E-41, E-42, E-43, E-45, E-46, E-47, E-48, E-49, E-51, E-57, E-58, E-60, E-64, E-65, E-66, E-67, E-68, E-69, E-70, E-77, E-80, E-82, E-88, E-90, E-92, E-94, E-95, E-96, E-99, E-101, E-103, E-110, E-112, E-114, E-115, E-116, E-117, E-118, F-1, F-2, F-3, F-4, F-5, F-6, F-7, F-8, F-9, F-11, F-12, F-13

Example B13: *Puccinia recondita* f. Sp. *Tritici*/Wheat/Leaf Disc Preventative (Brown Rust)

Wheat leaf segments cv. Kanzler are placed on agar in multiwell plates (24-well format) and sprayed with the formulated test compound diluted in water. The leaf disks are inoculated with a spore suspension of the fungus 1 day after application. The inoculated leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (7-9 days after application).

The following compounds gave at least 80% control of *Puccinia recondita* f. sp. *tritici* at 200 ppm when compared to untreated control under the same conditions, which showed extensive disease development:

E-1, E-2, E-3, E-4, E-5, E-6, E-7, E-11, E-12, E-15, E-16, E-17, E-18, E-19, E-20, E-21, E-22, E-23, E-24, E-25, E-26, E-27, E-28, E-29, E-30, E-31, E-32, E-33, E-34, E-35, E-36, E-37, E-38, E-39, E-40, E-41, E-42, E-43, E-44, E-45, E-46, E-47, E-48, E-49, E-50, E-51, E-52, E-53, E-54, E-55, E-57, E-58, E-59, E-60, E-61, E-65, E-66, E-67, E-68, E-69, E-70, E-75, E-76, E-77, E-78, E-80, E-81, E-82, E-83, E-84, E-85, E-86, E-87, E-88, E-89, E-90, E-91, E-92, E-94, E-95, E-96, E-97, E-98, E-99, E-100, E-101, E-103, E-104, E-105, E-106, E-107, E-108, E-109, E-110, E-113, E-114, E-115, E-116, E-117, E-118, F-1, F-2, F-3, F-4, F-5, F-6, F-7, F-8, F-9, F-10, F-11, F-12, F-13

Example B14: *Magnaporthe grisea* (*Pyricularia oryzae*)/Rice/Leaf Disc Preventative (Rice Blast)

Rice leaf segments cv. Ballila are placed on agar in a multiwell plate (24-well format) and sprayed with the formulated test compound diluted in water. The leaf segments are inoculated with a spore suspension of the fungus 2 days after application. The inoculated leaf segments are incubated at 22° C. and 80% rh under a light regime of 24 h darkness followed by 12 h light/12 h darkness in a climate cabinet and the activity of a compound is assessed as percent disease control compared to untreated when an appropriate level of disease damage appears in untreated check leaf segments (5-7 days after application).

The following compounds gave at least 80% control of *Magnaporthe grisea* at 200 ppm when compared to untreated control under the same conditions, which showed extensive disease development:

E-1, E-2, E-5, E-6, E-7, E-10, E-11, E-12, E-18, E-19, E-20, E-24, E-25, E-26, E-27, E-29, E-30, E-31, E-32, E-34, E-35, E-36, E-38, E-39, E-40, E-41, E-42, E-43, E-44, E-45, E-46, E-47, E-49, E-50, E-51, E-52, E-53, E-57, E-58, E-59, E-60, E-61, E-64, E-65, E-68, E-69, E-70, E-76, E-78, E-80, E-81, E-82, E-83, E-85, E-86, E-88, E-90, E-92, E-98, E-99, E-100, E-103, E-104, E-105, E-110, E-112, E-113, E-114, E-118, F-1, F-2, F-3, F-4, F-5, F-6, F-7, F-10, F-11, F-12, F-13

Example B15: *Pyrenophora teres*/Barley/Leaf Disc Preventative (Net Blotch)

Barley leaf segments cv. Hasso are placed on agar in a multiwell plate (24-well format) and sprayed with the formulated test compound diluted in water. The leaf segments are inoculated with a spore suspension of the fungus 2 days after application. The inoculated leaf segments are incubated at 20° C. and 65% rh under a light regime of 12 h light/12 h darkness in a climate cabinet and the activity of a compound is assessed as disease control compared to untreated when an appropriate level of disease damage appears in untreated check leaf segments (5-7 days after application).

The following compounds gave at least 80% control of *Pyrenophora teres* at 200 ppm when compared to untreated control under the same conditions, which showed extensive disease development:

E-1, E-2, E-12, E-34, E-36, E-38, E-39, E-42, E-44, E-45, E-54, E-67, E-70, E-75, E-78, E-81, E-82, E-83, E-89, E-105, E-108, E-109, E-112, E-114, E-118, F-1, F-2, F-4, F-5, F-7, F-10, F-11, F-12, F-13

Example B16: *Pythium ultimum*/Liquid Culture (Seedling Damping Off)

Mycelia fragments and oospores of a newly grown liquid culture of the fungus are directly mixed into nutrient broth (PDB potato dextrose broth). After placing a (DMSO) solution of test compound into a microtiter plate (96-well format), the nutrient broth containing the fungal mycelia/spore mixture is added. The test plates are incubated at 24° C. and the inhibition of growth is determined photometrically 2-3 days after application.

The following compounds gave at least 80% control of *Pythium ultimum* at 20 ppm when compared to untreated control under the same conditions, which showed extensive disease development:

E-5, E-7, E-21, E-68, E-80, E-92, E-103, F-9

Example B17: *Thanatephorus cucumeris* (*Rhizoctonia solani*)/Liquid Culture (Foot Rot, Damping-Off)

Mycelia fragments of a newly grown liquid culture of the fungus are directly mixed into nutrient broth (PDB potato dextrose broth). After placing a (DMSO) solution of the test compounds into a microtiter plate (96-well format), the nutrient broth containing the fungal material is added. The test plates are incubated at 24° C. and the inhibition of growth is determined photometrically 3-4 days after application. The following compounds gave at least 80% control of *Thanatephorus cucumeris* at 20 ppm when compared to untreated control under the same conditions, which showed extensive disease development:

E-23, E-24, E-30, E-31, E-32, E-34, E-35, E-36, E-38, E-39, E-40, E-41, E-42, E-43, E-44, E-45, E-46, E-48, E-50, E-52, E-53, E-57, E-58, E-59, E-60, E-65, E-67, E-68, E-69, E-98, E-101

Example B18: *Sclerotinia sclerotiorum*/Liquid Culture (Cottony Rot)

Mycelia fragments of a newly grown liquid culture of the fungus are directly mixed into nutrient broth (PDB potato dextrose broth). After placing a (DMSO) solution of test compound into a microtiter plate (96-well format) the nutrient broth containing the fungal material is added. The test plates are incubated at 24° C. and the inhibition of growth is determined photometrically 3-4 days after application. The following compounds gave at least 80% control of *Sclerotinia sclerotiorum* at 20 ppm when compared to untreated control under the same conditions, which showed extensive disease development:

E-18, E-19, E-20, E-23, E-24, E-36, E-67, E-68, E-69, E-117, F-3, F-7

Example B19: *Mycosphaerella graminicola* (*Septoria tritici*)/Liquid Culture (*Septoria* Blotch)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

The following compounds gave at least 80% control of *Mycosphaerella graminicola* at 20 ppm when compared to untreated control under the same conditions, which showed extensive disease development:

E-1, E-2, E-3, E-4, E-5, E-6, E-7, E-9, E-10, E-11, E-12, E-14, E-15, E-16, E-17, E-18, E-19, E-20, E-21, E-22, E-23, E-24, E-25, E-26, E-27, E-28, E-29, E-30, E-31, E-32, E-33, E-34, E-35, E-36, E-37, E-38, E-39, E-40, E-41, E-42, E-43, E-44, E-45, E-46, E-47, E-48, E-49, E-50, E-51, E-52, E-53, E-54, E-55, E-57, E-58, E-59, E-60, E-61, E-64, E-65, E-66, E-67, E-68, E-69, E-70, E-75, E-76, E-77, E-78, E-80, E-81, E-82, E-83, E-84, E-85, E-86, E-87, E-88, E-89, E-90, E-91, E-92, E-94, E-95, E-96, E-97, E-98, E-99, E-100, E-101, E-103, E-104, E-105, E-107, E-108, E-109, E-110, E-113, E-114, E-115, E-116, E-117, E-118, F-1, F-2, F-3, F-4, F-5, F-6, F-7, F-8, F-9, F-10, F-11, F-12, F-13

Comparative Data:

The biological activity of compounds E-15, E-40, E-42, E-70, E-92, E-105, F-8, F-9, of the invention are compared to the reference compounds X-1. Reference compound X-1 is specifically disclosed on page 13 of EP 0 212 859 as compound no. 140.

The data are presented as the percentage of disease control of each compound for the biological tests against *G. lagenarium* (Example B3), *P. recondita* preventative (Example B13), *P. teres* (Example B15) and *M. graminicola* (Example B19) as described above. The testing rates of each biological test is specifically described in table C1 below.

TABLE C1

| | | Comparative Data | |
|---|---|---|---|
| Compound | Concentration (ppm) | Pathogen (test method) | Disease control (%) |
| F-9 | 20 | *G. lagenarium* (B3) | 100 |
| | 60 | *P. recondita* prev (B13) | 100 |
| | 200 | *P. teres* (B15) | 0 |
| | 6 | *M. graminicola* (B19) | 90 |
| F-8 | 20 | *G. lagenarium* (B3) | 100 |
| | 60 | *P. recondita* prev (B13) | 100 |
| | 20 | *P. teres* (B15) | 50 |
| | 6 | *M. graminicola* (B19) | 100 |
| E-42 | 20 | *G. lagenarium* (B3) | 100 |
| | 60 | *P. recondita* prev (B13) | 100 |
| | 200 | *P. teres* (B15) | 90 |
| | 6 | *M. graminicola* (B19) | 100 |
| E-92 | 20 | *G. lagenarium* (B3) | 100 |
| | 60 | *P. recondita* prev (B13) | 100 |
| | 200 | *P. teres* (B15) | 0 |
| | 6 | *M. graminicola* (B19) | 100 |
| E-70 | 20 | *G. lagenarium* (B3) | 100 |
| | 60 | *P. recondita* prev (B13) | 100 |
| | 200 | *P. teres* (B15) | 90 |
| | 6 | *M. graminicola* (B19) | 100 |

TABLE C1-continued

Comparative Data

| Compound | Concentration (ppm) | Pathogen (test method) | Disease control (%) |
|---|---|---|---|
| E-40 | 20 | G. lagenarium (B3) | 100 |
|  | 60 | P. recondita prev (B13) | 70 |
|  | 200 | P. teres (B15) | — |
|  | 6 | M. graminicola (B19) | 100 |
| E-105 | 20 | G. lagenarium (B3) | 90 |
|  | 60 | P. recondita prev (B13) | 100 |
|  | 200 | P. teres (B15) | 90 |
|  | 6 | M. graminicola (B19) | 100 |
| E-15 | 20 | G. lagenarium (B3) | 20 |
|  | 200 | P. recondita prev (B13) | 90 |
|  | 200 | P. teres (B15) | 50 |
|  | 6 | M. graminicola (B19) | 70 |
| X-1 | 20 | G. lagenarium (B3) | 0 |
|  | 200 | P. recondita prev (B13) | 0 |
|  | 200 | P. teres (B15) | 0 |
|  | 6 | M. graminicola (B19) | 20 |

Example D: Comparative Photostability Data

The photostability data of compounds E-40, E-41, E-42, E-44, E-67, E-68, E-70, E-88, E-90, E-92, E-101 and E-105 of the invention are compared to the reference compound X-1.

The testing method to measure the photostability data of each compound in table is D1 is as specifically described below. The objective of the photostability assay was to determine the stability of the individual test compounds in a strictly controlled and reproducible environment allowing a comparison of their photostability.

Method: Compounds were dissolved in methanol (HPLC grade) to give 1 g/L stock solutions. Compound stock solution (2 μl) was spotted onto microscope slides in a 3D printed holder and put into the Atlas Suntest. The spectral output power of the Suntest was set to 750 W/m$^2$, which is considered typical of the daily maximum (noon) irradiance level on a very bright British Summer day. At specific time points slides were removed from the Suntest and placed in 4D vials. Wash solvent made up of 50:40:10 $H_2O$:MeCN:THF (1 mL) is then added to the vials and whirlimixed. The resulting solution is then subsampled to an HPLC vial to be analysed. A Waters UPLC system with Photodiode Array was used with a Waters reverse phase column (BEH C18, 100×2.1 mm×1.7 μm) and acetonitrile (HPLC grade) acidified water (0.2% formic acid) mobile phase at a flow rate of 0.6 mL/min. Peak detection was at the optimum wavelength and peak areas were used for quantification Initial and subsequent measurements of peak area attributable to the test compound were used to provide a % parent remaining at 3 hours.

TABLE D1

| | Photostability data | |
|---|---|---|
| Compound | Structure | % Parent Remaining @ 3 hrs |
| X-1 | | 9 |
| E-105 | | 74 |
| E-101 | | 38 |
| E-92 | | 33 |
| E-40 | | 65 |

TABLE D1-continued

| | Photostability data | |
|---|---|---|
| Compound | Structure | % Parent Remaining @ 3 hrs |
| E-90 | | 42 |
| E-88 | | 34 |
| E-67 | | 37 |
| E-68 | | 40 |
| E-44 | | 69 |

TABLE D1-continued

Photostability data

| Compound | Structure | % Parent Remaining @ 3 hrs |
|---|---|---|
| E-70 | 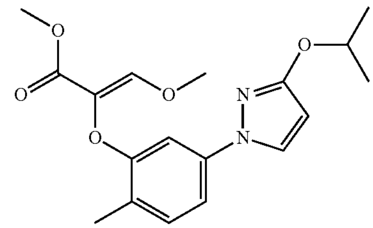 [SMILES: CO/C=C(\Oc1cc(-n2ccc(OC(C)C)n2)ccc1C)C(=O)OC] | 25 |
| E-41 | 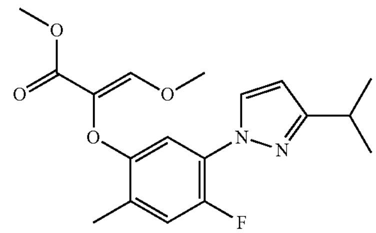 [SMILES: CO/C=C(\Oc1cc(-n2ccc(C(C)C)n2)c(F)cc1C)C(=O)OC] | 28 |
| E-42 | 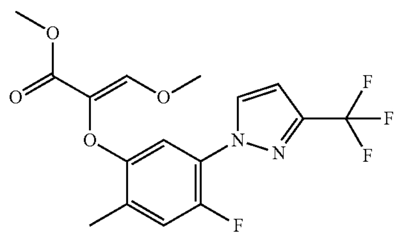 [SMILES: CO/C=C(\Oc1cc(-n2ccc(C(F)(F)F)n2)c(F)cc1C)C(=O)OC] | 24 |

Example E: Comparative Biological Activity Against *Phakopsora pachyrhizi* (Soybean Rust)

The biological activity of compounds E-40, E-92, E-105, F-2, and F-6 of the invention are compared to the reference compounds X-1, X-2, and X-3. Reference compounds X-1 is specifically disclosed on page 13 of EP0212859 as compound 140 and reference compound X-3 is specifically disclosed on page 61 of WO01/00562 as Compound 1-91.

Method: Soybean leaf disks are placed on agar in multi-well plates (24-well format) and sprayed with test solutions. After drying, the leaf disks are inoculated with a spore suspension of the fungus. After appropriate incubation the activity of a compound is assessed approx. 12 dpi (days after inoculation) as preventive fungicidal activity.

The data are presented as the percentage of disease control of each compound for the biological tests and testing rates described below in table E1.

TABLE E1

Biological activity against *Phakopsora pachyrhizi* (Soybean rust):

| Compound | Compound structure | Concentration (ppm) | control (%) |
|---|---|---|---|
| Compound E-40 | 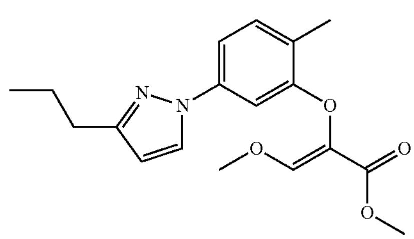 [SMILES: CCCc1ccn(-c2ccc(C)c(O/C(=C\OC)C(=O)OC)c2)n1] | 200 | 100 |
| | | 60 | 100 |
| | | 20 | 95 |
| | | 6 | 90 |
| | | 2 | 35 |
| | | 0

TABLE E1-continued

*Biological activity against Phakopsora pachyrhizi* (Soybean rust):

| Compound | Compound structure | Concentration (ppm) | control (%) |
|---|---|---|---|
| Compound E-92 | 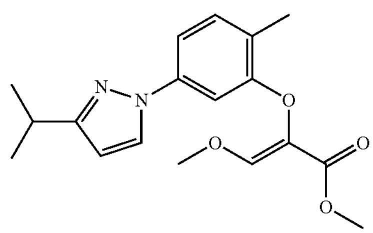 [SMILES: CO/C=C(\Oc1cc(-n2ccc(C(C)C)n2)ccc1C)C(=O)OC] | 200<br>60<br>20<br>6<br>2<br>0.6 | 100<br>100<br>90<br>35<br>0<br>0 |
| Compound E-105 | 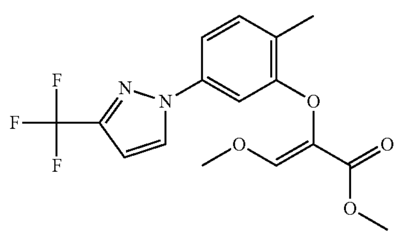 [SMILES: CO/C=C(\Oc1cc(-n2ccc(C(F)(F)F)n2)ccc1C)C(=O)OC] | 200<br>60<br>20<br>6<br>2<br>0.6 | 100<br>100<br>95<br>20<br>0<br>0 |
| Compound F-2 | 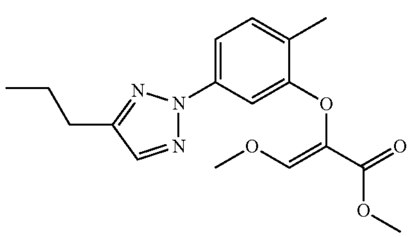 [SMILES: CCCc1cnn(-c2ccc(C)c(O/C(=C\OC)C(=O)OC)c2)n1] | 200<br>60<br>20<br>6<br>2<br>0.6 | 100<br>100<br>90<br>50<br>20<br>0 |
| Compound F-6 | 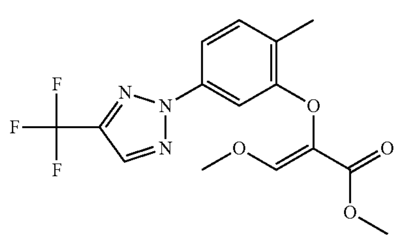 [SMILES: CO/C=C(\Oc1cc(-n2ncc(C(F)(F)F)n2)ccc1C)C(=O)OC] | 200<br>60<br>20<br>6<br>2<br>0.6 | 100<br>100<br>80<br>20<br>0<br>0 |
| Reference X-1 (Compound 140 of EP 0 212 859) | 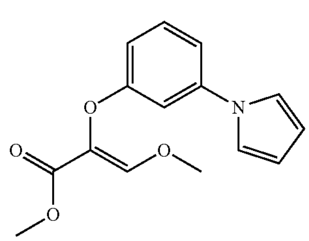 [SMILES: CO/C=C(\Oc1cccc(-n2cccc2)c1)C(=O)OC] | 200<br>60<br>20<br>6<br>2<br>0.6 | 45<br>10<br>10<br>0<br>0<br>0 |
| Reference Compound X-2 | 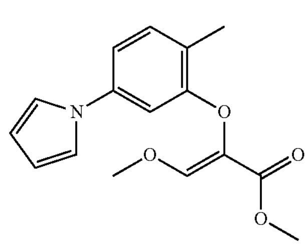 [SMILES: CO/C=C(\Oc1cc(-n2cccc2)ccc1C)C(=O)OC] | 200<br>60<br>20<br>6<br>2<br>0.6 | 100<br>70<br>0<br>0<br>0<br>0 |

TABLE E1-continued

Biological activity against *Phakopsora pachyrhizi* (Soybean rust):

| Compound | Compound structure | Concentration (ppm) | control (%) |
|---|---|---|---|
| Reference X-3 (Compound I-91 of WO 2001000562) | 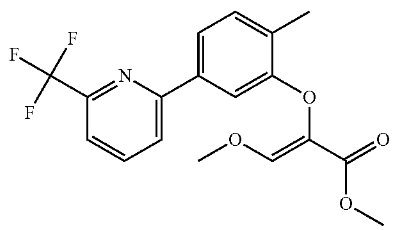 [SMILES: CO/C=C(\Oc1cc(-c2cccc(C(F)(F)F)n2)ccc1C)C(=O)OC] | 200<br>60<br>20<br>6<br>2<br>0.6 | 85<br>50<br>10<br>0<br>0<br>0 |

The invention claimed is:

1. A compound selected from the group consisting of methyl (Z)-3-methoxy-2-[2-methyl-5-(3-propylpyrazol-1-yl)phenoxy]prop-2-enoate, methyl (Z)-2-[4-fluoro-5-(3-isopropylpyrazol-1-yl)-2-methyl-phenoxy]-3-methoxy-prop-2-enoate, methyl (Z)-2-[4-fluoro-2-methyl-5-[3-(trifluoromethyl)pyrazol-1-yl]phenoxy]-3-methoxy-prop-2-enoate, methyl (Z)-3-methoxy-2-[2-methyl-5-(3-sec-butylpyrazol-1-yl)phenoxy]prop-2-enoate, methyl (Z)-2-[5-[3-(1-fluorocyclopropyl)pyrazol-1-yl]-2-methyl-phenoxy]-3-methoxy-prop-2-enoate, methyl (Z)-2-[5-[3-(1,1-difluoroethyl)pyrazol-1-yl]-2-methyl-phenoxy]-3-methoxy-prop-2-enoate, methyl (Z)-2-[5-(3-isopropoxypyrazol-1-yl)-2-methyl-phenoxy]-3-methoxy-prop-2-enoate, methyl (Z)-2-[5-(3-cyclobutylpyrazol-1-yl)-2-methyl-phenoxy]-3-methoxy-prop-2-enoate, methyl (Z)-2-[5-(3-isobutylpyrazol-1-yl)-2-methyl-phenoxy]-3-methoxy-prop-2-enoate, methyl (Z)-2-[5-(3-isopropylpyrazol-1-yl)-2-methyl-phenoxy]-3-methoxy-prop-2-enoate, methyl (Z)-3-methoxy-2-[2-methyl-5-(4-propyltriazol-2-yl)phenoxy]prop-2-enoate, methyl (Z)-3-methoxy-2-[2-methyl-5-[4-(trifluoromethyl)triazol-2-yl]phenoxy]prop-2-enoate and methyl (Z)-2-[5-(4-cyclopropyltriazol-2-yl)-2-methyl-phenoxy]-3-methoxy-prop-2-enoate.

2. The compound according to claim 1, wherein the compound is

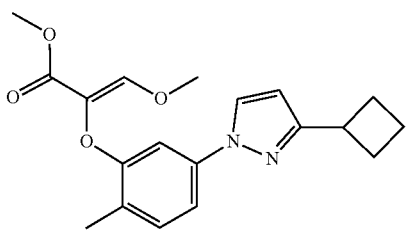 [SMILES: CO/C=C(\Oc1cc(-n2ccc(C3CCC3)n2)ccc1C)C(=O)OC]

Methyl (Z)-2-[5-(3-cyclobutylpyrazol-1-yl)-2-methyl-phenoxy]-3-methoxy-prop-2-enoate.

3. The compound according to claim 1, wherein the compound is

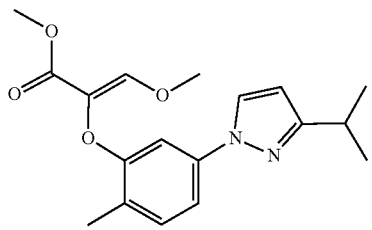 [SMILES: CO/C=C(\Oc1cc(-n2ccc(C(C)C)n2)ccc1C)C(=O)OC]

methyl (Z)-2-[5-(3-isopropylpyrazol-1-yl)-2-methyl-phenoxy]-3-methoxy-prop-2-enoate.

4. The compound according to claim 1, wherein the compound is

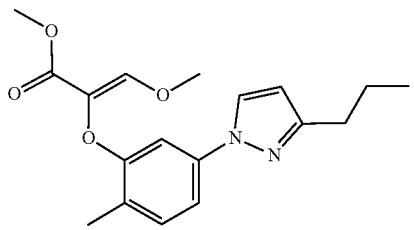 [SMILES: CCCc1ccn(-c2ccc(C)c(O/C(=C\OC)C(=O)OC)c2)n1]

methyl (Z)-3-methoxy-2-[2-methyl-5-(3-propylpyrazol-1-yl)phenoxy]prop-2-enoate.

5. The compound according to claim 1, wherein the compound is methyl (Z)-3-methoxy-2-[2-methyl-5-(4-propyltriazol-2-yl)phenoxy]prop-2-enoate.

6. An agrochemical composition comprising a fungicidally effective amount of a compound according to claim 1 and an agrochemically-acceptable diluent or carrier.

7. The composition according to claim 6, further comprising at least one additional active ingredient.

8. A method of controlling or preventing infestation of useful plants by phytopathogenic microorganisms, comprising applying a fungicidally effective amount of a compound according to claim 1, or a composition comprising this compound as active ingredient, to the plants, to parts thereof or the locus thereof.

\* \* \* \* \*